United States Patent [19]
Grieve et al.

[11] Patent Number: 6,146,870
[45] Date of Patent: Nov. 14, 2000

[54] FLEA PROTEASE PROTEINS

[75] Inventors: Robert B. Grieve, Windsor; Keith E. Rushlow; Shirley Wu Hunter, both of Ft. Collins; Glenn R. Frank, Wellington; Gary L. Stiegler, Ft. Collins, all of Colo.

[73] Assignee: Heska Corporation, Ft. Collins, Colo.

[21] Appl. No.: 08/485,443

[22] Filed: Jun. 7, 1995

Related U.S. Application Data

[63] Continuation-in-part of application No. 08/326,773, Oct. 18, 1994, Pat. No. 5,766,609, which is a continuation-in-part of application No. 07/806,482, Dec. 13, 1991, Pat. No. 5,356,622.

[51] Int. Cl.⁷ .............................. C12N 9/50; A61K 39/00
[52] U.S. Cl. ...................... 435/219; 530/350; 530/324; 530/325; 530/326; 530/327; 530/328; 530/329; 424/185.1
[58] Field of Search .............................. 424/185.1, 184.1; 530/300, 350, 855, 858; 435/219, 213, 212

[56] References Cited

U.S. PATENT DOCUMENTS

| | | |
|---|---|---|
| 4,800,159 | 1/1989 | Mullis et al. . |
| 4,879,213 | 11/1989 | Fox et al. . |
| 5,288,612 | 2/1994 | Griffin et al. . |
| 5,304,482 | 4/1994 | Sambrook et al. . |
| 5,356,622 | 10/1994 | Heath et al. ...................... 424/265.1 |

FOREIGN PATENT DOCUMENTS

| | | |
|---|---|---|
| 0571911 | 12/1993 | European Pat. Off. . |
| 9003433 | 4/1990 | WIPO . |
| WO 93/23542 | 11/1993 | WIPO . |
| WO 94/25583 | 11/1994 | WIPO . |

OTHER PUBLICATIONS

Jany et al (1983) BBRC vol. 111 (1), 1–7.
Sarkar et al (1990) Genomics vol. 6 (1), 133–143.
Lazar et al (1988) Mol J Cell Biol. vol. 8 (3), 1243–1252.
Burgess et al (1990) J. Cell Biol. vol. 111, 2129–2138.
Azad et al., *Am. J. Trop. Med. Hyg.*, 1987, 37:629–635.
Billingsley, *Annu. Rev. Entomol.*, 1990, 35:219–248.
Borovsky et al., *FASEB J.*, 1990, 4:3015–3020.
Borovsky, *Arch. Insect Biochem. Physiol.*, 1988, 7:187–210.
Casu et al., *Insect Mol. Biol.*, 1994, 3(4):201–211.
Casu et al., *Insect Mol. Biol.*, 1994, 3(3):159–170.
Cherney et al., *Am J. Trop. Med.*, 1939, 19:327–332.
Chinzei et al., *Med. Vet. Entomol.*, 1987, 1:409–416.
Elvin et al., *Mol. Gen. Genet.*, 1993, 240:132–139.
Halliwell, *J. Immunol.*, 1973, 110:422–430.
Halliwell et al. *J. Allerg. Clin. Immunol.*, 1978, 62:236–242.
Halliwell et al., *Vet. Immunol. Immunopathol.*, 8:215–223.
Hatfield, *Med. Vet. Entomol.*, 1988, 2:331–338.
Hatfield, *Med. Vet. Entomol.*, 1988, 2:339–345.
Houk et al., pp. 135–146, 1986, *Archives of Insect Biochemistry and Physiology*, vol. 3.
Johnston et al., *Int. J. Parasitol.*, 1986, 16(1):27–34.
Kalhok et al., *Insect Mol. Biol.*, 1993, 2(2):71–79.
Kay et al., *Am. J. Trop. Med. Hyg.*, 1994, 50(6) Suppl.:87–96.
Kemp et al., *Internat. J. Parasitol.*, 1986, 16, 115–120.
Kwochka, *Vet. Clin. North Am.*, 1987, 17:1235–1262.
Law et al., *Annu. Rev. Biochem.*, 1992, 61:87–111.
McFarlane, "Nutrition and Digestive Organs", in *Fundamentals of Insect Physiology*, M.S. Blum, ed., John Wiley and Sons, New York, New York, 1985, pp. 59–89.
Müller et al., *EMBO J.*, 1993, 12(7):2891–2900.
Nesbitt et al., *J. Am. Med. Assoc.*, 1978, 173:282–288.
Opdebeeck et al., *Immunol.*, 1988, 63:363–367.
Opdebeeck et al., *Parasite Immunol.*, 1988, 10:405–410.
Opdebeeck et al., *Immunol.*, 1989, 67:388.
Otieno et al., *Insect Sci. Applic.*, 1984, 5(4):297–302.
Ramos et al., *Insect Mol. Biol.*, 1993, 1(3):149–163.
Rand et al., *Proc. Natl. Acad. Sci. (USA)*, 1989, 86:9657–9661.
Ribiero, *Ann. Rev. Entomol.*, 1987, 32:463–478.
Sandeman et al., *Int. J. Parasitol.*, 1990, 20(8):1019–1023.
Schlein et al., *Physiolog. Entomol.*, 1976, 1:55–59.
Soulsby, in *Helminths, Arthropods and Protozoa of Domesticated Animals*, 7th ed., 1982, Lea and Febiger, eds., Philadelphia, PA, pp.378–384.
Vaughn et al., *J. Med. Entomol.*, 1988, 25:472–474.
Wikel, *Vet. Parasitol.*, 1984, 14:321–329.
Wikel, *Vet. Parasitol.*, 1988, 29:235–264.
Willadsen et al., *J. Immunol.*, 1989, 143:1346–1351.
Wong et al., *Immunol.*, 1989, 66, 149–155.
Young et al., 1963, *Exp. Parasitol.*, 13:155–166.
Roitt et al., 1985, *Immunology*, pp. 5.4–5.5.
Zwilling et al., 1975, *Febs Letters*, 60(2):247–249.

*Primary Examiner*—Marianne P. Allen
*Attorney, Agent, or Firm*—Sheridan Ross P.C.

[57] ABSTRACT

The present invention relates to flea serine protease and aminopeptidase proteins; to flea serine protease and aminopeptidase nucleic acid molecules, including those that encode such proteins; to antibodies raised against such proteins; and to compounds that inhibit flea serine protease and/or aminopeptidase activities. The present invention also includes methods to obtain such proteins, nucleic acid molecules, antibodies, and inhibitors. Also included in the present invention are therapeutic compositions comprising such proteins, nucleic acid molecules, antibodies, and/or inhibitors as well as the use of such therapeutic compositions to protect a host animal from flea infestation.

8 Claims, 9 Drawing Sheets

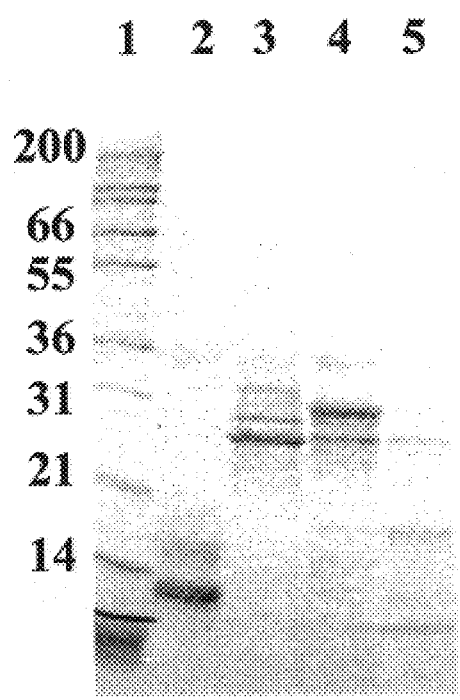
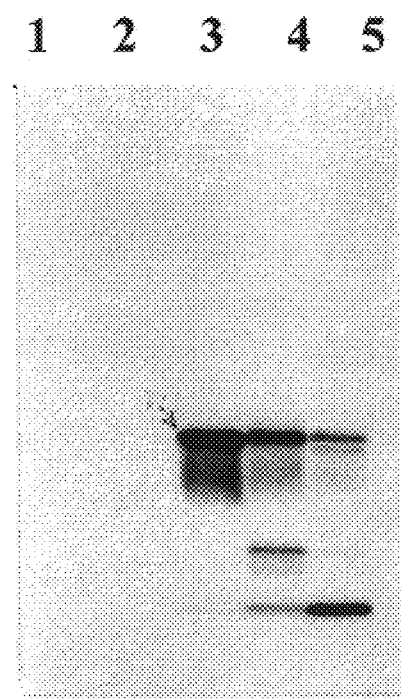
FIG. 5A
FIG. 5B

```
                           SEQUENCE LISTING (1) GENERAL INFORMATION:

(iii) NUMBER OF SEQUENCES: 79

(2) INFORMATION FOR SEQ ID NO:1:

(i) SEQUENCE CHARACTERISTICS:
         (A) LENGTH: 32 amino acids
         (B) TYPE: amino acid
         (C) STRANDEDNESS:
         (D) TOPOLOGY: linear (ii) MOLECULE TYPE: protein (xi) SEQUENCE DESCRIPTION: SEQ ID NO:1:

Ile Ile Gly Gly Glu Val Ala Gly Glu Gly Ser Ala Pro Tyr Gln Val
 1               5                  10                  15

Ser Leu Arg Thr Lys Glu Gly Asn His Phe Ser Gly Gly Ser Ile Leu
             20                  25                  30

(2) INFORMATION FOR SEQ ID NO:2:

(i) SEQUENCE CHARACTERISTICS:
         (A) LENGTH: 17 amino acids
         (B) TYPE: amino acid
         (C) STRANDEDNESS:
         (D) TOPOLOGY: linear (ii) MOLECULE TYPE: protein (xi) SEQUENCE DESCRIPTION: SEQ ID NO:2:

Xaa Val Gly Gly His Asp Thr Ser Ile Asp Xaa His Pro His Gln Val
 1               5                  10                  15

Thr (2) INFORMATION FOR SEQ ID NO:3:

(i) SEQUENCE CHARACTERISTICS:
         (A) LENGTH: 22 amino acids
         (B) TYPE: amino acid
         (C) STRANDEDNESS:
         (D) TOPOLOGY: linear (ii) MOLECULE TYPE: protein
```

(xi) SEQUENCE DESCRIPTION: SEQ ID NO:3:

Ile Val Gly Gly Ala Asp Ala Ala Pro Gly Asn Ala Pro Phe Gln Val
1               5                   10                  15

Ser Leu Arg Asp Lys Gly
            20

(2) INFORMATION FOR SEQ ID NO:4:

(i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:4:

Ile Val Gly Gly Gln Asp Ala Asp Ile Ala Lys Tyr Gly Tyr Gln Ala
1               5                   10                  15

Ser Leu Gln Val Phe Asn Glu His Phe Xaa Gly Ala Xaa Ile Leu Asn
            20                  25                  30

Asn Tyr (2) INFORMATION FOR SEQ ID NO:5:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:5:

Ile Val Gly Gly Thr Asp Val Asn Ile Glu Asn Phe Gly Trp Gln Val
1               5                   10                  15

Ser Leu Phe Asp Arg Asn Gly His Phe
            20                  25

(2) INFORMATION FOR SEQ ID NO:6:

(i) SEQUENCE CHARACTERISTICS:
        (A) LENGTH: 22 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:6:

Ile Val Gly Gly His Asp Thr Ser Ile Asp Lys His Pro Phe Gln Val
1               5                   10                  15

Ser Leu Ile Asp Lys Asn
            20

(2) INFORMATION FOR SEQ ID NO:7:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:7:

Val Val Gly Gly Leu Glu Ala Ala Glu Gly Ser Ala Pro Tyr Gln Val
1               5                  10                  15

Xaa Leu Gln Trp Gly Asn Phe
            20

(2) INFORMATION FOR SEQ ID NO:8:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:8:

Ile Val Gly Gly Glu Asp Ala Glu Leu Gly Glu Xaa Pro Thr Gln
1               5                  10                  15

(2) INFORMATION FOR SEQ ID NO:9:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:9:

Asp Glu Asp Gly Lys Asp Asp Ser Ala Pro Gly Glu Ile
1               5                  10

(2) INFORMATION FOR SEQ ID NO:10:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Xaa = Gln or Asn
        (B) LOCATION: 2

(xi) SEQUENCE DESCRIPTION: SEQ ID NO:10:

Cys Xaa Gly Asp Ser Gly Gly Pro Leu
1               5

(2) INFORMATION FOR SEQ ID NO:11:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:11:

TAAWGGWCCW CCYGAATCTC CCTGGCA                                   27

(2) INFORMATION FOR SEQ ID NO:12:

(i) SEQUENCE CHARACTERISTICS:

(A) LENGTH: 24 base pairs
            (B) TYPE: nucleic acid
            (C) STRANDEDNESS: single
            (D) TOPOLOGY: linear (ii) MOLECULE TYPE: DNA (primer)

(xi) SEQUENCE DESCRIPTION: SEQ ID NO:12:

TAAWGGWCCA GARTCTCCTT GACA                                                    24

(2) INFORMATION FOR SEQ ID NO:13:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (primer)

(xi) SEQUENCE DESCRIPTION: SEQ ID NO:13:

GGAAACAGCT ATGACCATG                                                          19

(2) INFORMATION FOR SEQ ID NO:14:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (primer)

(xi) SEQUENCE DESCRIPTION: SEQ ID NO:14:

ATTAACCCTC ACTAAAG                                                            17

(2) INFORMATION FOR SEQ ID NO:15:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO:15:

TGGGTWGTWA CWGCWGCWCA TTG                                                     23

(2) INFORMATION FOR SEQ ID NO:16:

(i) SEQUENCE CHARACTERISTICS:
            (A) LENGTH: 672 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: CDS
            (B) LOCATION: 1..672

(xi) SEQUENCE DESCRIPTION: SEQ ID NO:16:

GCA CGA GAT CGC ATT GTT GGA GGA TTG GAG GCG AAA AAT GGA TCA GCC               48
Ala Arg Asp Arg Ile Val Gly Gly Leu Glu Ala Lys Asn Gly Ser Ala
 1               5                  10                  15

CCA TTC ATG GTT TCT TTG CAA GCG GAA GAC TAT TTT CAT TTT TGT GGA               96
Pro Phe Met Val Ser Leu Gln Ala Glu Asp Tyr Phe His Phe Cys Gly

```
                    20                    25                    30
TCC TCT ATT CTG AAT GAG AGA TGG GTT CTT ACT GCT GCT CAC TGT ATC          144
Ser Ser Ile Leu Asn Glu Arg Trp Val Leu Thr Ala Ala His Cys Ile
            35                    40                    45

CAA CCA AAT GTA CAC AAG TAC GTT TAC GTC GGT TCG AAC AAC GTA GAA          192
Gln Pro Asn Val His Lys Tyr Val Tyr Val Gly Ser Asn Asn Val Glu
    50                    55                    60

GTA GGC GGA ACA CAC TAC GAA ATC GAA AAA GCT TTC TAT CAC GAA GAA          240
Val Gly Gly Thr His Tyr Glu Ile Glu Lys Ala Phe Tyr His Glu Glu
65                    70                    75                    80

TAT GAT GGA GTA GAT CTT GTA GAT CAT GAT GTG ATT GAT CAA AGT GAG          288
Tyr Asp Gly Val Asp Leu Val Asp His Asp Val Ile Asp Gln Ser Glu
                    85                    90                    95

ACA AAC ATT GAT TTA ATG AAG TGT CAA CCC ATT AAA TTA CGA AGA AAG          336
Thr Asn Ile Asp Leu Met Lys Cys Gln Pro Ile Lys Leu Arg Arg Lys
            100                   105                   110

CCA CTC GTT GGT GGT GAG GAA TTG AGA GCA GTA GGC TGG GGA AAT ACA          384
Pro Leu Val Gly Gly Glu Glu Leu Arg Ala Val Gly Trp Gly Asn Thr
    115                   120                   125

AAT TCA GCA GGG GAA AAT TTT CCA TTG AAA CTT CAA GAA TTG TAC GTG          432
Asn Ser Ala Gly Glu Asn Phe Pro Leu Lys Leu Gln Glu Leu Tyr Val
130                   135                   140

AAA GCT TTG ACT AAT GAG GAG TGC AAA GCT AAA TCA CCA ATT CCA CCA          480
Lys Ala Leu Thr Asn Glu Glu Cys Lys Ala Lys Ser Pro Ile Pro Pro
145                   150                   155                   160

ACG ACC CAA GTC TGC ACA CTT TTG GAA AAG AAT CAT GGT GTA TGC TCG          528
Thr Thr Gln Val Cys Thr Leu Leu Glu Lys Asn His Gly Val Cys Ser
                    165                   170                   175

GGA GAT TCT GGT GGT CCA TTG CTT TTG GAT GGC GAG CAA GTT GGC ATT          576
Gly Asp Ser Gly Gly Pro Leu Leu Leu Asp Gly Glu Gln Val Gly Ile
            180                   185                   190

GCC TCA TTT GTT ATC TTC AAA TGC GCA ATG GGG TAC CCT GAC TAT TTC          624
Ala Ser Phe Val Ile Phe Lys Cys Ala Met Gly Tyr Pro Asp Tyr Phe
    195                   200                   205

ACA AGA TTG TCT CTA TAT GTA GAT TGG ATT GAA CAA CAC ATG GAT TAA          672
Thr Arg Leu Ser Leu Tyr Val Asp Trp Ile Glu Gln His Met Asp  *
210                   215                   220
```

(2) INFORMATION FOR SEQ ID NO:17:

(i) SEQUENCE CHARACTERISTICS:
        (A) LENGTH: 223 amino acids
        (B) TYPE: amino acid
        (D) TOPOLOGY: linear (ii) MOLECULE TYPE: protein (xi) SEQUENCE DESCRIPTION: SEQ ID NO:17:

```
Ala Arg Asp Arg Ile Val Gly Gly Leu Glu Ala Lys Asn Gly Ser Ala
1               5                   10                  15

Pro Phe Met Val Ser Leu Gln Ala Glu Asp Tyr Phe His Phe Cys Gly
            20                  25                  30

Ser Ser Ile Leu Asn Glu Arg Trp Val Leu Thr Ala Ala His Cys Ile
        35                  40                  45

Gln Pro Asn Val His Lys Tyr Val Tyr Val Gly Ser Asn Asn Val Glu
    50                  55                  60

Val Gly Gly Thr His Tyr Glu Ile Glu Lys Ala Phe Tyr His Glu Glu
65                  70                  75                  80

Tyr Asp Gly Val Asp Leu Val Asp His Asp Val Ile Asp Gln Ser Glu
                85                  90                  95
```

```
Thr Asn Ile Asp Leu Met Lys Cys Gln Pro Ile Lys Leu Arg Arg Lys
            100                 105                 110

Pro Leu Val Gly Gly Glu Glu Leu Arg Ala Val Gly Trp Gly Asn Thr
        115                 120                 125

Asn Ser Ala Gly Glu Asn Phe Pro Leu Lys Leu Gln Glu Leu Tyr Val
        130                 135                 140

Lys Ala Leu Thr Asn Glu Glu Cys Lys Ala Lys Ser Pro Ile Pro Pro
145                 150                 155                 160

Thr Thr Gln Val Cys Thr Leu Leu Glu Lys Asn His Gly Val Cys Ser
                165                 170                 175

Gly Asp Ser Gly Gly Pro Leu Leu Asp Gly Glu Gln Val Gly Ile
                180                 185                 190

Ala Ser Phe Val Ile Phe Lys Cys Ala Met Gly Tyr Pro Asp Tyr Phe
        195                 200                 205

Thr Arg Leu Ser Leu Tyr Val Asp Trp Ile Glu Gln His Met Asp
        210                 215                 220
```

(2) INFORMATION FOR SEQ ID NO:18:

(i) SEQUENCE CHARACTERISTICS:
        (A) LENGTH: 156 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..156

(xi) SEQUENCE DESCRIPTION: SEQ ID NO:18:

```
GGG TGG GGA AGA CTT GGA GCT AAC TTG AAT GGA CCG AAT GAA CTC CAA      48
Gly Trp Gly Arg Leu Gly Ala Asn Leu Asn Gly Pro Asn Glu Leu Gln
 1               5                  10                  15

GAA CTT AAC ACT GTC ACA TTA AGC CAC CAG CAA TGT GTA AGA CAA CAA      96
Glu Leu Asn Thr Val Thr Leu Ser His Gln Gln Cys Val Arg Gln Gln
                20                  25                  30

ATT TAT CCA GTA TAC GAC AGC CAA CTT TGC ACA TTT GTT GGC AGT GGA     144
Ile Tyr Pro Val Tyr Asp Ser Gln Leu Cys Thr Phe Val Gly Ser Gly
            35                  40                  45

CGA GGC GCC TGC                                                      156
Arg Gly Ala Cys
        50
```

(2) INFORMATION FOR SEQ ID NO:19:

(i) SEQUENCE CHARACTERISTICS:
        (A) LENGTH: 52 amino acids
        (B) TYPE: amino acid
        (D) TOPOLOGY: linear (ii) MOLECULE TYPE: protein (xi) SEQUENCE DESCRIPTION: SEQ ID NO:19:

```
Gly Trp Gly Arg Leu Gly Ala Asn Leu Asn Gly Pro Asn Glu Leu Gln
 1               5                  10                  15

Glu Leu Asn Thr Val Thr Leu Ser His Gln Gln Cys Val Arg Gln Gln
                20                  25                  30

Ile Tyr Pro Val Tyr Asp Ser Gln Leu Cys Thr Phe Val Gly Ser Gly
            35                  40                  45
```

Arg Gly Ala Cys
    50

(2) INFORMATION FOR SEQ ID NO:20:

(i) SEQUENCE CHARACTERISTICS:
        (A) LENGTH: 168 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..168

(xi) SEQUENCE DESCRIPTION: SEQ ID NO:20:

```
GGA TGG GGC AAA TTA AGT GAA TCA GGA CCC AAG CCA GTA AAT CTA CAA        48
Gly Trp Gly Lys Leu Ser Glu Ser Gly Pro Lys Pro Val Asn Leu Gln
 1               5                  10                  15

GGA GTA AAA GTG CCT TAT GTG ACC AAG ATA CAT GCT CTG ACA GCT ACG        96
Gly Val Lys Val Pro Tyr Val Thr Lys Ile His Ala Leu Thr Ala Thr
             20                  25                  30

TCT TTG CAG GTA AAA GAT ATC ACC GAA AAC ATG TTG TGT GCC GGA GTT       144
Ser Leu Gln Val Lys Asp Ile Thr Glu Asn Met Leu Cys Ala Gly Val
         35                  40                  45

AGA AGA GGT GGC AAG GAC TCC TGC                                       168
Arg Arg Gly Gly Lys Asp Ser Cys
 50                  55
```

(2) INFORMATION FOR SEQ ID NO:21:

(i) SEQUENCE CHARACTERISTICS:
        (A) LENGTH: 56 amino acids
        (B) TYPE: amino acid
        (D) TOPOLOGY: linear (ii) MOLECULE TYPE: protein (xi) SEQUENCE DESCRIPTION: SEQ ID NO:21:

```
Gly Trp Gly Lys Leu Ser Glu Ser Gly Pro Lys Pro Val Asn Leu Gln
 1               5                  10                  15

Gly Val Lys Val Pro Tyr Val Thr Lys Ile His Ala Leu Thr Ala Thr
             20                  25                  30

Ser Leu Gln Val Lys Asp Ile Thr Glu Asn Met Leu Cys Ala Gly Val
         35                  40                  45

Arg Arg Gly Gly Lys Asp Ser Cys
 50                  55
```

(2) INFORMATION FOR SEQ ID NO:22:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..177

(xi) SEQUENCE DESCRIPTION: SEQ ID NO:22:

```
GGA TGG GGA TCA AGA TCT ACT TCC AAT TTC CCA TCT TAC CCC AAC CTT        48
Gly Trp Gly Ser Arg Ser Thr Ser Asn Phe Pro Ser Tyr Pro Asn Leu
```

```
      1               5                  10                 15
TTA CAG ACC GTT GAC AAA CCA ATT GTA TCT TAT GCC GAA TGT GAG AAA          96
Leu Gln Thr Val Asp Lys Pro Ile Val Ser Tyr Ala Glu Cys Glu Lys
            20                  25                  30

GTA TTG GGA GGT CCT GGA GCC TCA CCA CTT CAC CCC TTG AAC CTC TGC          144
Val Leu Gly Gly Pro Gly Ala Ser Pro Leu His Pro Leu Asn Leu Cys
        35                  40                  45

ACT GGA CCC TTG ACC GGT GGA GTA AGC GCT TGT                              177
Thr Gly Pro Leu Thr Gly Gly Val Ser Ala Cys
        50                  55
```

(2) INFORMATION FOR SEQ ID NO:23:

(i) SEQUENCE CHARACTERISTICS:
        (A) LENGTH: 59 amino acids
        (B) TYPE: amino acid
        (D) TOPOLOGY: linear (ii) MOLECULE TYPE: protein (xi) SEQUENCE DESCRIPTION: SEQ ID NO:23:

```
Gly Trp Gly Ser Arg Ser Thr Ser Asn Phe Pro Ser Tyr Pro Asn Leu
 1               5                  10                  15

Leu Gln Thr Val Asp Lys Pro Ile Val Ser Tyr Ala Glu Cys Glu Lys
            20                  25                  30

Val Leu Gly Gly Pro Gly Ala Ser Pro Leu His Pro Leu Asn Leu Cys
        35                  40                  45

Thr Gly Pro Leu Thr Gly Gly Val Ser Ala Cys
        50                  55
```

(2) INFORMATION FOR SEQ ID NO:24:

(i) SEQUENCE CHARACTERISTICS:
        (A) LENGTH: 156 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..156

(xi) SEQUENCE DESCRIPTION: SEQ ID NO:24:

```
GGC TGG GGA AAT ACA AAT TCA GCA GGG GAA AAT TTT CCA TTG AAA CTT          48
Gly Trp Gly Asn Thr Asn Ser Ala Gly Glu Asn Phe Pro Leu Lys Leu
 1               5                  10                  15

CAA GAA TTG TAC GTG AAA GCT TTG ACT AAT GAG GAG TGC AAA GCT AAA          96
Gln Glu Leu Tyr Val Lys Ala Leu Thr Asn Glu Glu Cys Lys Ala Lys
            20                  25                  30

TCA CCA ATT CCA CCA ACG ACC CAA GTC TGC ACA CTT TTG GAA AAG AAT          144
Ser Pro Ile Pro Pro Thr Thr Gln Val Cys Thr Leu Leu Glu Lys Asn
        35                  40                  45

CAT GGT GTA TGC                                                          156
His Gly Val Cys
        50
```

(2) INFORMATION FOR SEQ ID NO:25:

(i) SEQUENCE CHARACTERISTICS:
        (A) LENGTH: 52 amino acids
        (B) TYPE: amino acid
        (D) TOPOLOGY: linear (ii) MOLECULE TYPE: protein (xi) SEQUENCE DESCRIPTION: SEQ ID NO:25:

Gly Trp Gly Asn Thr Asn Ser Ala Gly Glu Asn Phe Pro Leu Lys Leu
  1               5                  10                  15

Gln Glu Leu Tyr Val Lys Ala Leu Thr Asn Glu Glu Cys Lys Ala Lys
                 20                  25                  30

Ser Pro Ile Pro Pro Thr Thr Gln Val Cys Thr Leu Leu Glu Lys Asn
             35                  40                  45

His Gly Val Cys
         50

(2) INFORMATION FOR SEQ ID NO:26:

(i) SEQUENCE CHARACTERISTICS:
        (A) LENGTH: 159 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..159

(xi) SEQUENCE DESCRIPTION: SEQ ID NO:26:

GGA TGG GGA TCA ACT GGA TCT GGT GGT CCA ATT ACA AAT GTT CTA CAA      48
Gly Trp Gly Ser Thr Gly Ser Gly Gly Pro Ile Thr Asn Val Leu Gln
  1               5                  10                  15

GAA GTC GAA GTT CCA TTT ATC GAC TTC AAC ACC TGC CGA AAA TCC TAC      96
Glu Val Glu Val Pro Phe Ile Asp Phe Asn Thr Cys Arg Lys Ser Tyr
                 20                  25                  30

TCA ACC AGC TTA ACC GAC CGT ATG TTC TGC GCT GGA TTT TTG GGA ATT     144
Ser Thr Ser Leu Thr Asp Arg Met Phe Cys Ala Gly Phe Leu Gly Ile
             35                  40                  45

GGT GGT AAG GCT TGC                                                  159
Gly Gly Lys Ala Cys
         50

(2) INFORMATION FOR SEQ ID NO:27:

(i) SEQUENCE CHARACTERISTICS:
        (A) LENGTH: 53 amino acids
        (B) TYPE: amino acid
        (D) TOPOLOGY: linear (ii) MOLECULE TYPE: protein (xi) SEQUENCE DESCRIPTION: SEQ ID NO:27:

Gly Trp Gly Ser Thr Gly Ser Gly Gly Pro Ile Thr Asn Val Leu Gln
  1               5                  10                  15

Glu Val Glu Val Pro Phe Ile Asp Phe Asn Thr Cys Arg Lys Ser Tyr
                 20                  25                  30

Ser Thr Ser Leu Thr Asp Arg Met Phe Cys Ala Gly Phe Leu Gly Ile
             35                  40                  45

Gly Gly Lys Ala Cys
         50

(2) INFORMATION FOR SEQ ID NO:28:

(i) SEQUENCE CHARACTERISTICS:
        (A) LENGTH: 168 base pairs
        (B) TYPE: nucleic acid (C) STRANDEDNESS: single
        (D) TOPOLOGY: linear (ii) MOLECULE TYPE: cDNA (ix) FEATURE:
        (A) NAME/KEY: CDS
        (B) LOCATION: 1..168

(xi) SEQUENCE DESCRIPTION: SEQ ID NO:28:

```
GGC TGG GGA AAT TTA GGG GAA GAT GAG GAC GAC CCC GAA CAA CTG CAA      48
Gly Trp Gly Asn Leu Gly Glu Asp Glu Asp Asp Pro Glu Gln Leu Gln
 1               5                  10                  15

TAT GTA AAG GTA CCT ATT GTT AAC TGG ACT CAG TGC AAA ACT ATA TAT      96
Tyr Val Lys Val Pro Ile Val Asn Trp Thr Gln Cys Lys Thr Ile Tyr
            20                  25                  30

GGA AAT GAA GGA CTA ATA ATT ACC CAA AAT ATG ATT TGT GCT GGT TAT     144
Gly Asn Glu Gly Leu Ile Ile Thr Gln Asn Met Ile Cys Ala Gly Tyr
        35                  40                  45

CCT GAT GGC GGT AAG GAC TCT TGC                                     168
Pro Asp Gly Gly Lys Asp Ser Cys
    50                  55
```

(2) INFORMATION FOR SEQ ID NO:29:

(i) SEQUENCE CHARACTERISTICS:
        (A) LENGTH: 56 amino acids
        (B) TYPE: amino acid
        (D) TOPOLOGY: linear (ii) MOLECULE TYPE: protein (xi) SEQUENCE DESCRIPTION: SEQ ID NO:29:

```
Gly Trp Gly Asn Leu Gly Glu Asp Glu Asp Asp Pro Glu Gln Leu Gln
 1               5                  10                  15

Tyr Val Lys Val Pro Ile Val Asn Trp Thr Gln Cys Lys Thr Ile Tyr
            20                  25                  30

Gly Asn Glu Gly Leu Ile Ile Thr Gln Asn Met Ile Cys Ala Gly Tyr
        35                  40                  45

Pro Asp Gly Gly Lys Asp Ser Cys
    50                  55
```

(2) INFORMATION FOR SEQ ID NO:30:

(i) SEQUENCE CHARACTERISTICS:
        (A) LENGTH: 159 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..159

(xi) SEQUENCE DESCRIPTION: SEQ ID NO:30:

```
GGA TGG GCA TCT CCA AAG ATT TCC CCT GCT TTC GAA TTG CCT GAC AAA      48
Gly Trp Ala Ser Pro Lys Ile Ser Pro Ala Phe Glu Leu Pro Asp Lys
 1               5                  10                  15

CTA CAG TAC ACA ACT TTG GAA GTC CAA CCA AGT GAA GAC TGC AAA AAA      96
Leu Gln Tyr Thr Thr Leu Glu Val Gln Pro Ser Glu Asp Cys Lys Lys
            20                  25                  30

GTA TGG GCC CCT TAC ATG CGC GAC TAC ATC CTT TGT GCC AAA TTT GAA     144
Val Trp Ala Pro Tyr Met Arg Asp Tyr Ile Leu Cys Ala Lys Phe Glu
        35                  40                  45
```

```
AAA CAA AAC ATT TGC                                                         159
Lys Gln Asn Ile Cys
     50

(2) INFORMATION FOR SEQ ID NO:31:

(i) SEQUENCE CHARACTERISTICS:
        (A) LENGTH: 53 amino acids
        (B) TYPE: amino acid
        (D) TOPOLOGY: linear (ii) MOLECULE TYPE: protein (xi) SEQUENCE DESCRIPTION: SEQ ID NO:31:

Gly Trp Ala Ser Pro Lys Ile Ser Pro Ala Phe Glu Leu Pro Asp Lys
 1               5                  10                  15

Leu Gln Tyr Thr Thr Leu Glu Val Gln Pro Ser Glu Asp Cys Lys Lys
             20                  25                  30

Val Trp Ala Pro Tyr Met Arg Asp Tyr Ile Leu Cys Ala Lys Phe Glu
             35                  40                  45

Lys Gln Asn Ile Cys
     50

(2) INFORMATION FOR SEQ ID NO:32:

(i) SEQUENCE CHARACTERISTICS:
        (A) LENGTH: 186 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..186

(xi) SEQUENCE DESCRIPTION: SEQ ID NO:32:

GGT TGG GGA AAG ATA GAC TAT TCT GAG AGC AGA AGT GAT GAC CTA CTG        48
Gly Trp Gly Lys Ile Asp Tyr Ser Glu Ser Arg Ser Asp Asp Leu Leu
 1               5                  10                  15

AAA GTA GTA CTG AAA ATT ATT GAT AAT AGG CAA TGC GVY CCC TTA TAC        96
Lys Val Val Leu Lys Ile Ile Asp Asn Arg Gln Cys Xaa Pro Leu Tyr
             20                  25                  30

GTT GAT CAG ATT AAT AGA AGA AGA TTG AGA AAT GGA ATT GTA GAA ACA       144
Val Asp Gln Ile Asn Arg Arg Arg Leu Arg Asn Gly Ile Val Glu Thr
             35                  40                  45

CAG ATG TGT GCA GGA GAA TTG GAT GGT GGA AAA GAC ACT TGC               186
Gln Met Cys Ala Gly Glu Leu Asp Gly Gly Lys Asp Thr Cys
     50                  55                  60

(2) INFORMATION FOR SEQ ID NO:33:

(i) SEQUENCE CHARACTERISTICS:
        (A) LENGTH: 62 amino acids
        (B) TYPE: amino acid
        (D) TOPOLOGY: linear (ii) MOLECULE TYPE: protein (ix) FEATURE:
        (A) NAME/KEY: Xaa = Val, Ala, Asp, Glu or Gly
        (B) LOCATION: 29

(xi) SEQUENCE DESCRIPTION: SEQ ID NO:33:

Gly Trp Gly Lys Ile Asp Tyr Ser Glu Ser Arg Ser Asp Asp Leu Leu
```

```
              1               5                  10                 15
            Lys Val Val Leu Lys Ile Ile Asp Asn Arg Gln Cys Xaa Pro Leu Tyr
                              20                  25                  30

Val Asp Gln Ile Asn Arg Arg Arg Leu Arg Asn Gly Ile Val Glu Thr
                              35                  40                  45

Gln Met Cys Ala Gly Glu Leu Asp Gly Gly Lys Asp Thr Cys
                     50                  55                  60
```

(2) INFORMATION FOR SEQ ID NO:34:

(i) SEQUENCE CHARACTERISTICS:
        (A) LENGTH: 168 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..168

(xi) SEQUENCE DESCRIPTION: SEQ ID NO:34:

```
GGA TGG GGA AGA ACA TCG TTC GGT GGC CAA TTG TCT AAA AAT CTG CGA    48
Gly Trp Gly Arg Thr Ser Phe Gly Gly Gln Leu Ser Lys Asn Leu Arg
 1               5                  10                  15

GGA GTC GAG TTG GAA ATA ATA GAT CTA TTC GAT TGT TTC CTT TCC TAC    96
Gly Val Glu Leu Glu Ile Ile Asp Leu Phe Asp Cys Phe Leu Ser Tyr
                 20                  25                  30

ATG GAT AAA GTA AAC GTG TCC GAA AGG CAA GTT TGC GCT GGA ATC CCC   144
Met Asp Lys Val Asn Val Ser Glu Arg Gln Val Cys Ala Gly Ile Pro
             35                  40                  45

GTT GTA GGT GGT AAA GAT TCT TGC                                   168
Val Val Gly Gly Lys Asp Ser Cys
         50                  55
```

(2) INFORMATION FOR SEQ ID NO:35:

(i) SEQUENCE CHARACTERISTICS:
        (A) LENGTH: 56 amino acids
        (B) TYPE: amino acid
        (D) TOPOLOGY: linear (ii) MOLECULE TYPE: protein (xi) SEQUENCE DESCRIPTION: SEQ ID NO:35:

```
Gly Trp Gly Arg Thr Ser Phe Gly Gly Gln Leu Ser Lys Asn Leu Arg
 1               5                  10                  15

Gly Val Glu Leu Glu Ile Ile Asp Leu Phe Asp Cys Phe Leu Ser Tyr
                 20                  25                  30

Met Asp Lys Val Asn Val Ser Glu Arg Gln Val Cys Ala Gly Ile Pro
             35                  40                  45

Val Val Gly Gly Lys Asp Ser Cys
         50                  55
```

(2) INFORMATION FOR SEQ ID NO:36:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: cDNA (ix) FEATURE:
    (A) NAME/KEY: CDS
    (B) LOCATION: 1..120

(xi) SEQUENCE DESCRIPTION: SEQ ID NO:36:

| | | | | | | | | | | | | | | | | |
|---|---|---|---|---|---|---|---|---|---|---|---|---|---|---|---|---|
|GGA|TGG|GGT|GCA|GTC|TAC|GAA|GGA|GGT|GCA|GGA|TCC|ACC|CAA|TTA|CTA|48|
|Gly|Trp|Gly|Ala|Val|Tyr|Glu|Gly|Gly|Ala|Gly|Ser|Thr|Gln|Leu|Leu| |
|1| | | |5| | | | |10| | | | |15| | |

| | | | | | | | | | | | | | | | | |
|---|---|---|---|---|---|---|---|---|---|---|---|---|---|---|---|---|
|TAC|TCC|CAA|TTT|GGC|GGT|GTT|GCT|CCT|AGC|ATG|ATC|TGC|GCT|GGA|TTT|96|
|Tyr|Ser|Gln|Phe|Gly|Gly|Val|Ala|Pro|Ser|Met|Ile|Cys|Ala|Gly|Phe| |
| | | | |20| | | | |25| | | | |30| | |

| | | | | | | | |
|---|---|---|---|---|---|---|---|---|
|GAC|CAA|GGC|GGT|AAG|GAC|GCT|TGT|120|
|Asp|Gln|Gly|Gly|Lys|Asp|Ala|Cys| |
| | | |35| | | |40| |

(2) INFORMATION FOR SEQ ID NO:37:

(i) SEQUENCE CHARACTERISTICS:
        (A) LENGTH: 40 amino acids
        (B) TYPE: amino acid
        (D) TOPOLOGY: linear (ii) MOLECULE TYPE: protein (xi) SEQUENCE DESCRIPTION: SEQ ID NO:37:

Gly Trp Gly Ala Val Tyr Glu Gly Gly Ala Gly Ser Thr Gln Leu Leu
 1               5                  10                  15

Tyr Ser Gln Phe Gly Gly Val Ala Pro Ser Met Ile Cys Ala Gly Phe
                20                  25                  30

Asp Gln Gly Gly Lys Asp Ala Cys
            35              40

(2) INFORMATION FOR SEQ ID NO:38:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..162

(xi) SEQUENCE DESCRIPTION: SEQ ID NO:38:

| | | | | | | | | | | | | | | | | |
|---|---|---|---|---|---|---|---|---|---|---|---|---|---|---|---|---|
|GGT|TGG|GGA|ACT|ACA|GAG|AGT|ACT|GAA|TCA|TCA|CAC|CAC|CTG|AAA|GAA|48|
|Gly|Trp|Gly|Thr|Thr|Glu|Ser|Thr|Glu|Ser|Ser|His|His|Leu|Lys|Glu| |
|1| | | |5| | | | |10| | | | |15| | |

| | | | | | | | | | | | | | | | | |
|---|---|---|---|---|---|---|---|---|---|---|---|---|---|---|---|---|
|GTT|GAA|GTG|AAC|GCT|GTA|TCT|AAT|AGT|GAA|TGT|CAA|AGG|CCT|AAT|GAA|96|
|Val|Glu|Val|Asn|Ala|Val|Ser|Asn|Ser|Glu|Cys|Gln|Arg|Pro|Asn|Glu| |
| | | | |20| | | | |25| | | | |30| | |

| | | | | | | | | | | | | | | | | |
|---|---|---|---|---|---|---|---|---|---|---|---|---|---|---|---|---|
|GAT|CTT|GCT|ACT|ATA|TCA|TCA|CAT|GAG|ATA|TGT|GCA|AGC|GTT|CCT|GGT|144|
|Asp|Leu|Ala|Thr|Ile|Ser|Ser|His|Glu|Ile|Cys|Ala|Ser|Val|Pro|Gly| |
| | | | |35| | | | |40| | | | |45| | |

| | | | | | |
|---|---|---|---|---|---|
|GGC|GGC|AAA|GAT|TCT|TGT|162|
|Gly|Gly|Lys|Asp|Ser|Cys| |
| |50| | | | | |

(2) INFORMATION FOR SEQ ID NO:39:

(i) SEQUENCE CHARACTERISTICS:
        (A) LENGTH: 54 amino acids
        (B) TYPE: amino acid
        (D) TOPOLOGY: linear (ii) MOLECULE TYPE: protein (xi) SEQUENCE DESCRIPTION: SEQ ID NO:39:

Gly Trp Gly Thr Thr Glu Ser Thr Glu Ser Ser His His Leu Lys Glu
1               5                   10                  15

Val Glu Val Asn Ala Val Ser Asn Ser Glu Cys Gln Arg Pro Asn Glu
                20                  25                  30

Asp Leu Ala Thr Ile Ser Ser His Glu Ile Cys Ala Ser Val Pro Gly
            35                  40                  45

Gly Gly Lys Asp Ser Cys
        50

(2) INFORMATION FOR SEQ ID NO:40:

(i) SEQUENCE CHARACTERISTICS:
        (A) LENGTH: 40 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:40:

Ile Val Gly Gly Glu Asn Ala Lys Glu Lys Ser Asp Val Pro Tyr Gln
1               5                   10                  15

Val Ser Leu Arg Asn Ala Glu Asn Lys His Phe Cys Gly Gly Ala Ile
                20                  25                  30

Ile Asp Asp Tyr Trp Val Leu Thr
            35                  40

(2) INFORMATION FOR SEQ ID NO:41:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:41:

Ile Val Gly Gly Leu Glu Ala Lys Asn Gly Ser Ala Pro Phe Met Val
1               5                   10                  15

Ser Leu Gln Ala Glu Asp Tyr Phe His
                20                  25

(2) INFORMATION FOR SEQ ID NO:42:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:42:

Ile Ile Gly Gly Glu Val Ala Gly Glu Gly Ser Ala Pro Tyr Gln Val
1               5                   10                  15

Ser Leu Arg Thr Lys Glu Gly Asn His Phe
                20                  25

(2) INFORMATION FOR SEQ ID NO:43:

(i) SEQUENCE CHARACTERISTICS:
            (A) LENGTH: 29 amino acids
            (B) TYPE: amino acid
            (C) STRANDEDNESS:
            (D) TOPOLOGY: linear (ii) MOLECULE TYPE: protein (xi) SEQUENCE DESCRIPTION: SEQ ID NO:43:

Ile Val Gly Gly Thr Ala Val Asp Ile Arg Gly Phe Pro Gly Arg Tyr
1               5                  10                  15

Gln Phe Lys Pro Lys Pro Ser Phe Leu Trp Trp Phe Tyr
            20                  25

(2) INFORMATION FOR SEQ ID NO:44:

(i) SEQUENCE CHARACTERISTICS:
            (A) LENGTH: 35 amino acids
            (B) TYPE: amino acid
            (C) STRANDEDNESS:
            (D) TOPOLOGY: linear (ii) MOLECULE TYPE: protein (xi) SEQUENCE DESCRIPTION: SEQ ID NO:44:

Ile Val Asn Gly Leu Glu Ala Gly Val Gly Gln Phe Pro Ile Gln Val
1               5                  10                  15

Phe Leu Asp Leu Thr Asn Ile Arg Asp Glu Lys Ser Arg Cys Gly Gly
            20                  25                  30

Ala Leu Phe
        35

(2) INFORMATION FOR SEQ ID NO:45:

(i) SEQUENCE CHARACTERISTICS:
            (A) LENGTH: 24 amino acids
            (B) TYPE: amino acid
            (C) STRANDEDNESS:
            (D) TOPOLOGY: linear (ii) MOLECULE TYPE: protein (xi) SEQUENCE DESCRIPTION: SEQ ID NO:45:

Ile Val Gly Gly Leu Glu Ala Lys Asn Gly Ile Thr Pro Phe Ile Gly
1               5                  10                  15

Phe Phe Ala Ser Gly Arg Leu Phe
            20

(2) INFORMATION FOR SEQ ID NO:46:

(i) SEQUENCE CHARACTERISTICS:
            (A) LENGTH: 26 amino acids
            (B) TYPE: amino acid
            (C) STRANDEDNESS:
            (D) TOPOLOGY: linear (ii) MOLECULE TYPE: protein (xi) SEQUENCE DESCRIPTION: SEQ ID NO:46:

Ile Val Gly Gly Asn Asp Val Ser Xaa Lys Ile Phe Trp Gln Val Ser
1               5                  10                  15

Ile Gln Ser Asn Xaa Gln His Phe Cys Gly
            20                  25

(2) INFORMATION FOR SEQ ID NO:47:

```
        (i) SEQUENCE CHARACTERISTICS:
            (A) LENGTH: 31 amino acids
            (B) TYPE: amino acid
            (C) STRANDEDNESS:
            (D) TOPOLOGY: linear (ii) MOLECULE TYPE: protein (xi) SEQUENCE DESCRIPTION: SEQ ID NO:47:

Ile Ile Gly Gly Glu Asp Ala Pro Glu Gly Ser Ala Pro Tyr Gln Val
1               5                  10                  15

Ser Leu Arg Asn Gln Asn Leu Glu His Phe Cys Gly Gly Ser Ile
            20                  25                  30

(2) INFORMATION FOR SEQ ID NO:48:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (primer)

(xi) SEQUENCE DESCRIPTION: SEQ ID NO:48:

GTWGGWAAAG GWWTWACWTT YGATTCWGGW GG                              32

(2) INFORMATION FOR SEQ ID NO:49:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (primer)

(xi) SEQUENCE DESCRIPTION: SEQ ID NO:49:

CGWCCTTCWG CATCWGTATT                                            20

(2) INFORMATION FOR SEQ ID NO:50:

(i) SEQUENCE CHARACTERISTICS:
            (A) LENGTH: 453 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: CDS
            (B) LOCATION: 1..453

(xi) SEQUENCE DESCRIPTION: SEQ ID NO:50:

CAC GAG TTT TGT GCG AGT GTC AGA TAT TGC AGC TCT ATG AGT AAC AAG    48
His Glu Phe Cys Ala Ser Val Arg Tyr Cys Ser Ser Met Ser Asn Lys
 1               5                  10                  15

AAA GGA TTA GTA CTG GGC ATC TAC GAC AAT GAA TTC GAT AAA AAA ATA    96
Lys Gly Leu Val Leu Gly Ile Tyr Asp Asn Glu Phe Asp Lys Lys Ile
            20                  25                  30

AGG TTA ACG CCA ACT GCT GAA CAA TTC AAT CGG CGA TTG CAG GGG CGT   144
Arg Leu Thr Pro Thr Ala Glu Gln Phe Asn Arg Arg Leu Gln Gly Arg
        35                  40                  45

TTA CTA GAT CTA ATT CAT TTG AGT GGA CCC ATT AAA TTG GGC AAG AGC   192
Leu Leu Asp Leu Ile His Leu Ser Gly Pro Ile Lys Leu Gly Lys Ser
    50                  55                  60
```

```
CGT ATT TTC TGG GAT CTC GAT GAA TTC GGC GCA GTT GCA GTT GCA GGT        240
Arg Ile Phe Trp Asp Leu Asp Glu Phe Gly Ala Val Ala Val Ala Gly
 65              70                  75                  80

TTG GGA AAT CAC TCC CCC TGC GAA CTC CTG GAA GAA CTC GAT GTT TTG        288
Leu Gly Asn His Ser Pro Cys Glu Leu Leu Glu Glu Leu Asp Val Leu
             85                  90                  95

CGC GAA AAT GCC AGA ATA GCT GCC GGT GCT GGT TGC CAA GCT CTT GCC        336
Arg Glu Asn Ala Arg Ile Ala Ala Gly Ala Gly Cys Gln Ala Leu Ala
            100                 105                 110

GCC GAT GGA ATC ACT ACC ATT AGC GTT GAA GTA TGG AGC ACC CGG AGG        384
Ala Asp Gly Ile Thr Thr Ile Ser Val Glu Val Trp Ser Thr Arg Arg
        115                 120                 125

CGG CCA TGC GAA GGT GCA ATA CTA TCG ACG TTC AAA TTC AGG TCA ACA        432
Arg Pro Cys Glu Gly Ala Ile Leu Ser Thr Phe Lys Phe Arg Ser Thr
    130                 135                 140

GAA GTA GTC CAG TGT AGC GGT                                            453
Glu Val Val Gln Cys Ser Gly
145             150
```

(2) INFORMATION FOR SEQ ID NO:51:

(i) SEQUENCE CHARACTERISTICS:
        (A) LENGTH: 151 amino acids
        (B) TYPE: amino acid
        (D) TOPOLOGY: linear (ii) MOLECULE TYPE: protein (xi) SEQUENCE DESCRIPTION: SEQ ID NO:51:

```
His Glu Phe Cys Ala Ser Val Arg Tyr Cys Ser Ser Met Ser Asn Lys
 1               5                  10                  15

Lys Gly Leu Val Leu Gly Ile Tyr Asp Asn Glu Phe Asp Lys Lys Ile
             20                  25                  30

Arg Leu Thr Pro Thr Ala Glu Gln Phe Asn Arg Arg Leu Gln Gly Arg
         35                  40                  45

Leu Leu Asp Leu Ile His Leu Ser Gly Pro Ile Lys Leu Gly Lys Ser
     50                  55                  60

Arg Ile Phe Trp Asp Leu Asp Glu Phe Gly Ala Val Ala Val Ala Gly
 65              70                  75                  80

Leu Gly Asn His Ser Pro Cys Glu Leu Leu Glu Glu Leu Asp Val Leu
             85                  90                  95

Arg Glu Asn Ala Arg Ile Ala Ala Gly Ala Gly Cys Gln Ala Leu Ala
            100                 105                 110

Ala Asp Gly Ile Thr Thr Ile Ser Val Glu Val Trp Ser Thr Arg Arg
        115                 120                 125

Arg Pro Cys Glu Gly Ala Ile Leu Ser Thr Phe Lys Phe Arg Ser Thr
    130                 135                 140

Glu Val Val Gln Cys Ser Gly
145             150
```

(2) INFORMATION FOR SEQ ID NO:52:

(i) SEQUENCE CHARACTERISTICS:
        (A) LENGTH: 258 base pairs
        (B) TYPE: nucleic acid
        (C) STRANDEDNESS: single
        (D) TOPOLOGY: linear (ii) MOLECULE TYPE: cDNA (ix) FEATURE:

```
            (A) NAME/KEY: CDS
            (B) LOCATION: 1..258

(xi) SEQUENCE DESCRIPTION: SEQ ID NO:52:

TCA GCA CTC GTT GCC TTG TCT GCA GCT ATT CCT CAC TCC AAC AGA GTC        48
Ser Ala Leu Val Ala Leu Ser Ala Ala Ile Pro His Ser Asn Arg Val
 1               5                  10                  15

GTT GGA GGA CTG GAA GCT GCA GAG GGT TCT GCA CCT TAT CAA GTA TCC        96
Val Gly Gly Leu Glu Ala Ala Glu Gly Ser Ala Pro Tyr Gln Val Ser
                20                  25                  30

TTG CAA GTT GGC AAC TTC CAC TTC TGT GGT GGT TCA ATT CTG AAC GAA       144
Leu Gln Val Gly Asn Phe His Phe Cys Gly Gly Ser Ile Leu Asn Glu
            35                  40                  45

TAT TGG GTT TTG ACT GCT GCT CAC TGT TTG GGT TAT GAC TTC GAC GTG       192
Tyr Trp Val Leu Thr Ala Ala His Cys Leu Gly Tyr Asp Phe Asp Val
        50                  55                  60

GTA GTT GGA ACA AAC AAA CTT GAT CAA CCA GGT GAA AGA TAC CTC GTA       240
Val Val Gly Thr Asn Lys Leu Asp Gln Pro Gly Glu Arg Tyr Leu Val
 65                 70                  75                  80

GAA CAA ACT TTT GTT CAC                                                258
Glu Gln Thr Phe Val His
                85

(2) INFORMATION FOR SEQ ID NO:53:

(i) SEQUENCE CHARACTERISTICS:
        (A) LENGTH: 86 amino acids
        (B) TYPE: amino acid
        (D) TOPOLOGY: linear (ii) MOLECULE TYPE: protein (xi) SEQUENCE DESCRIPTION: SEQ ID NO:53:

Ser Ala Leu Val Ala Leu Ser Ala Ala Ile Pro His Ser Asn Arg Val
 1               5                  10                  15

Val Gly Gly Leu Glu Ala Ala Glu Gly Ser Ala Pro Tyr Gln Val Ser
                20                  25                  30

Leu Gln Val Gly Asn Phe His Phe Cys Gly Gly Ser Ile Leu Asn Glu
            35                  40                  45

Tyr Trp Val Leu Thr Ala Ala His Cys Leu Gly Tyr Asp Phe Asp Val
        50                  55                  60

Val Val Gly Thr Asn Lys Leu Asp Gln Pro Gly Glu Arg Tyr Leu Val
 65                 70                  75                  80

Glu Gln Thr Phe Val His
                85

(2) INFORMATION FOR SEQ ID NO:54:

(i) SEQUENCE CHARACTERISTICS:
        (A) LENGTH: 240 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..240

(xi) SEQUENCE DESCRIPTION: SEQ ID NO:54:

TTA GAT GGG CGC ATT GTT GGA GGA CAA GAT GCT GAT ATT GCC AAA TAT        48
Leu Asp Gly Arg Ile Val Gly Gly Gln Asp Ala Asp Ile Ala Lys Tyr
 1               5                  10                  15
```

```
GGC TAT CAA GCT TCA CTC CAA GTA TTT AAC GAA CAT TTC TGT GGA GCT      96
Gly Tyr Gln Ala Ser Leu Gln Val Phe Asn Glu His Phe Cys Gly Ala
             20                  25                  30

TCA ATA TTG AAT AAT TAT TGG ATT GTC ACA GCA GCT CAT TGC ATA TAT     144
Ser Ile Leu Asn Asn Tyr Trp Ile Val Thr Ala Ala His Cys Ile Tyr
             35                  40                  45

GAT GAA TTC ACG TAT TCA GTT CGA GTC GGC ACC AGT TTC CAA GGA AGA     192
Asp Glu Phe Thr Tyr Ser Val Arg Val Gly Thr Ser Phe Gln Gly Arg
 50                  55                  60

CGT GGT TCC GTT CAT CCT GTG GCA CAA ATT ATC AAG CAT CCT GCA TAC     240
Arg Gly Ser Val His Pro Val Ala Gln Ile Ile Lys His Pro Ala Tyr
 65                  70                  75                  80
```

(2) INFORMATION FOR SEQ ID NO:55:

(i) SEQUENCE CHARACTERISTICS:
        (A) LENGTH: 80 amino acids
        (B) TYPE: amino acid
        (D) TOPOLOGY: linear (ii) MOLECULE TYPE: protein (xi) SEQUENCE DESCRIPTION: SEQ ID NO:55:

```
Leu Asp Gly Arg Ile Val Gly Gly Gln Asp Ala Asp Ile Ala Lys Tyr
 1                   5                  10                  15

Gly Tyr Gln Ala Ser Leu Gln Val Phe Asn Glu His Phe Cys Gly Ala
             20                  25                  30

Ser Ile Leu Asn Asn Tyr Trp Ile Val Thr Ala Ala His Cys Ile Tyr
             35                  40                  45

Asp Glu Phe Thr Tyr Ser Val Arg Val Gly Thr Ser Phe Gln Gly Arg
 50                  55                  60

Arg Gly Ser Val His Pro Val Ala Gln Ile Ile Lys His Pro Ala Tyr
 65                  70                  75                  80
```

(2) INFORMATION FOR SEQ ID NO:56:

(i) SEQUENCE CHARACTERISTICS:
        (A) LENGTH: 218 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..216

(xi) SEQUENCE DESCRIPTION: SEQ ID NO:56:

```
AGG GAA CAA AAG CTG GAG CTC CAC CGC GGT GCG CCG GCT CTA GAA CTA      48
Arg Glu Gln Lys Leu Glu Leu His Arg Gly Ala Pro Ala Leu Glu Leu
 1                   5                  10                  15

GTG GAT CCC CCG GGT CTG CAG GAA TTG GCA CGA GGA TGT TCT TGG CTG      96
Val Asp Pro Pro Gly Leu Gln Glu Leu Ala Arg Gly Cys Ser Trp Leu
             20                  25                  30

TGT TTA GTA GCT ATT CTT TGT GCA GTG GCT GCT GGG CCT ACT AAT CGC     144
Cys Leu Val Ala Ile Leu Cys Ala Val Ala Ala Gly Pro Thr Asn Arg
             35                  40                  45

ATT GTT GGA GGA TTG GAG GCG AAA AAT GGA ATC ACC CCA TTC ATC GGT     192
Ile Val Gly Gly Leu Glu Ala Lys Asn Gly Ile Thr Pro Phe Ile Gly
 50                  55                  60

TTC TTT GCA AGC GGA AGA CTA TTT CA                                  218
Phe Phe Ala Ser Gly Arg Leu Phe
```

```
                                    65                  70

(2) INFORMATION FOR SEQ ID NO:57:

(i) SEQUENCE CHARACTERISTICS:
        (A) LENGTH: 72 amino acids
        (B) TYPE: amino acid
        (D) TOPOLOGY: linear (ii) MOLECULE TYPE: protein (xi) SEQUENCE DESCRIPTION: SEQ ID NO:57:

Arg Glu Gln Lys Leu Glu Leu His Arg Gly Ala Pro Ala Leu Glu Leu
 1               5                  10                  15

Val Asp Pro Pro Gly Leu Gln Glu Leu Ala Arg Gly Cys Ser Trp Leu
            20                  25                  30

Cys Leu Val Ala Ile Leu Cys Ala Val Ala Ala Gly Pro Thr Asn Arg
        35                  40                  45

Ile Val Gly Gly Leu Glu Ala Lys Asn Gly Ile Thr Pro Phe Ile Gly
    50                  55                  60

Phe Phe Ala Ser Gly Arg Leu Phe
 65                 70

(2) INFORMATION FOR SEQ ID NO:58:

(i) SEQUENCE CHARACTERISTICS:
        (A) LENGTH: 240 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..240

(xi) SEQUENCE DESCRIPTION: SEQ ID NO:58:

ACG AGG TTT CGC TTA GCA ATT GTA TGT GCT CTC GCT GTC TGC ACA TTC      48
Thr Arg Phe Arg Leu Ala Ile Val Cys Ala Leu Ala Val Cys Thr Phe
 1               5                  10                  15

GGT GCC AGT GTT CCA GAA CCA TGG AAA AGA TTA GAT GGT AGA ATC GTA      96
Gly Ala Ser Val Pro Glu Pro Trp Lys Arg Leu Asp Gly Arg Ile Val
            20                  25                  30

GGA GGA CAC GAT ACC AGC ATC GAT AAA CAC CCT CAT CAA GTA TCT TTA     144
Gly Gly His Asp Thr Ser Ile Asp Lys His Pro His Gln Val Ser Leu
        35                  40                  45

TTG TAC TCC AGC CAC AAT TGT GGT GGT TCC TTG ATT GCC AAA AAC TGG     192
Leu Tyr Ser Ser His Asn Cys Gly Gly Ser Leu Ile Ala Lys Asn Trp
    50                  55                  60

GTT TTG ACT GCA GCT CAT TGC ATT GGA GTT AAC AAA TAC AAT GTC CGT     240
Val Leu Thr Ala Ala His Cys Ile Gly Val Asn Lys Tyr Asn Val Arg
 65                 70                  75                  80

(2) INFORMATION FOR SEQ ID NO:59:

(i) SEQUENCE CHARACTERISTICS:
        (A) LENGTH: 80 amino acids
        (B) TYPE: amino acid
        (D) TOPOLOGY: linear (ii) MOLECULE TYPE: protein (xi) SEQUENCE DESCRIPTION: SEQ ID NO:59:

Thr Arg Phe Arg Leu Ala Ile Val Cys Ala Leu Ala Val Cys Thr Phe
```

```
              1               5                  10                 15
           Gly Ala Ser Val Pro Glu Pro Trp Lys Arg Leu Asp Gly Arg Ile Val
                              20                 25              30
           Gly Gly His Asp Thr Ser Ile Asp Lys His Pro His Gln Val Ser Leu
                       35                 40                 45
           Leu Tyr Ser Ser His Asn Cys Gly Gly Ser Leu Ile Ala Lys Asn Trp
                    50                 55                 60
           Val Leu Thr Ala Ala His Cys Ile Gly Val Asn Lys Tyr Asn Val Arg
           65                 70                 75                 80
```

(2) INFORMATION FOR SEQ ID NO:60:

(i) SEQUENCE CHARACTERISTICS:
        (A) LENGTH: 234 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..234

(xi) SEQUENCE DESCRIPTION: SEQ ID NO:60:

```
CCC TCA CTA AAG GGA ACA AAA GCT GGA GCT CCA CCG CGG TGC GCC GCT        48
Pro Ser Leu Lys Gly Thr Lys Ala Gly Ala Pro Pro Arg Cys Ala Ala
 1               5                  10                 15

CTA GAA CTA GTG GAT CCC CCG GGC TGC AGG AAT TCG GCA CGA GCG TTT        96
Leu Glu Leu Val Asp Pro Pro Gly Cys Arg Asn Ser Ala Arg Ala Phe
                20                 25                 30

GGT TGG ATT GAG CGC GTC TCA TCT TAC AAG ATA AAG GAT AGA TTA GAT       144
Gly Trp Ile Glu Arg Val Ser Ser Tyr Lys Ile Lys Asp Arg Leu Asp
             35                 40                 45

GGG CGC ATT GTT GGA GGA CAA GAT GCT GAT ATT GCC AAA TAT GGC TAT       192
Gly Arg Ile Val Gly Gly Gln Asp Ala Asp Ile Ala Lys Tyr Gly Tyr
         50                 55                 60

CAA GCT TCA CTC CAA GTA CTT AAC GAA CAT TTC TGT GGA GCT               234
Gln Ala Ser Leu Gln Val Leu Asn Glu His Phe Cys Gly Ala
 65                 70                 75
```

(2) INFORMATION FOR SEQ ID NO:61:

(i) SEQUENCE CHARACTERISTICS:
        (A) LENGTH: 78 amino acids
        (B) TYPE: amino acid
        (D) TOPOLOGY: linear (ii) MOLECULE TYPE: protein (xi) SEQUENCE DESCRIPTION: SEQ ID NO:61:

```
Pro Ser Leu Lys Gly Thr Lys Ala Gly Ala Pro Pro Arg Cys Ala Ala
 1               5                  10                 15

Leu Glu Leu Val Asp Pro Pro Gly Cys Arg Asn Ser Ala Arg Ala Phe
                20                 25                 30

Gly Trp Ile Glu Arg Val Ser Ser Tyr Lys Ile Lys Asp Arg Leu Asp
             35                 40                 45

Gly Arg Ile Val Gly Gly Gln Asp Ala Asp Ile Ala Lys Tyr Gly Tyr
         50                 55                 60

Gln Ala Ser Leu Gln Val Leu Asn Glu His Phe Cys Gly Ala
 65                 70                 75
```

(2) INFORMATION FOR SEQ ID NO:62:

(i) SEQUENCE CHARACTERISTICS:
        (A) LENGTH: 291 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..291

(xi) SEQUENCE DESCRIPTION: SEQ ID NO:62:

```
GCG GTG ATT GTG TCA TTT GTT CTG GCT TGT GCA TTT TCT GTA CAG GCT       48
Ala Val Ile Val Ser Phe Val Leu Ala Cys Ala Phe Ser Val Gln Ala
 1               5                  10                  15

CTT CCA TCA AGC AGA ATT GTC AAT GGA CTT GAA GCA GGA GTT GGA CAA       96
Leu Pro Ser Ser Arg Ile Val Asn Gly Leu Glu Ala Gly Val Gly Gln
             20                  25                  30

TTT CCA ATT CAG GTT TTC TTA GAC TTG ACA AAT ATC AGA GAC GAA AAA      144
Phe Pro Ile Gln Val Phe Leu Asp Leu Thr Asn Ile Arg Asp Glu Lys
         35                  40                  45

TCC AGA TGT GGT GGT GCT TTG TTA TCA GAT TCA TGG GTT TTG ACT GCT      192
Ser Arg Cys Gly Gly Ala Leu Leu Ser Asp Ser Trp Val Leu Thr Ala
 50                  55                  60

GCT CAT TGT TTT GAT GAT TTG AAG TCT ATG GTA GTG TCC GTT GGT GCT      240
Ala His Cys Phe Asp Asp Leu Lys Ser Met Val Val Ser Val Gly Ala
 65                  70                  75                  80

CAT GAT GTC AGC AAA TCT GAA GAA CCT CAC AGG CAA ACC AGG AAA CCT      288
His Asp Val Ser Lys Ser Glu Glu Pro His Arg Gln Thr Arg Lys Pro
                 85                  90                  95

GAA                                                                  291
Glu
```

(2) INFORMATION FOR SEQ ID NO:63:

(i) SEQUENCE CHARACTERISTICS:
        (A) LENGTH: 97 amino acids
        (B) TYPE: amino acid
        (D) TOPOLOGY: linear (ii) MOLECULE TYPE: protein (xi) SEQUENCE DESCRIPTION: SEQ ID NO:63:

```
Ala Val Ile Val Ser Phe Val Leu Ala Cys Ala Phe Ser Val Gln Ala
 1               5                  10                  15

Leu Pro Ser Ser Arg Ile Val Asn Gly Leu Glu Ala Gly Val Gly Gln
             20                  25                  30

Phe Pro Ile Gln Val Phe Leu Asp Leu Thr Asn Ile Arg Asp Glu Lys
         35                  40                  45

Ser Arg Cys Gly Gly Ala Leu Leu Ser Asp Ser Trp Val Leu Thr Ala
 50                  55                  60

Ala His Cys Phe Asp Asp Leu Lys Ser Met Val Val Ser Val Gly Ala
 65                  70                  75                  80

His Asp Val Ser Lys Ser Glu Glu Pro His Arg Gln Thr Arg Lys Pro
                 85                  90                  95

Glu
```

(2) INFORMATION FOR SEQ ID NO:64:

(i) SEQUENCE CHARACTERISTICS:

```
        (A) LENGTH: 144 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..144

(xi) SEQUENCE DESCRIPTION: SEQ ID NO:64:

GTA CTG ATC GTT TTA GCA GTC ATT GAA TTC GCA TCA GCG TCT TCA ATC      48
Val Leu Ile Val Leu Ala Val Ile Glu Phe Ala Ser Ala Ser Ser Ile
 1               5                  10                  15

GGC TGG AGA ATC GTG GGT GGT GAA AAT GCT AAA GAA AAA TCG GTG CCC      96
Gly Trp Arg Ile Val Gly Gly Glu Asn Ala Lys Glu Lys Ser Val Pro
                20                  25                  30

TAT CAA GTT TCA CTT CGA AAT GCT GAA AAC AAA CAT TTC TGT GGA GGA     144
Tyr Gln Val Ser Leu Arg Asn Ala Glu Asn Lys His Phe Cys Gly Gly
                35                  40                  45

(2) INFORMATION FOR SEQ ID NO:65:

(i) SEQUENCE CHARACTERISTICS:
        (A) LENGTH: 48 amino acids
        (B) TYPE: amino acid
        (D) TOPOLOGY: linear (ii) MOLECULE TYPE: protein (xi) SEQUENCE DESCRIPTION: SEQ ID NO:65:

Val Leu Ile Val Leu Ala Val Ile Glu Phe Ala Ser Ala Ser Ser Ile
 1               5                  10                  15

Gly Trp Arg Ile Val Gly Gly Glu Asn Ala Lys Glu Lys Ser Val Pro
                20                  25                  30

Tyr Gln Val Ser Leu Arg Asn Ala Glu Asn Lys His Phe Cys Gly Gly
                35                  40                  45

(2) INFORMATION FOR SEQ ID NO:66:

(i) SEQUENCE CHARACTERISTICS:
        (A) LENGTH: 390 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..390

(xi) SEQUENCE DESCRIPTION: SEQ ID NO:66:

TTC GGC TTC AAG CTA AGT CAT TTG GTA AGT AAG TAC TGT GCT TGT GCA      48
Phe Gly Phe Lys Leu Ser His Leu Val Ser Lys Tyr Cys Ala Cys Ala
 1               5                  10                  15

TTA GCA TCG GCA CTG AAG TAC TCC ATC GAT CAT GGT CCT CGT ATC ATC      96
Leu Ala Ser Ala Leu Lys Tyr Ser Ile Asp His Gly Pro Arg Ile Ile
                20                  25                  30

GGA GGT GAA GTT GCA GGT GAA GGA TCA GCA CCT TAC CAG GTG TCC TTA     144
Gly Gly Glu Val Ala Gly Glu Gly Ser Ala Pro Tyr Gln Val Ser Leu
                35                  40                  45

AGA ACC AAG GAA GGA AAT CAT TTT TGC GGT GGA TCA ATA CTA AAT AAG     192
Arg Thr Lys Glu Gly Asn His Phe Cys Gly Gly Ser Ile Leu Asn Lys
                50                  55                  60
```

```
CGA TGG GTT GTA ACT GCA GCA CAT TGT CTT GAA CCG GAA ATA TTA GAT        240
Arg Trp Val Val Thr Ala Ala His Cys Leu Glu Pro Glu Ile Leu Asp
 65              70                  75                  80

TCG GTA TAC GTC GGA TCC AAT CAC TTA GAC CGA AAA GGC AGA TAT TAC        288
Ser Val Tyr Val Gly Ser Asn His Leu Asp Arg Lys Gly Arg Tyr Tyr
                 85                  90                  95

GAC GTA GAA CGG TAT ATA ATT CAT GAA AAA TAT ATA GGA GAA CTA AAT        336
Asp Val Glu Arg Tyr Ile Ile His Glu Lys Tyr Ile Gly Glu Leu Asn
                100                 105                 110

AAT TTT TAT GCT GAC ATC GGT CTA ATA AAA CTT GAT GGA AGA CTT AGA        384
Asn Phe Tyr Ala Asp Ile Gly Leu Ile Lys Leu Asp Gly Arg Leu Arg
            115                 120                 125

ATT CAA                                                                390
Ile Gln
    130
```

(2) INFORMATION FOR SEQ ID NO:67:

(i) SEQUENCE CHARACTERISTICS:
        (A) LENGTH: 130 amino acids
        (B) TYPE: amino acid
        (D) TOPOLOGY: linear (ii) MOLECULE TYPE: protein (xi) SEQUENCE DESCRIPTION: SEQ ID NO:67:

```
Phe Gly Phe Lys Leu Ser His Leu Val Ser Lys Tyr Cys Ala Cys Ala
  1               5                  10                  15

Leu Ala Ser Ala Leu Lys Tyr Ser Ile Asp His Gly Pro Arg Ile Ile
                 20                  25                  30

Gly Gly Glu Val Ala Gly Glu Gly Ser Ala Pro Tyr Gln Val Ser Leu
            35                  40                  45

Arg Thr Lys Glu Gly Asn His Phe Cys Gly Gly Ser Ile Leu Asn Lys
        50                  55                  60

Arg Trp Val Val Thr Ala Ala His Cys Leu Glu Pro Glu Ile Leu Asp
 65              70                  75                  80

Ser Val Tyr Val Gly Ser Asn His Leu Asp Arg Lys Gly Arg Tyr Tyr
                 85                  90                  95

Asp Val Glu Arg Tyr Ile Ile His Glu Lys Tyr Ile Gly Glu Leu Asn
                100                 105                 110

Asn Phe Tyr Ala Asp Ile Gly Leu Ile Lys Leu Asp Gly Arg Leu Arg
            115                 120                 125

Ile Gln
    130
```

(2) INFORMATION FOR SEQ ID NO:68:

(i) SEQUENCE CHARACTERISTICS:
        (A) LENGTH: 240 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..240

(ix) FEATURE:
        (A) NAME/KEY: Xaa = any amino acid
        (B) LOCATION: 73

(xi) SEQUENCE DESCRIPTION: SEQ ID NO:68:

```
CGG GCT GCA GGA ATT CGG CAC GAG AAG AAA CTG CCA ATA TTA ATC GCC      48
Arg Ala Ala Gly Ile Arg His Glu Lys Lys Leu Pro Ile Leu Ile Ala
 1               5                  10                  15

TTG ATC GGA TGC GTT CTT TCT GAA GAA ATA GAG GAT CGC ATT GTC GGC      96
Leu Ile Gly Cys Val Leu Ser Glu Glu Ile Glu Asp Arg Ile Val Gly
                20                  25                  30

GGA ACG GCA GTT GAT ATA AGA GGT TTT CCC TGG CAG GTA TCA ATT CAA     144
Gly Thr Ala Val Asp Ile Arg Gly Phe Pro Trp Gln Val Ser Ile Gln
            35                  40                  45

ACC GAA AAC CGT CAT TTT TGT GGT GGT TCT ATT ATC GAT AAA AGC TGG     192
Thr Glu Asn Arg His Phe Cys Gly Gly Ser Ile Ile Asp Lys Ser Trp
        50                  55                  60

ATA TTA ACT GCC GCA CAT TGT GTA CMC GAT ATG AAG ATG TCG AAC TGG     240
Ile Leu Thr Ala Ala His Cys Val Xaa Asp Met Lys Met Ser Asn Trp
65                  70                  75                  80
```

(2) INFORMATION FOR SEQ ID NO:69:

(i) SEQUENCE CHARACTERISTICS:
        (A) LENGTH: 80 amino acids
        (B) TYPE: amino acid
        (D) TOPOLOGY: linear (ii) MOLECULE TYPE: protein (ix) FEATURE:
        (A) NAME/KEY: Xaa = any amino acid
        (B) LOCATION: 73

(xi) SEQUENCE DESCRIPTION: SEQ ID NO:69:

```
Arg Ala Ala Gly Ile Arg His Glu Lys Lys Leu Pro Ile Leu Ile Ala
 1               5                  10                  15

Leu Ile Gly Cys Val Leu Ser Glu Glu Ile Glu Asp Arg Ile Val Gly
                20                  25                  30

Gly Thr Ala Val Asp Ile Arg Gly Phe Pro Trp Gln Val Ser Ile Gln
            35                  40                  45

Thr Glu Asn Arg His Phe Cys Gly Gly Ser Ile Ile Asp Lys Ser Trp
        50                  55                  60

Ile Leu Thr Ala Ala His Cys Val Xaa Asp Met Lys Met Ser Asn Trp
65                  70                  75                  80
```

(2) INFORMATION FOR SEQ ID NO:70:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..177

(xi) SEQUENCE DESCRIPTION: SEQ ID NO:70:

```
CAC GAG ATT TTA TTA AGC GCA TTA TTT GCA AGT GTA ATT TGC TCC TTT      48
His Glu Ile Leu Leu Ser Ala Leu Phe Ala Ser Val Ile Cys Ser Phe
 1               5                  10                  15

AAC GCG GAA GTA CAA AAT CGA ATC GTT GGT GGC AAT GAT GTA AGT ATT      96
Asn Ala Glu Val Gln Asn Arg Ile Val Gly Gly Asn Asp Val Ser Ile
                20                  25                  30

TCA AAA ATT GGG TGG CAA GTA TCT ATT CAA AGT AAT AAA CAA CAT TTC     144
Ser Lys Ile Gly Trp Gln Val Ser Ile Gln Ser Asn Lys Gln His Phe
```

```
            35                  40                  45
TGT GGT GGT TCA ATC ATT GCT AAA GAT GGG TCC                             177
Cys Gly Gly Ser Ile Ile Ala Lys Asp Gly Ser
     50                  55
```

(2) INFORMATION FOR SEQ ID NO:71:

(i) SEQUENCE CHARACTERISTICS:
        (A) LENGTH: 59 amino acids
        (B) TYPE: amino acid
        (D) TOPOLOGY: linear (ii) MOLECULE TYPE: protein (xi) SEQUENCE DESCRIPTION: SEQ ID NO:71:

```
His Glu Ile Leu Leu Ser Ala Leu Phe Ala Ser Val Ile Cys Ser Phe
 1               5                  10                  15

Asn Ala Glu Val Gln Asn Arg Ile Val Gly Gly Asn Asp Val Ser Ile
             20                  25                  30

Ser Lys Ile Gly Trp Gln Val Ser Ile Gln Ser Asn Lys Gln His Phe
         35                  40                  45

Cys Gly Gly Ser Ile Ile Ala Lys Asp Gly Ser
     50                  55
```

(2) INFORMATION FOR SEQ ID NO:72:

(i) SEQUENCE CHARACTERISTICS:
        (A) LENGTH: 168 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..168

(xi) SEQUENCE DESCRIPTION: SEQ ID NO:72:

```
ATC ATG GCA AAT TTT AGG CTA TTC ACC TTA CTA GCC TTG GTT TCA GTA          48
Ile Met Ala Asn Phe Arg Leu Phe Thr Leu Leu Ala Leu Val Ser Val
 1               5                  10                  15

GCA ACT TCC AAA TAT ATT GAT CCA AGA ATA ATT GGA GGC GAA GAT GCT          96
Ala Thr Ser Lys Tyr Ile Asp Pro Arg Ile Ile Gly Gly Glu Asp Ala
             20                  25                  30

CCT GAA GGC TCG GCT CCG TAC CAA GTT TCA TTG AGA AAT CAG AAT CTG         144
Pro Glu Gly Ser Ala Pro Tyr Gln Val Ser Leu Arg Asn Gln Asn Leu
         35                  40                  45

GAG CAT TTC TGT GGT GGT TCC ATT                                         168
Glu His Phe Cys Gly Gly Ser Ile
     50                  55
```

(2) INFORMATION FOR SEQ ID NO:73:

(i) SEQUENCE CHARACTERISTICS:
        (A) LENGTH: 56 amino acids
        (B) TYPE: amino acid
        (D) TOPOLOGY: linear (ii) MOLECULE TYPE: protein (xi) SEQUENCE DESCRIPTION: SEQ ID NO:73:

```
Ile Met Ala Asn Phe Arg Leu Phe Thr Leu Leu Ala Leu Val Ser Val
 1               5                  10                  15

Ala Thr Ser Lys Tyr Ile Asp Pro Arg Ile Ile Gly Gly Glu Asp Ala
```

```
                    20                  25                  30
Pro Glu Gly Ser Ala Pro Tyr Gln Val Ser Leu Arg Asn Gln Asn Leu
            35                  40                  45
Glu His Phe Cys Gly Gly Ser Ile
        50                  55
```

(2) INFORMATION FOR SEQ ID NO:74:

(i) SEQUENCE CHARACTERISTICS:
    (A) LENGTH: 192 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 1..192

(xi) SEQUENCE DESCRIPTION: SEQ ID NO:74:

```
GCA CGA GAT CGC ATT GTT GGA GGA TTG GAG GCG AAA AAT GGA TCA GCC      48
Ala Arg Asp Arg Ile Val Gly Gly Leu Glu Ala Lys Asn Gly Ser Ala
 1               5                  10                  15

CCA TTC ATG GTT TCT TTG CAA GCG GAA GAC TAT TTT CAT TTT TGT GGA      96
Pro Phe Met Val Ser Leu Gln Ala Glu Asp Tyr Phe His Phe Cys Gly
                20                  25                  30

TCC TCT ATT CTG AAT GAG AGA TGG GTT CTT ACT GCT GCT CAC TGT ATC     144
Ser Ser Ile Leu Asn Glu Arg Trp Val Leu Thr Ala Ala His Cys Ile
            35                  40                  45

CAA CCA AAT GTA CAC AAG TAC GTT TAC GTC GGT TCG AAC AAC GTA GAA     192
Gln Pro Asn Val His Lys Tyr Val Tyr Val Gly Ser Asn Asn Val Glu
        50                  55                  60
```

(2) INFORMATION FOR SEQ ID NO:75:

(i) SEQUENCE CHARACTERISTICS:
    (A) LENGTH: 64 amino acids
    (B) TYPE: amino acid
    (D) TOPOLOGY: linear (ii) MOLECULE TYPE: protein (xi) SEQUENCE DESCRIPTION: SEQ ID NO:75:

```
Ala Arg Asp Arg Ile Val Gly Gly Leu Glu Ala Lys Asn Gly Ser Ala
 1               5                  10                  15

Pro Phe Met Val Ser Leu Gln Ala Glu Asp Tyr Phe His Phe Cys Gly
                20                  25                  30

Ser Ser Ile Leu Asn Glu Arg Trp Val Leu Thr Ala Ala His Cys Ile
            35                  40                  45

Gln Pro Asn Val His Lys Tyr Val Tyr Val Gly Ser Asn Asn Val Glu
        50                  55                  60
```

(2) INFORMATION FOR SEQ ID NO:76:

(i) SEQUENCE CHARACTERISTICS:
    (A) LENGTH: 207 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 1..204

(xi) SEQUENCE DESCRIPTION: SEQ ID NO:76:

| CCA | ATC | CAC | GAT | AGC | CAA | TAT | GCA | CTT | TTG | CAG | ATA | TGG | GTC | AAG | GGT | 48 |
| Pro | Ile | His | Asp | Ser | Gln | Tyr | Ala | Leu | Leu | Gln | Ile | Trp | Val | Lys | Gly | |
| 1 | | | | 5 | | | | | 10 | | | | | 15 | | |

| GCA | TGT | AAG | GGT | GAT | TCC | GGT | GGC | CCC | TTA | GTC | ATC | AAT | GGA | CAA | CTT | 96 |
| Ala | Cys | Lys | Gly | Asp | Ser | Gly | Gly | Pro | Leu | Val | Ile | Asn | Gly | Gln | Leu | |
| | | | 20 | | | | | 25 | | | | | 30 | | | |

| CAT | GGA | ATT | GTT | TCC | TGG | GGC | ATT | CCT | TGC | GCT | GTC | GCA | AGC | CTG | ATG | 144 |
| His | Gly | Ile | Val | Ser | Trp | Gly | Ile | Pro | Cys | Ala | Val | Ala | Ser | Leu | Met | |
| | | | 35 | | | | | 40 | | | | | 45 | | | |

| TAT | TCA | CAA | GAG | TTT | CTC | ATT | ATG | TCG | ATT | GGA | TTA | AAT | CCA | AAA | TTG | 192 |
| Tyr | Ser | Gln | Glu | Phe | Leu | Ile | Met | Ser | Ile | Gly | Leu | Asn | Pro | Lys | Leu | |
| | 50 | | | | | 55 | | | | | 60 | | | | | |

| AAT | AAA | ATT | GTT | TAG | | | | | | | | | | | | 207 |
| Asn | Lys | Ile | Val | | | | | | | | | | | | | |
| 65 | | | | | | | | | | | | | | | | |

(2) INFORMATION FOR SEQ ID NO:77:

(i) SEQUENCE CHARACTERISTICS:
        (A) LENGTH: 68 amino acids
        (B) TYPE: amino acid
        (D) TOPOLOGY: linear (ii) MOLECULE TYPE: protein (xi) SEQUENCE DESCRIPTION: SEQ ID NO:77:

| Pro | Ile | His | Asp | Ser | Gln | Tyr | Ala | Leu | Leu | Gln | Ile | Trp | Val | Lys | Gly |
| 1 | | | | 5 | | | | | 10 | | | | | 15 | |

| Ala | Cys | Lys | Gly | Asp | Ser | Gly | Gly | Pro | Leu | Val | Ile | Asn | Gly | Gln | Leu |
| | | | 20 | | | | | 25 | | | | | 30 | | |

| His | Gly | Ile | Val | Ser | Trp | Gly | Ile | Pro | Cys | Ala | Val | Ala | Ser | Leu | Met |
| | | | 35 | | | | | 40 | | | | | 45 | | |

| Tyr | Ser | Gln | Glu | Phe | Leu | Ile | Met | Ser | Ile | Gly | Leu | Asn | Pro | Lys | Leu |
| | 50 | | | | | 55 | | | | | 60 | | | | |

Asn Lys Ile Val
65

(2) INFORMATION FOR SEQ ID NO:78:

(i) SEQUENCE CHARACTERISTICS:
        (A) LENGTH: 159 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..156

(xi) SEQUENCE DESCRIPTION: SEQ ID NO:78:

| GGA | GGT | CCT | TTG | GCA | ATC | AAT | GGT | GAA | CTT | GTT | GGT | GTT | ACT | TCA | TTC | 48 |
| Gly | Gly | Pro | Leu | Ala | Ile | Asn | Gly | Glu | Leu | Val | Gly | Val | Thr | Ser | Phe | |
| 1 | | | | 5 | | | | | 10 | | | | | 15 | | |

| ATT | ATG | GGG | ACA | TGT | GGA | GGA | GGA | CAT | CCT | GAT | GTC | TTC | GGT | CGA | GTC | 96 |
| Ile | Met | Gly | Thr | Cys | Gly | Gly | Gly | His | Pro | Asp | Val | Phe | Gly | Arg | Val | |
| | | | 20 | | | | | 25 | | | | | 30 | | | |

| CTT | GAC | TTC | AAA | CCA | TGG | ATT | GAT | TCT | CAT | ATG | GCA | AAT | GAC | GGC | GCT | 144 |
| Leu | Asp | Phe | Lys | Pro | Trp | Ile | Asp | Ser | His | Met | Ala | Asn | Asp | Gly | Ala | |
| | | | 35 | | | | | 40 | | | | | 45 | | | |

```
AAT TCT TTT ATT TAA                                                   159
Asn Ser Phe Ile
    50
```

(2) INFORMATION FOR SEQ ID NO:79:

(i) SEQUENCE CHARACTERISTICS:
        (A) LENGTH: 52 amino acids
        (B) TYPE: amino acid
        (D) TOPOLOGY: linear (ii) MOLECULE TYPE: protein (xi) SEQUENCE DESCRIPTION: SEQ ID NO:79:

```
Gly Gly Pro Leu Ala Ile Asn Gly Glu Leu Val Gly Val Thr Ser Phe
 1           5                  10                  15

Ile Met Gly Thr Cys Gly Gly Gly His Pro Asp Val Phe Gly Arg Val
            20                  25                  30

Leu Asp Phe Lys Pro Trp Ile Asp Ser His Met Ala Asn Asp Gly Ala
            35                  40                  45

Asn Ser Phe Ile
    50
```

FLEA PROTEASE PROTEINS

CROSS-REFERENCE TO RELATED APPLICATIONS

The present application is a continuation-in-part of U.S. patent application Ser. No. 08/326,773, entitled "USE OF PROTEASE INHIBITORS AND PROTEASE VACCINES TO PROTECT ANIMALS FROM FLEA INFESTATION", filed Oct. 18, 1994, which issued as U.S. Pat. No. 5,766,609 on Jun. 16, 1998, and which is a continuation-in-part of U.S. patent application Ser. No. 07/806,482, entitled "FLEA MIDGUT-GENERATED ANTIFLEA VACCINES", filed Dec. 13, 1991, which issued as U.S. Pat. No. 5,356,622 on Oct. 18, 1994. Both applications are each incorporated by reference herein in its entirety.

FIELD OF THE INVENTION

The present invention relates to novel flea protease proteins and their use to reduce flea infestation of animals. The present invention also relates to the use of anti-flea protease antibodies and other compounds that reduce flea protease activity to reduce flea infestation of animals.

BACKGROUND OF THE INVENTION

Fleas, which belong to the insect order Siphonaptera, are obligate ectoparasites for a wide variety of animals, including birds and mammals. Flea infestation of animals is of health and economic concern because fleas are known to cause and/or transmit a variety of diseases. Fleas cause and/or carry infectious agents that cause, for example, flea allergy dermatitis, anemia, murine typhus, plague and tapeworm. In addition, fleas are a problem for animals maintained as pets because the infestation becomes a source of annoyance for the pet owner who may find his or her home generally contaminated with fleas which feed on the pets. As such, fleas are a problem not only when they are on an animal but also when they are in the general environment of the animal.

The medical and veterinary importance of flea infestation has prompted the development of reagents capable of controlling flea infestation. Commonly encountered methods to control flea infestation are generally focussed on use of insecticides in formulations such as sprays, shampoos, dusts, dips, or foams, or in pet collars. While some of these products are efficacious, most, at best, offer protection of a very limited duration. Furthermore, many of the methods are often not successful in reducing flea populations on the pet for one or more of the following reasons: (1) failure of owner compliance (frequent administration is required); (2) behavioral or physiological intolerance of the pet to the pesticide product or means of administration; and (3) the emergence of flea populations resistant to the prescribed dose of pesticide. Additional anti-flea products include non-toxic reagents such as insect growth regulators (IGRs), including methoprene, which mimics flea hormones and affect flea larval development.

An alternative method for controlling flea infestation is the use of flea vaccines to be administered to animals prior to or during flea infestation. However, despite considerable interest in developing anti-flea reagents, no flea vaccine presently exists.

SUMMARY OF THE INVENTION

The present invention relates to flea serine protease and aminopeptidase proteins; to flea serine protease and aminopeptidase nucleic acid molecules, including those that encode such proteins; to antibodies raised against such proteins; and to compounds that inhibit flea serine protease and/or aminopeptidase activities. The present invention also includes methods to obtain such proteins, nucleic acid molecules, antibodies, and inhibitors. Also included in the present invention are therapeutic compositions comprising such proteins, nucleic acid molecules, antibodies, and/or inhibitors as well as the use of such therapeutic compositions to protect a host animal from flea infestation.

One embodiment of the present invention is an isolated flea serine protease nucleic acid molecule that hybridizes under stringent hybridization conditions with a flea serine protease gene. Particularly preferred flea serine protease nucleic acid molecules include nucleic acid sequences SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, the nucleic acid sequences disclosed in Table 2 and/or nucleic acid sequences encoding proteins having amino acid sequences SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, and/or the amino acid sequences disclosed in Table 2, as well as allelic variants of any of those nucleic acid sequences.

Another embodiment of the present invention is an isolated flea aminopeptidase nucleic acid molecule that hybridizes under stringent hybridization conditions with a flea aminopeptidase gene. A particularly preferred flea aminopeptidase nucleic acid molecule includes nucleic acid sequence SEQ ID NO:50 or an allelic variant thereof.

The present invention also relates to recombinant molecules, recombinant viruses and recombinant cells that include flea serine protease and/or aminopeptidase nucleic acid molecules of the present invention. Also included are methods to produce such nucleic acid molecules, recombinant molecules, recombinant viruses and recombinant cells.

Another embodiment of the present invention includes an isolated flea serine protease protein, including a protein that includes a flea serine protease protein. A preferred flea serine protease protein is capable of eliciting an immune response against a natural flea protease when administered to an animal and/or of having serine protease activity. Particularly preferred flea serine protease proteins are those encoded by preferred flea serine protease nucleic acid molecules of the present invention.

Yet another embodiment of the present invention includes an isolated flea aminopeptidase protein, including a protein that includes a flea aminopeptidase protein. A preferred flea aminopeptidase protein is capable of eliciting an immune response against a natural flea protease when administered to an animal and/or of having aminopeptidase activity. A particularly preferred flea aminopeptidase protein is a protein that includes SEQ ID NO:51 or a protein that is encoded by a nucleic acid molecule that is an allelic variant of a nucleic acid molecule comprising SEQ ID NO:50.

The present invention also relates to mimetopes of flea serine protease and aminopeptidase proteins as well as to isolated antibodies that selectively bind to flea serine protease proteins or mimetopes thereof or to flea aminopeptidase proteins or mimetopes thereof. Also included are methods, including recombinant methods, to produce proteins, mimetopes and antibodies of the present invention.

Yet another embodiment of the present invention is a therapeutic composition that is capable of reducing flea infestation. Such a therapeutic composition includes one or more of the following protective compounds: an isolated flea serine protease protein or a mimetope thereof; an isolated flea serine protease nucleic acid molecule that hybridizes under stringent hybridization conditions with a flea serine protease gene; an isolated antibody that selectively binds to a flea serine protease protein; an inhibitor of flea serine protease activity identified by its ability to inhibit flea serine protease activity; an isolated flea aminopeptidase protein or a mimetope thereof; an isolated flea aminopeptidase nucleic acid molecule that hybridizes under stringent hybridization conditions with a flea aminopeptidase gene; an isolated antibody that selectively binds to a flea aminopeptidase protein; and an inhibitor of flea aminopeptidase activity identified by its ability to inhibit flea aminopeptidase activity. A preferred therapeutic composition of the present invention also includes an excipient, an adjuvant and/or a carrier. Also included in the present invention is a method to reduce flea infestation. The method includes the step of administering to the animal a therapeutic composition of the present invention.

Another embodiment of the present invention is a method to identify a compound capable of inhibiting flea serine protease or flea aminopeptidase activity. The method includes the steps of: (a) contacting an isolated flea serine protease protein or a flea aminopeptidase protein with a putative inhibitory compound under conditions in which, in the absence of the compound, the protein has, respectively, serine protease or aminopeptidase activity; and (b) determining if the putative inhibitory compound inhibits the respective activity. Also included in the present invention is a test kit to identify a compound capable of inhibiting flea serine protease or flea aminopeptidase activity. Such a kit includes an isolated flea serine protease protein having serine protease activity or an isolated flea aminopeptidase protein having aminopeptidase activity and a means for determining the extent of inhibition of the respective activity in the presence of a putative inhibitory compound.

BRIEF DESCRIPTION OF THE FIGURES

FIG. 5A depicts a Coomassie stained SDS-PAGE of partially purified (1,3-$^3$H) -diisopropylfluoro-phosphate-labeled fed flea midgut serine proteases.

FIG. 5B depicts an autoradiogram of the SDS-PAGE gel of FIG. 5A of partially purified (1,3-$^3$H)-diisopropylfluorophosphate-labeled fed flea midgut serine proteases.

DETAILED DESCRIPTION OF THE INVENTION

Figure 1:
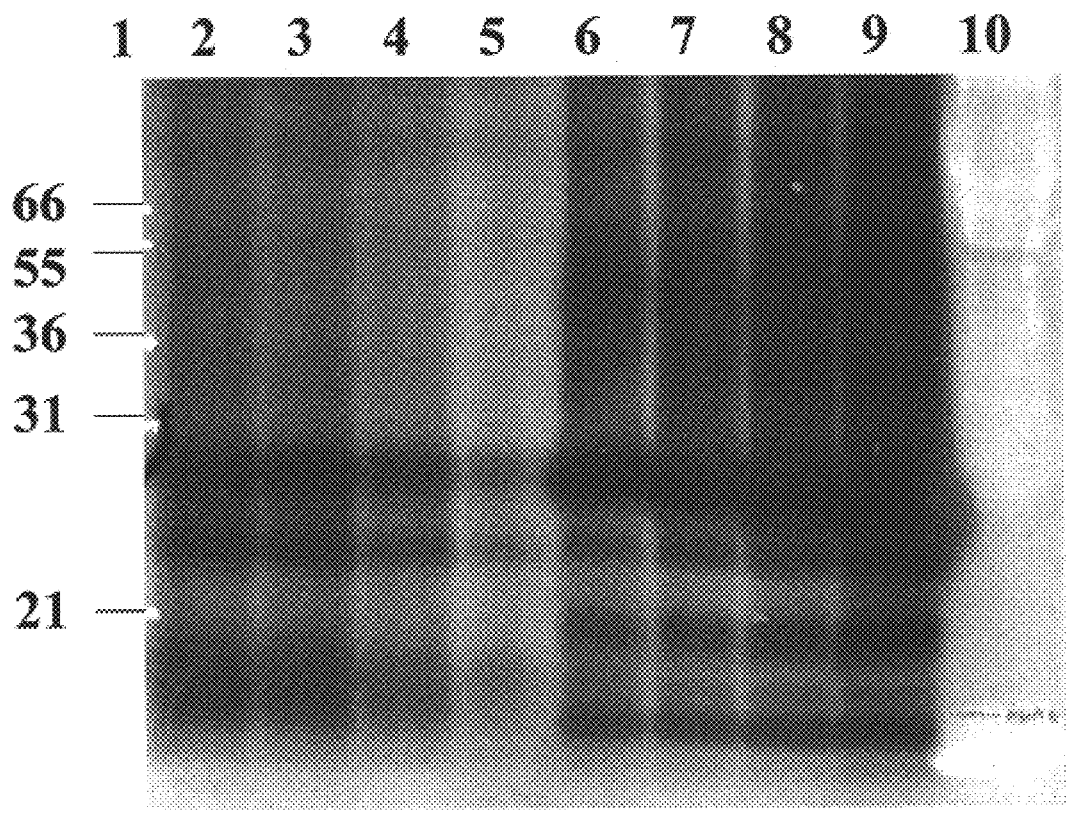
FIG. 1 depicts a protease substrate gel analysis of the relative proteolytic activity in 1, 2, 5 or 10 midguts from either fed or unfed female fleas.

The present invention includes the use of compounds that inhibit flea protease activity to protect a host animal from flea infestation. The inventors have discovered that proteases are significant components of the flea midgut and are good targets for immunotherapeutic and/or chemotherapeutic intervention to reduce flea burden both on the host animal and in the immediate (i.e., surrounding) environment of the animal. The inventors have shown, for example, that the viability and/or fecundity of fleas consuming a blood meal is reduced when the blood meal contains compounds that reduce flea protease activity, probably because the compounds interfere with flea digestion and other functions. Compounds that reduce the amount and/or activity of flea proteases without substantially harming the host animal are included in the present invention. Such compounds include flea protease vaccines, anti-flea protease antibodies, flea protease inhibitors, and/or compounds that suppress protease synthesis; such compounds are discussed in more detail below.

One embodiment of the present invention is a method to protect a host animal from flea infestation by treating the animal with a composition that includes a compound that reduces the protease activity of fleas feeding (includes fleas in the process of feeding as well as fleas having fed) from the treated animal thereby reducing the flea burden on the animal and in the environment of the animal. It is to be noted that the term "a" or "an" entity refers to one or more of that entity; for example, a compound refers to one or more compounds. As such, the terms "a" (or "an") , "one or more" and "at least one" can be used interchangeably herein. Thus, a composition of the present invention can include one or more compounds that target (reduced the activity of) one or more proteases in the flea.

As used herein, the phrase "to protect an animal from flea infestation" refers to reducing the potential for flea population expansion on and around the animal (i.e., reducing the flea burden). Preferably, the flea population size is decreased, optimally to an extent that the animal is no longer bothered by fleas. A host animal, as used herein, is an animal from which fleas can feed by attaching to and feeding through the skin of the animal. Fleas, and other ectoparasites, can live on a host animal for an extended period of time or can attach temporarily to an animal in order to feed. At any given time, a certain percentage of a flea population can be on a host animal whereas the remainder can be in the environment surrounding the animal (i.e., in the environment of the animal). Such an environment can include not only adult fleas, but also flea eggs and/or flea larvae. The environment can be of any size such that fleas in the environment are able to jump onto and off of a host animal. As such, it is desirable not only to reduce the flea burden on an animal per se, but also to reduce the flea burden in the environment surrounding the animal.

In accordance with the present invention, a host animal is treated by administering to the animal a compound of the present invention in such a manner that the compound itself (e.g., a protease inhibitor, protease synthesis suppressor or anti-flea protease antibody) or a product generated by the animal in response to administration of the compound (e.g., antibodies produced in response to a flea protease vaccine, or conversion of an inactive inhibitor "prodrug" to an active protease inhibitor) ultimately enters the flea midgut. An animal is preferably treated in such a way that the compound or product thereof enters the blood stream of the animal. Fleas are then exposed to the compound when they feed from the animal. For example, flea protease inhibitors administered to an animal are administered in such a way that the inhibitors enter the blood stream of the animal, where they can be taken up by feeding fleas. In another embodiment, when a host animal is administered a flea protease vaccine, the treated animal mounts an immune response resulting in the production of antibodies against the protease (anti-flea protease antibodies) which circulate in the animal's blood stream and are taken up by fleas upon feeding. Blood taken up by fleas enters the flea midgut where compounds of the present invention, or products thereof, such as anti-flea protease antibodies, flea protease inhibitors, and/or protease synthesis suppressors, interact with, and reduce proteolytic activity in the flea midgut. The present invention also includes the ability to reduce larval flea infestation in that when fleas feed from a host animal that has been administered a therapeutic composition of the present invention, at least a portion of compounds of the present invention, or products thereof, in the blood taken up by the flea are excreted by the flea in feces, which is subsequently ingested by flea larvae. It is of note that flea larvae obtain most, if not all, of their nutrition from flea feces.

In accordance with the present invention, reducing proteolytic activity in flea midguts can lead to a number of outcomes that reduce flea burden on treated animals and their surrounding environments. Such outcomes include, but are not limited to, (a) reducing the viability of fleas that feed from the treated animal, (b) reducing the fecundity of female fleas that feed from the treated animal, (c) reducing the reproductive capacity of male fleas that feed from the treated animal, (d) reducing the viability of eggs laid by female fleas that feed from the treated animal, (e) altering the blood feeding behavior of fleas that feed from the treated animal (e.g., fleas take up less volume per feeding or feed less frequently), (f) reducing the viability of flea larvae, for example due to the feeding of larvae from feces of fleas that feed from the treated animal and/or (g) altering the development of flea larvae (e.g., by decreasing feeding behavior, inhibiting growth, inhibiting (e.g., slowing or blocking) molting, and/or otherwise inhibiting maturation to adults).

One embodiment of the present invention is a composition that includes one or more compounds that reduce the activity of one or more flea proteases directly (e.g., an anti-flea protease antibody or a flea protease inhibitor) and/or indirectly (e.g., a flea protease vaccine). Suitable flea proteases to target include flea aminopeptidases, flea carboxypeptidases and/or flea endopeptidases. Preferred flea proteases to target include, but are not limited to, serine proteases, metalloproteases, aspartic acid proteases and/or cysteine proteases. It is to be noted that these preferred groups of proteases include aminopeptidases, carboxypeptidases and/or endopeptidases. Preferred flea proteases to target include, but are not limited to, proteases that degrade hemoglobin, proteases involved in blood coagulation and/or lytic (anti-coagulation) pathways, proteases involved in the maturation of peptide hormones, proteases that inhibit complement or other host immune response elements (e.g., antibodies) and/or proteases involved in vitellogenesis. A number of proteases are known to those skilled in the art, including, but not limited to, aminopeptidases, such as leucine aminopeptidase and aminopeptidases B and M; astacin-like metalloproteases; calpains; carboxypeptidases, such as carboxypeptidases A, P and Y; cathepsins, such as cathepsins B, D, E, G, H, and L, chymotrypsins; cruzipains; meprins; papains; pepsins; renins; thermolysins and trypsins. A particularly preferred protease to target is a protease having a proteolytic activity that, when targeted with a composition of the present invention, reduces flea burden without substantially harming the host animal. Such a protease can be identified using, for example, methods as disclosed herein.

One aspect of the present invention is the discovery that a substantial amount of the proteolytic activity found in flea midguts is serine protease activity. Both in vitro and in vivo studies using a number of protease inhibitors substantiate this discovery, details of which are disclosed in the Examples. As such a particularly preferred protease to target is a serine protease. Examples of serine proteases, include, but are not limited to, acrosins, bromelains, cathepsin G, chymotrypsins, collagenases, elastases, factor Xa, ficins, kallikreins, papains, plasmins, Staphylococcal V8 proteases, thrombins and trypsins. In one embodiment, a preferred flea serine protease to target includes a protease having trypsin-like or chymotrypsin-like activity. It is appreciated by those skilled in the art that an enzyme having "like" proteolytic activity has similar activity to the referenced protease, although the exact structure of the preferred substrate cleaved may differ. "Like" proteases usually have similar tertiary structures as their referenced counterparts.

Protease inhibitor studies disclosed in the Examples section also indicate that additional preferred proteases to target include aminopeptidases and/or metalloproteases. Examples of such proteases include exo- and endo-metalloproteases, digestive enzymes, and enzymes involved in peptide hormone maturation. One example of an aminopeptidase that is also a metalloprotease is leucine aminopeptidase.

Suitable compounds to include in compositions of the present invention include, but are not limited to, a vaccine comprising a flea protease (a flea protease vaccine), an antibody that selectively binds to a flea protease (an anti-flea protease antibody), a flea protease inhibitor (a compound other than a vaccine or an antibody that inhibits a flea protease), and a mixture of such compounds. As used herein, a mixture thereof refers to a combination of one or more of the cited entities. Compositions of the present invention can also include compounds to suppress protease synthesis or maturation, such as, but not limited to, protease modulating peptides.

A preferred embodiment of the present invention is a flea protease vaccine and its use to reduce the flea population on and around an animal. A flea protease vaccine can include one or more proteins capable of eliciting an immune response against a flea protease and can also include other components. Preferred flea protease vaccines include a flea serine protease, a flea metalloprotease, a flea aspartic acid protease and/or a flea cysteine protease, with flea serine protease, flea metalloprotease and/or flea aminopeptidase vaccines being more preferred. Examples of flea protease vaccines include soluble flea midgut preparations of the present invention as well as one or more isolated proteins of the present invention.

One embodiment of the present invention is a soluble flea midgut preparation. Such a preparation includes primarily components naturally present in the lumen of a flea midgut and, depending on the method of preparation, can also include one or more peripheral midgut membrane proteins. Methods to preferentially include, or exclude, membrane proteins from such a preparation are known to those skilled in the art. The present invention includes the discovery that such a preparation has proteolytic activity, of which a substantial portion is serine protease activity. Preferably at least about 70 percent of the proteolytic activity in a soluble flea midgut soluble preparation is serine protease activity, as can be indicated by the ability to inhibit at least about 70 percent of the proteolytic activity with 4-2-aminoethylbenzenesulfonylfluoride-hydrochloride (AEBSF). Serine protease activity can also be identified using other known inhibitors or substrates. Other preferred inhibitors that can inhibit at least about 70 percent of the proteolytic activity of a soluble flea midgut preparation of the present invention include soybean trypsin inhibitor, 1,3-diisopropylfluorophosphate or leupeptin.

A soluble flea midgut preparation of the present invention includes proteases that range in molecular weight from about 5 kilodaltons (kD) to about 200 kD, as determined by SDS-PAGE (sodium dodecyl sulfate polyacrylamide gel electrophoresis), with at least a substantial portion of the serine proteases ranging in molecular weight from about 5 kD to about 60 kD, as determined by SDS-PAGE. A substantial portion of protease activity in a soluble flea midgut preparation of the present invention has a pH activity optimum ranging from about pH 5 to about pH 10, preferably an activity optimum ranging from about pH 7 to about pH 9, and even more preferably an activity optimum of about pH 8. While not being bound by theory, such a pH optimum suggests that a large proportion of proteases in soluble flea midgut preparations of the present invention are serine proteases. It is also interesting to note that the pH of the flea midgut is also about pH 8. The findings that proteases in soluble flea midgut preparations of the present invention exhibit a varied pattern of inhibition by protease inhibitors of a given type (e.g., serine protease inhibitors), as well as variances seen in molecular weights and pH optima of the proteases, suggest that there are a number of protease isoforms in such preparations.

A soluble flea midgut preparation of the present invention is preferably prepared by a method that includes the steps of (a) disrupting a flea midgut to produce a mixture including a liquid portion and a solid portion and (b) recovering the liquid portion to obtain a soluble flea midgut preparation. Such a method is a simplified version of methods disclosed in Ser. No. 07/806,482, ibid. It is to be noted that in accordance with the present invention, methods disclosed in Ser. No. 07/806,482 ibid. can also be used to prepare soluble flea midgut preparations having similar proteolytic activities.

Flea midguts can be obtained (e.g., dissected from) from unfed fleas or from fleas that recently consumed a blood meal (i.e., blood-fed fleas). Such midguts are referred to herein as, respectively, unfed flea midguts and fed flea midguts. Flea midguts can be obtained from either male or female fleas. As demonstrated in the Examples section, female flea midguts exhibit somewhat more proteolytic activity than do male flea midguts. Furthermore, fed flea midguts have significantly more proteolytic activity than do unfed flea midguts. While not being bound by theory, it is believed that blood feeding induces in flea midguts the synthesis and/or activation of proteases as well as other factors (e.g., enzymes, other proteins, co-factors, etc.) important in digesting the blood meal, as well as in neutralizing host molecules potentially damaging to the flea (e.g., complement, immunoglobulins, blood coagulation factors). It is also to be appreciated that unfed flea midguts may contain significant targets not found in fed flea midguts and vice versa. Furthermore, although the present application focusses primarily on flea midgut proteases, it is to be noted that the present invention also includes other components of soluble flea midgut preparations of the present invention that provide suitable targets to reduce flea burden on an animal and in the environment of that animal; see also Ser. No. 07/806,482 now U.S. Pat. No. 5,356,622, ibid.

Methods to disrupt flea midguts in order to obtain a soluble flea midgut preparation are known to those skilled in the art and can be selected according to, for example, the volume being processed and the buffers being used. Such methods include any technique that promotes cell lysis, such as, but are not limited to, chemical disruption techniques (e.g., exposure of midguts to a detergent) as well as mechanical disruption techniques (e.g., homogenization, sonication, use of a tissue blender or glass beads, and freeze/thaw techniques).

Methods to recover a soluble flea midgut preparation are also known to those skilled in the art and can include any method by which the liquid portion of disrupted flea midguts is separated from the solid portion (e.g., filtration or centrifugation). In a preferred embodiment, disrupted flea midguts are subjected to centrifugation, preferably at an acceleration ranging from about 10,000×g to about 15,000×g for several minutes (e.g., from about 1 minute to about 15 minutes). The supernatant from such a centrifugation comprises a soluble flea midgut preparation of the present invention.

The present invention also includes an isolated protein that includes an amino acid sequence encoded by a nucleic acid molecule capable of hybridizing under stringent conditions (i.e., that hybridize under stringent hybridization conditions) with a nucleic acid molecule that encodes a protease present in (i.e., can be found in) a flea midgut, such as a midgut from a blood-fed female flea, a midgut from a blood-fed male flea, a midgut from an unfed female flea or a midgut from an unfed male flea. A preferred midgut protease is present in the lumen of the midgut.

An isolated protein of the present invention, also referred to herein as an isolated protease protein, preferably is capable of eliciting an immune response against a flea midgut protease and/or has proteolytic activity. According to the present invention, an isolated, or biologically pure, protein, is a protein that has been removed from its natural milieu. As such, "isolated" and "biologically pure" do not necessarily reflect the extent to which the protein has been purified. An isolated protease protein can be obtained from its natural source. Such an isolated protein can also be produced using recombinant DNA technology or chemical synthesis.

As used herein, an isolated protein of the present invention can be a full-length protein or any homologue of such a protein, such as a protein in which amino acids have been deleted (e.g., a truncated version of the protein, such as a peptide), inserted, inverted, substituted and/or derivatized (e.g., by glycosylation, phosphorylation, acetylation, myristylation, prenylation, palmitoylation, amidation and/or addition of glycerophosphatidyl inositol) such that the homologue comprises a protein having an amino acid sequence that is sufficiently similar to a natural flea midgut protease that a nucleic acid sequence encoding the homologue is capable of hybridizing under stringent conditions to (i.e., with) a nucleic acid sequence encoding the corresponding natural flea midgut protease amino acid sequence. As used herein, stringent hybridization conditions refer to standard hybridization conditions under which nucleic acid molecules, including oligonucleotides, are used to identify similar nucleic acid molecules. Such standard conditions are disclosed, for example, in Sambrook et al., *Molecular Cloning: A Laboratory Manual*, Cold Spring Harbor Labs Press, 1989.

The minimal size of a protein homologue of the present invention is a size sufficient to be encoded by a nucleic acid molecule capable of forming a stable hybrid with the complementary sequence of a nucleic acid molecule encoding the corresponding natural protein. As such, the size of the nucleic acid molecule encoding such a protein homologue is dependent on nucleic acid composition and percent homology between the nucleic acid molecule and complementary sequence as well as upon hybridization conditions per se (e.g., temperature, salt concentration, and formamide concentration). The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode a protease protein homologue of the present invention is from about 12 to about 18 nucleotides in length. There is no limit, other than a practical limit, on the maximal size of such a nucleic acid molecule in that the nucleic acid molecule can include a portion of a gene, an entire gene, or multiple genes, or portions thereof. Similarly, the minimal size of a protease protein homologue of the present invention is from about 4 to about 6 amino acids in length, with preferred sizes depending on whether a full-length, multivalent (i.e., fusion protein having more than one domain each of which has a function), or functional portions of such proteins are desired. Protease protein homologues of the present invention preferably have protease activity and/or are capable of eliciting an immune response against a flea midgut protease.

A protease protein homologue of the present invention can be the result of allelic variation of a natural gene encoding a flea protease. A natural gene refers to the form of the gene found most often in nature. Protease protein homologues can be produced using techniques known in the art including, but not limited to, direct modifications to a gene encoding a protein using, for example, classic or recombinant DNA techniques to effect random or targeted mutagenesis. Isolated protease proteins of the present invention, including homologues, can be identified in a straightforward manner by the proteins' ability to effect proteolytic activity and/or to elicit an immune response against a flea midgut protease. Such techniques are known to those skilled in the art.

A preferred protease protein of the present invention is a flea serine protease, a flea metalloprotease, a flea aspartic acid protease, a flea cysteine protease, or a homologue of any of these proteases. A more preferred protease protein is a flea serine protease, a flea metalloprotease or a homologue of either. Also preferred is a flea aminopeptidase or a homologue thereof. Particularly preferred is a flea serine protease or a homologue thereof.

Preferred protease proteins of the present invention are flea protease proteins having molecular weights ranging from about 5 kD to about 200 kD, as determined by SDS-PAGE, and homologues of such proteins. More preferred are flea protease proteins having molecular weights ranging from about 5 kD to about 60 kD, as determined by SDS-PAGE, and homologues of such proteins. Even more preferred are flea serine protease proteins and particularly those having molecular weights of about 26 kD (denoted PfSP26), about 24 kD (denoted PfSP24), about 19 kD (denoted PfSP19) and about 6 kD (denoted PfSP6), as determined by SDS-PAGE, and homologues of such proteins.

One preferred embodiment of the present invention is an isolated flea protease protein that includes an amino acid sequence encoded by a nucleic acid molecule that hybridizes under stringent hybridization conditions with a flea serine protease gene or with a flea aminopeptidase gene. As used herein, a flea protease gene includes all nucleic acid sequences related to a natural flea protease gene such as regulatory regions that control production of a flea protease protein encoded by that gene (such as, but not limited to, transcription, translation or post-translation control regions) as well as the coding region itself.

The inventors have discovered an extensive family of serine proteases, encoded by a family of serine protease genes. Such a gene family may be due to allelic variants (i.e., genes having similar, but different, sequences at a given locus in a population of fleas) and/or to, the existence of serine protease genes at more than one locus in the flea genome. As such, the present invention includes flea serine protease genes comprising not only the nucleic acid sequences disclosed herein (e.g., genes including nucleic acid sequences SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38 and/or the nucleic acid sequences disclosed in Table 2) and/or nucleic acid sequences encoding proteins having amino acid sequences as disclosed herein (e.g., SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, and/or the amino acid sequences disclosed in Table 2), but also allelic variants of any of those nucleic acid sequences. (It should be noted that since nucleic acid sequencing technology is not entirely error-free, all sequences represented herein are at best apparent (i.e., deduced) nucleic acid or amino acid sequences.)

A preferred flea aminopeptidase gene includes nucleic acid sequence SEQ ID NO:50, which encodes an aminopeptidase protein including SEQ ID NO:51. Additional preferred aminopeptidase genes include allelic variants of SEQ ID NO:50.

A preferred flea serine protease protein of the present invention is encoded by a nucleic acid molecule that hybridizes under stringent hybridization conditions with at least one of the following nucleic acid molecules: nfSP1, nfSP2, nfSP3, nfSP4, nfSP5, nfSP6, nfSP7, nfSP8, nfSP9, nfSP10, nfSP11, nfSP12, nfSP13, nfSP14, nfSP15, nfSP16 and nfSP17. As used herein, each of these nucleic acid molecules represent the entire coding region of a flea serine protease gene of the present invention. Nucleic acid molecules that contain partial coding regions or other parts of the corresponding gene are denoted by names that include the size of those nucleic acid molecules (e.g., nfSP4$_{156}$). Nucleic acid molecules containing apparent full length coding regions for which the size is known also are denoted by names that include the size of those nucleic acid molecules (e.g., nfSP4$_{672}$). The production, and at least partial nucleic acid sequence, of such nucleic acid molecules is disclosed in the Examples.

Particularly preferred serine protease proteins are encoded by a nucleic acid molecule that hybridizes under stringent hybridization conditions with at least one of the following nucleic acid molecules: nfSP4$_{672}$, nfSP1$_{156}$, nfSP2$_{168}$, nfSP3$_{177}$, nfSP4$_{156}$, nfSP5$_{159}$, nfSP6$_{168}$, nfSP7$_{159}$, nfSP8$_{186}$, nfSP9$_{168}$, nfSP10$_{120}$, and nfSP11$_{162}$. Even more preferred serine protease proteins include the following amino acid sequences: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, and/or the amino acid sequences presented in Table 2. Additional particularly preferred serine protease proteins are encoded by allelic variants of nucleic acid molecules encoding proteins that include the cited amino acid sequences. Also preferred are flea serine protease proteins including regions that have at least about 50%, preferably at least about 75%, and more preferably at least about 90% identity with flea serine protease proteins having amino acid sequences as cited herein.

A preferred flea aminopeptidase protein of the present invention is encoded by a nucleic acid molecule that hybridizes under stringent hybridization conditions with nucleic acid molecule nfAP$_{453}$, the production of which is described in the Examples. Even more preferred is an aminopeptidase that includes amino acid sequence SEQ ID NO:51 or an aminopeptidase encoded by an allelic variant of a nucleic acid molecule that includes SEQ ID NO:50. Also preferred are flea aminopeptidase proteins including regions that have at least about 50%, preferably at least about 75%, and more preferably at least about 90% identity with SEQ ID NO:51.

One embodiment of the present invention is an isolated protein having proteolytic activity that is substantially inhibited by a serine protease inhibitor. Such inhibition can be measured by techniques known to those skilled in the art. To be substantially inhibited means that at least half of the proteolytic activity of the protease protein is inhibited by a serine protease inhibitor. Preferably at least about 70 percent, and even more preferably at least about 90 percent of the proteolytic activity of the protease protein is inhibited by a serine protease inhibitor.

An isolated protein of the present invention can be produced in a variety of ways, including recovering such a protein from a flea midgut and producing such a protein recombinantly. In one embodiment, a flea midgut protease can be recovered by methods heretofore disclosed for obtaining a soluble flea midgut preparation. A flea midgut protease protein can be further purified from a disrupted flea midgut by a number of techniques known to those skilled in the art, including, but not limited to, affinity chromatography, ion exchange chromatography, filtration, electrophoresis (e.g., standard, capillary and flow-through electrophoresis), hydrophobic interaction chromatography, gel filtration chromatography, reverse phase chromatography, concanavalin A chromatography, chromatofocusing and differential solubilization. In one embodiment, a flea midgut protease is purified using protease inhibitor affinity chromatography, an example of which is disclosed in the Examples section.

Another embodiment of the present invention is a method to produce an isolated protein of the present invention using recombinant DNA technology. Such a method includes the steps of (a) culturing a recombinant cell comprising a nucleic acid molecule encoding a protein of the present invention to produce the protein and (b) recovering the protein therefrom. Details on producing recombinant cells and culturing thereof are presented below. The phrase "recovering the protein" refers simply to collecting the whole fermentation medium containing the protein and need not imply additional steps of separation or purification. Proteins of the present invention can be purified using a variety of standard protein purification techniques, as heretofore disclosed.

Isolated proteins of the present invention are preferably retrieved in "substantially pure" form. As used herein, "substantially pure" refers to a purity that allows for the effective use of the protein as a vaccine. A vaccine for animals, for example, should exhibit no substantial toxicity and should be capable of stimulating the production of antibodies in a vaccinated animal.

Another embodiment of the present invention is an isolated nucleic acid molecule capable of hybridizing under stringent conditions with a gene encoding a flea protease present in a flea midgut. Such a nucleic acid molecule is also referred to herein as a flea protease nucleic acid molecule. Particularly preferred is an isolated nucleic acid molecule that hybridizes under stringent conditions with a flea serine protease gene or with a flea aminopeptidase gene. The characteristics of such genes are disclosed herein. In accordance with the present invention, an isolated nucleic acid molecule is a nucleic acid molecule that has been removed from its natural milieu (i.e., that has been subject to human manipulation). As such, "isolated" does not reflect the extent to which the nucleic acid molecule has been purified. An isolated nucleic acid molecule can include DNA, RNA, or derivatives of either DNA or RNA.

As stated above, a flea protease gene includes all nucleic acid sequences related to a natural flea protease gene such as regulatory regions that control production of a flea protease protein encoded by that gene (such as, but not limited to, transcription, translation or post-translation control regions) as well as the coding region itself. A nucleic acid molecule of the present invention can be an isolated natural flea protease nucleic acid molecule or a homologue thereof. A nucleic acid molecule of the present invention can include one or more regulatory regions, full-length or partial coding regions, or combinations thereof. The minimal size of a flea protease nucleic acid molecule of the present invention is the minimal size capable of forming a stable hybrid under stringent hybridization conditions with a corresponding natural gene. Flea protease nucleic acid molecules can also include a nucleic acid molecule encoding a hybrid protein, a fusion protein, a multivalent protein or a truncation fragment.

An isolated nucleic acid molecule of the present invention can be obtained from its natural source either as an entire (i.e., complete) gene or a portion thereof capable of forming a stable hybrid with that gene. As used herein, the phrase "at least a portion of" an entity refers to an amount of the entity that is at least sufficient to have the functional aspects of that entity. For example, at least a portion of a nucleic acid sequence, as used herein, is an amount of a nucleic acid sequence capable of forming a stable hybrid with the corresponding gene under stringent hybridization conditions.

An isolated nucleic acid molecule of the present invention can also be produced using recombinant DNA technology (e.g., polymerase chain reaction (PCR) amplification, cloning) or chemical synthesis. Isolated flea protease nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode a flea protease protein of the present invention or to form stable hybrids under stringent conditions with natural nucleic acid molecule isolates.

A flea protease nucleic acid molecule homologue can be produced using a number of methods known to those skilled in the art (see, for example, Sambrook et al., ibid.). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid (e.g., the ability of a homologue to elicit an immune response against a flea protease and/or to have proteolytic activity) and/or by hybridization with isolated flea protease nucleic acids under stringent conditions.

An isolated flea protease nucleic acid molecule of the present invention can include a nucleic acid sequence that encodes at least one flea protease protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding an flea protease protein.

One embodiment of the present invention is a flea protease nucleic acid molecule of the present invention that is capable of hybridizing under stringent conditions to a nucleic acid that encodes at least a portion of a flea protease or a homologue thereof. Preferred is a flea protease nucleic acid molecule that includes a nucleic acid sequence having at least about 65 percent, preferably at least about 75 percent, more preferably at least about 85 percent, and even more preferably at least about 95 percent homology with the corresponding region(s) of the nucleic acid sequence encoding at least a portion of a flea protease protein. Particularly preferred is a flea protease nucleic acid molecule capable of encoding at least a portion of a flea protease that naturally is present in flea midguts and preferably is included in a soluble flea midgut preparation of the present invention. Examples of nucleic acid molecules of the present invention are disclosed in the Examples section.

A preferred flea serine protease nucleic acid molecule of the present invention is a nucleic acid molecule that hybridizes under stringent hybridization conditions with at least one of the following nucleic acid molecules: nfSP1, nfSP2, nfSP3, nfSP4, nfSP5, nfSP6, nfSP7, nfSP8, nfSP9, nfSP10, nfSP11, nfSP12, nfSP13, nfSP14, nfSP15, nfSP16 and/or nfSP17. More preferred is a nucleic acid molecule that hybridizes under stringent hybridization conditions with at least one of the following nucleic acid molecules: $nfSP4_{672}$, $nfSP1_{156}$, $nfSP2_{168}$, $nfSP3_{177}$, $nfSP4_{156}$, $nfSP5_{159}$, $nfSP6_{168}$, $nfSP7_{159}$, $nfSP8_{186}$, $nfSP9_{168}$, $nfSP10_{120}$, and/or $nfSP11_{162}$. Even more preferred are nucleic acid molecules that include nfSP1, nfSP2, nfSP3, nfSP4, nfSP5, nfSP6, nfSP7, nfSP8, nfSP9, nfSP10, nfSP11, nfSP12, nfSP13, nfSP14, nfSP15, nfSP16 and/or nfSP17, and even more particularly, $nfSP4_{672}$, $nfSP1_{156}$, $nfSP2_{168}$, $nfSP3_{177}$, $nfSP4_{156}$, $nfSP5_{159}$, $nfSP6_{168}$, $nfSP7_{159}$, $nfSP8_{186}$, $nfSP9_{168}$, $nfSP10_{120}$, and/or $nfSP11_{162}$.

Particularly preferred flea serine protease nucleic acid molecules include at least one of the following sequences: SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, and/or nucleic acid sequences disclosed in Table 2. Also preferred are allelic variants of such nucleic acid molecules.

A preferred flea aminopeptidase nucleic acid molecule of the present invention is a nucleic acid molecule that hybridizes under stringent hybridization conditions with $nfAP_{453}$. More preferred is an aminopeptidase nucleic acid molecule that includes $nfAP_{453}$. Particularly preferred is a nucleic acid molecule that includes nucleic acid sequence SEQ ID NO:50 or an allelic variant thereof.

Knowing a nucleic acid molecule of a flea protease protein of the present invention allows one skilled in the art to make copies of that nucleic acid molecule as well as to obtain a nucleic acid molecule including additional portions of flea protease protein-encoding genes (e.g., nucleic acid molecules that include the translation start site and/or transcription and/or translation control regions), and/or flea protease nucleic acid molecule homologues. Knowing a portion of an amino acid sequence of a flea protease protein of the present invention allows one skilled in the art to clone nucleic acid sequences encoding such a flea protease protein. In addition, a desired flea protease nucleic acid molecule can be obtained in a variety of ways including screening appropriate expression libraries with antibodies which bind to flea protease proteins of the present invention; traditional cloning techniques using oligonucleotide probes of the present invention to screen appropriate libraries or DNA; and PCR amplification of appropriate libraries, or RNA or DNA using oligonucleotide primers of the present invention (genomic and/or cDNA libraries can be used). To isolate flea protease nucleic acid molecules, preferred cDNA libraries include cDNA libraries made from unfed whole fleas, fed whole fleas, fed flea midguts, unfed flea midguts, and flea salivary glands. Techniques to clone and amplify genes are disclosed, for example, in Sambrook et al., ibid. The Examples section includes examples of the isolation of cDNA sequences encoding flea protease proteins of the present invention.

The present invention also includes nucleic acid molecules that are oligonucleotides capable of hybridizing, under stringent conditions, with complementary regions of other, preferably longer, nucleic acid molecules of the present invention that encode at least a portion of a flea protease protein. oligonucleotides of the present invention can be RNA, DNA, or derivatives of either. The minimal size of such oligonucleotides is the size required to form a stable hybrid between a given oligonucleotide and the complementary sequence on another nucleic acid molecule of the present invention. Minimal size characteristics are disclosed herein. The size of the oligonucleotide must also be sufficient for the use of the oligonucleotide in accordance with the present invention. Oligonucleotides of the present invention can be used in a variety of applications including, but not limited to, as probes to identify additional nucleic acid molecules, as primers to amplify or extend nucleic acid molecules or in therapeutic applications to inhibit flea protease production. Such therapeutic applications include the use of such oligonucleotides in, for example, antisense-, triplex formation-, ribozyme- and/or RNA drug-based technologies. The present invention, therefore, includes such oligonucleotides and methods to interfere with the production of flea protease proteins by use of one or more of such technologies.

The present invention also includes a recombinant vector, which includes a flea protease nucleic acid molecule of the present invention inserted into any vector capable of delivering the nucleic acid molecule into a host cell. Such a vector contains heterologous nucleic acid sequences, that is nucleic acid sequences that are not naturally found adjacent to flea protease nucleic acid molecules of the present invention. The vector can be either RNA or DNA, either prokaryotic or eukaryotic, and typically is a virus or a plasmid. Recombinant vectors can be used in the cloning, sequencing, and/or otherwise manipulating of flea protease nucleic acid molecules of the present invention. One type of recombinant vector, herein referred to as a recombinant molecule and described in more detail below, can be used in the expression of nucleic acid molecules of the present invention. Preferred recombinant vectors are capable of replicating in the transformed cell. Preferred nucleic acid molecules to include in recombinant vectors of the present invention are disclosed herein.

As heretofore disclosed, one embodiment of the present invention is a method to produce a flea protease protein of the present invention by culturing a cell capable of expressing the protein under conditions effective to produce the protein, and recovering the protein. A preferred cell to culture is a recombinant cell that is capable of expressing the flea protease protein, the recombinant cell being produced by transforming a host cell with one or more nucleic acid molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a host cell are disclosed herein.

Suitable host cells to transform include any cell that can be transformed and that can express the introduced flea protease protein. Such cells are, therefore, capable of producing flea protease proteins of the present invention after being transformed with at least one nucleic acid molecule of the present invention. Host cells can be either untransformed cells or cells that are already transformed with at least one nucleic acid molecule. Suitable host cells of the present invention can include bacterial, fungal (including yeast), insect, animal and plant cells. Preferred host cells include bacterial, yeast, insect and mammalian cells, with bacterial (e.g., *E. coli*) and insect (e.g., Spodoptera) cells being particularly preferred.

A recombinant cell is preferably produced by transforming a host cell with one or more recombinant molecules, each comprising one or more nucleic acid molecules of the present invention operatively linked to an expression vector containing one or more transcription control sequences. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, insect, animal, and/or plant cells. As such, nucleic acid molecules of the present invention can be operatively linked to expression vectors containing regulatory sequences such as promoters, operators, repressors, enhancers, termination sequences, origins of replication, and other regulatory sequences that are compatible with the recombinant cell and that control the expression of nucleic acid molecules of the present invention. As used herein, a transcription control sequence includes a sequence which is capable of controlling the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, helminth, insect and mammalian cells, such as, but not limited to, tac, lac, trp, trc, oxy-pro, omp/lpp, rrnB, bacteriophage lambda ($\lambda$) (such as $\lambda p_L$ and $\lambda p_R$ and fusions that include such promoters), bacteriophage T7, T7lac, bacteriophage T3, bacteriophage SP6, bacteriophage SP01, metallothionein, alpha mating factor, Pichia alcohol oxidase, alphavirus subgenomic promoters (such as Sindbis virus subgenomic promoters), baculovirus, *Heliothis zea* insect virus, vaccinia virus, herpesvirus, poxvirus, adenovirus, simian virus 40, retrovirus actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with a DNA sequence encoding a flea protease protein.

Expression vectors of the present invention may also contain secretory signals (i.e., signal segment nucleic acid sequences) to enable an expressed flea protease protein to be secreted from the cell that produces the protein. Suitable signal segments include a flea protease protein signal segment or any heterologous signal segment capable of directing the secretion of a flea protease protein, including fusion proteins, of the present invention. Preferred signal segments include, but are not limited to, flea protease, tissue plasminogen activator (t-PA), interferon, interleukin, growth hormone, histocompatibility and viral envelope glycoprotein signal segments.

Expression vectors of the present invention may also contain fusion sequences which lead to the expression of inserted nucleic acid molecules of the present invention as fusion proteins. Inclusion of a fusion sequence as part of a flea protease nucleic acid molecule of the present invention can enhance the stability during production, storage and/or use of the protein encoded by the nucleic acid molecule. Furthermore, a fusion segment can function as a tool to simplify purification of a flea protease protein, such as to enable purification of the resultant fusion protein using affinity chromatography. A suitable fusion segment can be a domain of any size that has the desired function (e.g., increased stability and/or purification tool). It is within the scope of the present invention to use one or more fusion segments. Fusion segments can be joined to amino and/or carboxyl termini of a flea protease protein. Linkages between fusion segments and flea protease proteins can be constructed to be susceptible to cleavage to enable straight-forward recovery of the flea protease proteins. Fusion proteins are preferably produced by culturing a recombinant cell transformed with a fusion nucleic acid sequence that encodes a protein including the fusion segment attached to either the carboxyl and/or amino terminal end of a flea protease protein.

A recombinant molecule of the present invention is a molecule that can include at least one of any nucleic acid molecule heretofore described operatively linked to at least one of any transcription control sequence capable of effectively regulating expression of the nucleic acid molecule(s) in the cell to be transformed. A preferred recombinant molecule includes one or more nucleic acid molecules of the present invention, with those that encode one or more flea protease proteins, and particularly one or more flea serine protease and/or aminopeptidase proteins, being more preferred. Similarly, a preferred recombinant cell includes one or more nucleic acid molecules of the present invention, with those that encode one or more flea protease proteins, and particularly one or more flea serine protease and/or aminopeptidase proteins, being more preferred.

It may be appreciated by one skilled in the art that use of recombinant DNA technologies can improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant protein production during fermentation. The activity of an expressed recombinant protein of the present invention may be improved by fragmenting, modifying, or derivatizing the resultant protein.

In accordance with the present invention, recombinant cells can be used to produce flea protease proteins of the present invention by culturing such cells under conditions effective to produce such a protein, and recovering the protein. Effective conditions to produce a protein include, but are not limited to, appropriate media, bioreactor, temperature, pH and oxygen conditions that permit protein production. An appropriate, or effective, medium refers to any medium in which a cell of the present invention, when cultured, is capable of producing a flea protease protein. Such a medium is typically an aqueous medium comprising assimilable carbohydrate, nitrogen and phosphate sources, as well as appropriate salts, minerals, metals and other nutrients, such as vitamins. The medium may comprise complex nutrients or may be a defined minimal medium.

Cells of the present invention can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art.

Depending on the vector and host system used for production, resultant flea protease proteins may either remain within the recombinant cell; be secreted into the fermentation medium; be secreted into a space between two cellular membranes, such as the periplasmic space in *E. coli*; or be retained on the outer surface of a cell or viral membrane. Methods to purify such proteins are heretofore disclosed.

The present invention also includes isolated anti-flea protease antibodies and their use to reduce flea infestation on a host animal as well as in the environment of the animal. An anti-flea protease antibody is an antibody capable of selectively binding to a protease present in a flea midgut, including female and male fed midguts as well as female and male unfed midguts. An anti-flea protease antibody preferably binds to the protease in such a way as to reduce the proteolytic activity of that protease.

Isolated antibodies are antibodies that have been removed from their natural milieu. The term "isolated" does not refer to the state of purity of such antibodies. As such, isolated antibodies can include anti-sera containing such antibodies, or antibodies that have been purified to varying degrees. As used herein, the term "selectively binds to" refers to the ability of such antibodies to preferentially bind to the protease against which the antibody was raised (i.e., to be able to distinguish that protease from unrelated components in a mixture.). Binding affinities typically range from about $10^3$ $M^{-1}$ to about $10^{12}$ $M^{-1}$. Binding can be measured using a variety of methods known to those skilled in the art including immunoblot assays, immunoprecipitation assays, radioimmunoassays, enzyme immunoassays (e.g., ELISA), immunofluorescent antibody assays and immunoelectron microscopy; see, for example, Sambrook et al., ibid.

Antibodies of the present invention can be either polyclonal or monoclonal antibodies. Antibodies of the present invention include functional equivalents such as antibody fragments and genetically-engineered antibodies, including single chain antibodies, that are capable of selectively binding to at least one of the epitopes of the protein used to obtain the antibodies. Antibodies of the present invention also include chimeric antibodies that can bind to more than one epitope. Preferred antibodies are raised in response to proteins that are encoded, at least in part, by a flea protease nucleic acid molecule of the present invention.

Anti-flea antibodies of the present invention include antibodies raised in an animal administered a flea protease vaccine of the present invention that exert their effect when fleas feed from the vaccinated animal's blood containing such antibodies. Anti-flea antibodies of the present invention also include antibodies raised in an animal against one or more flea protease proteins, or soluble flea midgut preparations, of the present invention that are then recovered from the animal using techniques known to those skilled in the art. Yet additional antibodies of the present invention are produced recombinantly using techniques as heretofore disclosed for flea protease proteins of the present invention. Antibodies produced against defined proteins can be advantageous because such antibodies are not substantially contaminated with antibodies against other substances that might otherwise cause interference in a diagnostic assay or side effects if used in a therapeutic composition.

Anti-flea protease antibodies of the present invention have a variety of uses that are within the scope of the present invention. For example, such antibodies can be used in a composition of the present invention to passively immunize an animal in order to protect the animal from flea infestation. Anti-flea antibodies can also be used as tools to screen expression libraries and/or to recover desired proteins of the present invention from a mixture of proteins and other contaminants. Furthermore, antibodies of the present invention can be used to target cytotoxic agents to fleas in order to kill fleas. Targeting can be accomplished by conjugating (i.e., stably joining) such antibodies to the cytotoxic agents using techniques known to those skilled in the art.

A preferred anti-flea protease antibody of the present invention can selectively bind to, and preferentially reduce the proteolytic activity of, a flea serine protease, a flea metalloprotease, a flea aspartic acid protease and/or a flea cysteine protease. More preferred anti-flea protease antibodies include anti-flea serine protease antibodies, anti-flea metalloprotease antibodies, and anti-flea aminopeptidase antibodies. Particularly preferred are anti-flea serine protease antibodies and anti-flea aminopeptidase antibodies, including those raised against flea serine protease proteins or flea aminopeptidase proteins of the present invention.

The present invention also includes the use of protease inhibitors that reduce proteolytic activity of flea proteases to reduce flea infestation of animals and the surrounding environment. As used herein, protease inhibitors are compounds that interact directly with a protease thereby inhibiting that protease's activity, usually by binding to or otherwise interacting with the protease's active site. Protease inhibitors are usually relatively small compounds and as such differ from anti-protease antibodies that interact with the active site of a protease.

Protease inhibitors can be used directly as compounds in compositions of the present invention to treat animals as long as such compounds are not harmful to the animals being treated. Protease inhibitors can also be used to identify preferred types of flea proteases to target using compositions of the present invention. For example, the inventors have shown herein the predominance of serine proteases in flea midguts, particularly in soluble flea midgut preparations, using protease inhibitors. Such knowledge suggests that effective reduction of flea infestation of an animal can be achieved using serine protease vaccines, anti-flea serine protease antibodies and other inhibitors of serine protease synthesis and activity that can be tolerated by the animal. That other proteases are also present in flea midguts according to the present invention also suggests targeting such proteases. Methods to use protease inhibitors are known to those skilled in the art; examples of such methods are disclosed herein.

In one embodiment, a protease inhibitor that can be used in a composition of the present invention to treat an animal is identified by a method including the following steps: (a) identifying candidate (i.e., putative, possible) inhibitor compounds by testing the efficacy of one or more protease inhibitors (i) in vitro for their ability to inhibit flea protease activity and/or (ii) in a flea feeding assay for their ability to reduce the survival and/or fecundity of fleas by adding the inhibitors to the blood meal of a flea being maintained, for example, in a feeding system, such as that described by Wade et al., 1988, *J.Med Entomol.* 25, 186–190; and (b) testing the efficacy of the candidate inhibitor compounds in animals infested with fleas. Although one does not need both in vitro assay data and flea feeding assay data to determine which candidate compounds to administer to animals, evaluation of both sets of data is preferred since data from neither of the assays necessarily predicts data to be obtained from the other assay. For example, candidate compounds identified using the in vitro assay may work "in the test tube" but may not work in vivo for a number of reasons, including the presence of interfering components in the blood meal that inhibit the activity of such compounds; e.g., although aprotinin can inhibit at least some flea serine proteases in vitro, aprotinin does not work well in the presence of serum proteins, such as are found in the blood. Furthermore, candidate inhibitor compounds identified by the flea feeding assays can include not only desired compounds but also compounds that reduce the viability and/or fecundity of fleas due to general toxicity (e.g., affecting the mitochondria of fleas).

In another embodiment, protease inhibitors are used in the purification of corresponding proteases by, for example, affinity chromatography, in which, a protease inhibitor is incubated with a mixture containing a desired protease under conditions that the inhibitor forms a complex with the protease. The protease can then be recovered from the complex. The protease inhibitor can be attached to a solid support and/or be labelled with, for example, a radioactive, fluorescent, or enzymatic tag that can be used to detect and/or recover the complex.

Suitable protease inhibitors to use in accordance with the present invention include serine protease inhibitors, metalloprotease inhibitors, aspartic acid protease inhibitors, cysteine protease inhibitors, and/or aminopeptidase inhibitors. Preferred protease inhibitors include serine protease inhibitors, metalloprotease inhibitors and aminopeptidase inhibitors, particularly those that are broad spectrum inhibitors. More preferred are broad spectrum serine protease inhibitors.

There is a wide variety of protease inhibitors, as is known to one skilled in the art. Examples include, but are not limited to, AEBSF, aprotinin, bestatin, chloromethyl ketones TLCK (Nα-p-tosyl-L-lysine chloromethyl ketone) and TPCK (N-tosyl-L-phenylalanine chloromethyl ketone), chymostatin, cystatin, 3'4-dichloroisocoumarin, E-64 (transepoxysuccinyl-L-leucylamido-( 4-guanidino)butane), EDTA (ethylenediaminetetraacetic acid), leupeptin, methyl ketones having a variety of leaving groups, oxidized L-leucinethiol, pepstatin, 1,10-orthophenanthroline, phosphoramidon, soybean trypsin/chymotrypsin inhibitor and soybean trypsin inhibitor. Preferred protease inhibitors for use in the present invention include AEBSF, bestatin, E-64 leupeptin, pepstatin, 1,10-orthophenanthroline, phosphoramidon, TLCK and TPCK, with AEBSF (a broad spectrum serine protease inhibitor), bestatin (an inhibitor of leucine aminopeptidase) and 1,10-orthophenanthroline (a broad spectrum metalloprotease inhibitor) being particularly preferred.

Protease inhibitors can be produced using methods known to those skilled in the art. Protein- or peptide-based protease inhibitors, such as cystatin or small peptides comprising a protease substrate, can be produced recombinantly and modified as necessary.

The present invention also includes the use of proteolytically active flea protease proteins of the present invention to identify additional protease inhibitors, and preferably protease inhibitor compounds that can be included in a composition of the present invention to be administered to animals. A method to identify a flea protease inhibitor includes the steps of (a) contacting (e.g., combining, mixing) an isolated flea protease protein with a putative (i.e., candidate) inhibitory compound under conditions in which, in the absence of the compound, the protein has proteolytic activity, and (b) determining if the putative inhibitory compound inhibits the proteolytic activity of the protein. Putative inhibitory compounds to screen include organic molecules, antibodies (including functional equivalents thereof) and substrate analogs. Methods to determine protease activity are known to those skilled in the art, as heretofore disclosed. Particularly preferred for use in identifying inhibitors are flea serine protease proteins and flea aminopeptidase proteins of the present invention.

The present invention also includes a test kit to identify a compound capable of inhibiting flea protease activity. Such a test kit includes an isolated flea protease protein having proteolytic activity and a means for determining the extent of inhibition of proteolytic activity in the presence of (i.e., effected by) a putative inhibitory compound.

The present invention also includes inhibitors isolated by such a method, and/or test kit, and their use to inhibit any flea protease that is susceptible to such an inhibitor.

It is to be appreciated that the present invention also includes mimetopes of compounds of the present invention that can be used in accordance with methods as disclosed for compounds of the present invention. As used herein, a mimetope of a proteinaceous compound of the present invention (e.g., a flea protease protein, an anti-flea protease antibody, a proteinaceous inhibitor of protease activity or synthesis) refers to any compound that is able to mimic the activity of that proteinaceous compound, often because the mimetope has a structure that mimics the proteinaceous compound. For example, a mimetope of a flea protease protein is a compound that has an activity similar to that of an isolated flea protease protein of the present invention. Mimetopes can be, but are not limited to: peptides that have been modified to decrease their susceptibility to degradation; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

The present invention includes therapeutic compositions, also referred to herein as compositions, that include a (i.e., at least one) compound of the present invention. Preferred compounds to include in a composition of the present invention include flea protease vaccines, anti-flea protease antibodies and/or protease inhibitors as disclosed herein. Such a therapeutic composition can protect an animal from flea infestation by reducing flea protease activity, thereby reducing flea burden on the animal and in the environment of the animal.

Particularly preferred therapeutic compositions of the present invention include at least one of the following compounds: an isolated flea serine protease protein or a mimetope thereof; an isolated flea serine protease nucleic acid molecule that hybridizes under stringent hybridization conditions with a flea serine protease gene; an isolated antibody that selectively binds to a flea serine protease protein; an inhibitor of flea serine protease activity identified by its ability to inhibit flea serine protease activity; an isolated flea aminopeptidase protein or a mimetope thereof; an isolated flea aminopeptidase nucleic acid molecule that hybridizes under stringent hybridization conditions with a flea aminopeptidase gene; an isolated antibody that selectively binds to a flea aminopeptidase protein; and an inhibitor of flea aminopeptidase activity identified by its ability to inhibit flea aminopeptidase activity.

Another embodiment of the present invention is a therapeutic composition that includes a first compound that reduces flea protease activity and a second compound that reduces flea burden by a method other than by reducing flea protease activity. The present invention also includes a method to protect an animal from flea infestation by administering to the animal such a composition. The first compound of such a composition by effectively reducing flea protease activity in the midgut, enhances the activity of the second compound. While not being bound by theory, it is believed that a number of anti-flea treatments, particularly those that are proteinaceous, are not very effective because they are degraded in the flea midgut. The present invention permits the effective use of such anti-flea treatments by reducing proteolytic degradation of such treatments by the flea midgut.

Preferred first compounds to include in such a composition include flea protease vaccines, anti-flea protease antibodies and/or protease inhibitors as disclosed herein.

Suitable second compounds include any anti-flea agent(s), including, but not limited to, proteinaceous compounds, insecticides and flea collars. Preferred second compounds are proteinaceous compounds that effect active immunization (e.g., antigen vaccines), passive immunization (e.g., antibodies), or that otherwise inhibit a flea activity that when inhibited can reduce flea burden on and around an animal. Examples of second compounds include a compound that inhibits binding between a flea membrane protein and its ligand (e.g., a compound that inhibits flea ATPase activity or a compound that inhibits binding of a peptide or steroid hormone to its receptor), a compound that inhibits hormone (including peptide or steroid hormones) synthesis, a compound that inhibits vitellogenesis (including production of vitellin and transport and maturation thereof into a major egg yolk protein), a compound that inhibits fat body function, a compound that inhibits flea muscle action, a compound that inhibits the flea nervous system, a compound that inhibits the flea immune system and/or a compound that inhibits flea feeding.

Compositions of the present invention can also include other components such as a pharmaceutically acceptable excipient, an adjuvant, and/or a carrier. For example, compositions of the present invention can be formulated in an excipient that the animal to be treated can tolerate. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, the composition can also include an immunopotentiator, such as an adjuvant or a carrier. Adjuvants are typically substances that generally enhance the immune response of an animal to a specific antigen. Suitable adjuvants include, but are not limited to, Freund's adjuvant; other bacterial cell wall components; aluminum-based salts; calcium-based salts; silica; polynucleotides; toxoids; serum proteins; viral coat proteins; other bacterial-derived preparations; gamma interferon; block copolymer adjuvants, such as Hunter's Titermax adjuvant (Vaxcel™, Inc. Norcross, Ga.); Ribi adjuvants (available from Ribi ImmunoChem Research, Inc., Hamilton, Mont.); and saponins and their derivatives, such as Quil A (available from Superfos Biosector A/S, Denmark). Carriers are typically compounds that increase the half-life of a therapeutic composition in the treated animal. Suitable carriers include, but are not limited to, polymeric controlled release formulations, biodegradable implants, liposomes, bacteria, viruses, oils, esters, and glycols.

One embodiment of the present invention is a controlled release formulation that is capable of slowly releasing a composition of the present invention into an animal. As used herein a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of the treated animal at a constant rate sufficient to attain therapeutic dose levels of the composition to reduce protease activity in fleas feeding from the animal over a period of time ranging from about 1 to about 12 months. A controlled release formulation of the present invention is capable of effecting a treatment for preferably at least about 1 month, more preferably at least about 3 months and even more preferably for at least about 6 months, even more preferably for at least about 9 months, and even more preferably for at least about 12 months.

In order to protect an animal from flea infestation, a therapeutic composition of the present invention is administered to the animal in an effective manner such that the protease activity of fleas feeding from the blood stream of animals treated with the composition is reduced. As such, a treated animal is an animal that is competent to reduce the flea burden by reducing flea protease activity, or by reducing flea protease activity and at least one other flea activity. Preferably, the protease activity is reduced by at least about 50 percent, more preferably by at least about 70 percent and even more preferably by at least about 90 percent. Methods to administer compositions to the animal in order to render the animal competent depend on the nature of the composition and administration regime.

Animals administered a protease vaccine with at least one booster shot usually become competent at about the same time as would be expected for any vaccine treatment. For example, animals administered a booster dose about 4 to 6 weeks after a primary dose usually become competent within another about 3 to 4 weeks. Animals administered a composition including an anti-flea protease antibody or protease inhibitor become competent as soon as appropriate serum levels of the compound are achieved, usually with one to three days.

In a preferred embodiment, a composition of the present invention when administered to a host animal is able to reduce flea viability by at least about 50 percent within at least about 21 days after the fleas begin feeding from the treated animal. (Note that fleas usually live about 40 days to about 50 days on one or more animals.) A more preferred composition when administered to a host animal is able to reduce flea viability by at least about 65 percent within at least about 14 days after the fleas begin feeding from the treated animal. An even more preferred composition when administered to an animal is able to reduce flea viability by at least about 90 percent within at least about 7 days after the fleas begin feeding from the treated animal.

In another preferred embodiment, a composition of the present invention when administered to a host animal is able to reduce flea fecundity (i.e., egg laying ability) by at least about 50 percent, more preferably by at least about 70 percent, and even more preferably by at least about 90 percent, within at least about 30 days after the fleas begin feeding from the treated animal. (Note that fleas usually do not begin laying eggs until about 7 days after taking a blood meal.)

In accordance with the present invention, compositions are administered to an animal in a manner such that the animal becomes competent to reduce flea protease activity in a flea that feeds from the competent; i.e., the animal becomes a treated animal. For example, a flea protease vaccine of the present invention, when administered to an animal in an effective manner, is able to elicit (i.e., stimulate) an immune response that produces an antibody titer in the blood stream of the animal sufficient to reduce flea protease activity. Similarly, an anti-flea protease antibody of the present invention, when administered to an animal in an effective manner, is administered in an amount so as to be present in the animal's blood stream at a titer that is sufficient to reduce flea protease activity. A protease inhibitor compound of the present invention, when administered to an animal in an effective manner, is administered in a manner so as to be present in the animal's blood stream at a concentration that is sufficient to reduce flea protease activity. Oligonucleotide nucleic acid molecules of the present invention can also be administered in an effective manner, thereby reducing expression of flea proteases.

Compositions of the present invention can be administered to animals prior to or during flea infestation. It is to be noted that when vaccines of the present invention are administered to an animal, a time period is required for the animal to elicit an immune response before the animal is competent to inhibit protease activity of fleas feeding from that animal. Methods to obtain an immune response in an animal are known to those skilled in the art.

Acceptable protocols to administer compositions in an effective manner include individual dose size, number of doses, frequency of dose administration, and mode of administration. Determination of such protocols can be accomplished by those skilled in the art. A suitable single dose is a dose that is capable of protecting an animal from flea infestation when administered one or more times over a suitable time period. For example, a preferred single dose of a protease vaccine or a mimetope thereof ranges from about 1 microgram (µg, also denoted ug) to about 10 milligrams (mg) of the composition per kilogram body weight of the animal. Booster vaccinations can be administered from about 2 weeks to several years after the original administration. Booster vaccinations preferably are administered when the immune response of the animal becomes insufficient to protect the animal from flea infestation. A preferred administration schedule is one in which from about 10 µg to about 1 mg of the vaccine per kg body weight of the animal is administered from about one to about two times over a time period of from about 2 weeks to about 12 months. In one embodiment, a booster dose of a composition of the present invention is administered about 4 to 6 weeks after the primary dose, and additional boosters are administered about once or twice a year. Modes of administration can include, but are not limited to, oral, nasal, topical, transdermal, rectal, and parenteral routes. Parenteral routes can include, but are not limited to subcutaneous, intradermal, intravenous, and intramuscular routes.

In another embodiment, a preferred single dose of an anti-flea protease antibody composition or a mimetope thereof ranges from about 1 µg to about 10 mg of the composition per kilogram body weight of the animal. Anti-flea antibodies can be re-administered from about 1 hour to about biweekly for several weeks following the original administration. Booster treatments preferably are administered when the titer of antibodies of the animal becomes insufficient to protect the animal from flea infestation. A preferred administration schedule is one in which from about 10 µg to about 1 mg of an anti-flea protease antibody composition per kg body weight of the animal is administered about every 2 to every 4 weeks. Suitable modes of administration are as disclosed herein and are known to those skilled in the art.

According to one embodiment, a nucleic acid molecule of the present invention can be administered to an animal in a fashion to enable expression of that nucleic acid molecule into a protective protein (e.g., flea protease vaccine, anti-flea protease antibody, or proteinaceous protease inhibitor) or protective RNA (e.g., antisense RNA, ribozyme or RNA drug) in the animal to be protected from disease. Nucleic acid molecules can be delivered to an animal in a variety of methods including, but not limited to, (a) direct injection (e.g., as "naked" DNA or RNA molecules, such as is taught, for example in Wolff et al., 1990, *Science* 247, 1465–1468) or (b) packaged as a recombinant virus particle vaccine or as a recombinant cell vaccine (i.e., delivered to a cell by a vehicle selected from the group consisting of a recombinant virus particle vaccine and a recombinant cell vaccine).

A recombinant virus particle vaccine of the present invention includes a recombinant molecule of the present invention that is packaged in a viral coat and that can be expressed in an animal after administration. Preferably, the recombinant molecule is packaging-deficient. A number of recombinant virus particles can be used, including, but not limited to, those based on alphaviruses, poxviruses, adenoviruses, herpesviruses, and retroviruses.

When administered to an animal, a recombinant virus particle vaccine of the present invention infects cells within the immunized animal and directs the production of a protective protein or RNA nucleic acid molecule that is capable of protecting the animal from disease caused by a parasite of the present invention. A preferred single dose of a recombinant virus particle vaccine of the present invention is from about $1 \times 10^4$ to about $1 \times 10^7$ virus plaque forming units (pfu) per kilogram body weight of the animal. Administration protocols are similar to those described herein for protein-based vaccines.

A recombinant cell vaccine of the present invention includes recombinant cells of the present invention that express at least one protein of the present invention. Preferred recombinant cells include Salmonella, *E. coli*, Mycobacterium, *S. frugiperda*, baby hamster kidney, myoblast G8, COS, MDCK and CRFK recombinant cells, with Salmonella recombinant cells being more preferred. Such recombinant cells can be administered in a variety of ways but have the advantage that they can be administered orally, preferably at doses ranging from about $10^8$ to about $10^{12}$ bacteria per kilogram body weight. Administration protocols are similar to those described herein for protein-based vaccines. Recombinant cell vaccines can comprise whole cells or cell lysates.

Compositions of the present invention can be administered to any animal susceptible to flea infestation, including warm-blooded animals. Preferred animals to treat include mammals and birds, with cats, dogs, humans, cattle, chinchillas, ferrets, goats, mice, minks, rabbits, raccoons, rats, sheep, squirrels, swine, chickens, ostriches, quail and turkeys as well as other furry animals, pets and/or economic food animals, being more preferred. Particularly preferred animals to protect are cats and dogs.

The present invention includes compositions to treat flea infestation by any flea. As such, compositions of the present invention can be derived from any flea species. Preferred fleas to target include fleas of the following genera: Ctenocephalides, cyopsyllus, Diamanus (Oropsylla), Echidnophaga, Nosopsyllus, Pulex, Tunga, and Xenopsylla, with those of the species *Ctenocephalides canis, Ctenocephalides felis, Diamanus montanus, Echidnophaga gallinacea, Nosopsyllus faciatus, Pulex irritans, Pulex simulans, Tunga penetrans* and *Xenopsylla cheopis* being more preferred. Particularly preferred fleas from which to protect animals include fleas of the species *Ctenocephalides felis, Ctenocephalides canis,* and Pulex species (e.g., *Pulex irritans* and *Pulex simulans*). It is also within the scope of the present invention to administer compositions of the present invention directly to fleas.

The present invention also includes the use of compositions of the present invention to reduce infestation by other ectoparasites as well as the use of compositions including protease vaccines, anti-protease antibodies and compounds that inhibit protease synthesis and/or activity derived from any ectoparasite to reduce ectoparasite infestation, particularly controlled release formulations containing such compositions. Preferred ectoparasites to target include arachnids, insects and leeches. More preferred ectoparasites to target include fleas; ticks, including both hard ticks of the family Ixodidae (e.g., Ixodes and Amblyomma) and soft ticks of the family Argasidae (e.g., Ornithodoros, such as *O. parkeri* and *O. turicata*); flies, such as midges (e.g., Culicoides), mosquitos, sand flies, black flies, horse flies, horn flies, deer flies, tsetse flies, stable flies, myiasis-causing flies and biting gnats; ants; spiders, lice; mites; and true bugs, such as bed bugs and kissing bugs, including those carrying Chagas disease. Even more preferred ectoparasites to target include fleas, mosquitos, midges, sandflies, blackflies, ticks and Rhodnius.

The following examples are provided for the purposes of illustration and are not intended to limit the scope of the present invention.

EXAMPLES

Example 1

This Example demonstrates that soluble flea midgut preparations contain serine protease activity as well as leucine aminopeptidase activity.

Using a homogenization/sonication protocol as described in Ser. No. 07/806,482 now U.S. Pat. No. 5,356,622, ibid., followed by an about 2 minute centrifugation step at about 10,000×g, soluble flea midgut preparations were obtained from fed and unfed fleas. Pellets from the centrifugation step were also collected and resuspended for analysis. Also prepared were whole flea lysates. Peptide substrate screening studies using the synthetic chromogenic trypsin substrate BAPNA (Nα-benzoyl-DL-arginine-p-nitroanilide; available from Sigma Chemical Co., St. Louis, Mo.) demonstrated significant proteolytic activity in both soluble flea midgut preparations as well as some proteolytic activity in resuspended midgut pellets. Soluble unfed flea midgut preparations exhibited about 10 times as much activity as did controls (samples to which no flea midgut fractions were added), whereas soluble fed flea midgut preparations exhibited about 20 times as much activity as did controls. Whole flea preparations exhibited about 2 to 3 times as much activity as did controls.

The ability of soluble fed and unfed flea midgut preparations to cleave BAPNA was almost completely inhibited (i.e., nearly 100%) by aprotinin (available from Sigma), whereas PMSF (phenylmethane-7-sulfonyl fluoride; available from Sigma) inhibited such proteolytic activity by about 50%. EDTA inhibited proteolytic activity of the preparations by about 10%, whereas addition of calcium ions stimulated proteolytic activity by about 25%. These results indicate the presence of serine protease activity, and more particularly of trypsin-like activity, in these soluble flea midgut preparations. These results also suggest the presence of serine protease isoforms in the preparations. It is also of interest to note that flea trypsin-like activity appears to be distinctive from that of mosquitos in that mosquito trypsins are not affected by EDTA or calcium ions.

Using a methyl-hemoglobin substrate, the pH optimum of the proteolytic activity in the soluble flea midgut preparations was found to be between pH 7 and pH 9, with a pH of about pH 8 giving the best activity. Such pH optima suggest the presence of serine proteases in soluble flea midgut preparations.

Soluble preparations of both unfed and fed flea midgut soluble preparations also were able to cleave the leucine aminopeptidase specific substrate LPNA (L-leucine-p-nitroanilide; available from Sigma) using standard conditions, indicating the presence of leucine aminopeptidase (LAP) activity in such preparations.

Example 2

The following example evaluated the number of proteases in flea midguts that could be assessed by protease substrate gel analysis.

Protease substrate gels (available from Novex, San Diego, Calif., as Novex Zymogels) were 10% polyacrylamide-SDS gels with 0.1% gelatin. Samples and gels were processed according to Novex instructions. Briefly, samples were diluted in SDS-PAGE sample buffer without reducing agents. Tris-glycine SDS-PAGE was carried out by standard procedures. After electrophoresis, gels were incubated in 0.25% Triton X-100 at room temperature for 30 minutes (min), then in developing buffer (50 mM (millimolar) Tris-HCl pH 7.0, 5 mM $CaCl_2$, 0.02% Brij 35, 0.2 M (molar) NaCl) at room temperature for 30 min, and then incubated with fresh developing buffer at 37° C., usually overnight. Gels were then stained 30 min in 0.5% coomassie R-250, 40% methanol, 10% acetic acid and destained in 40% methanol, 10% acetic acid.

The following flea midguts were dissected directly into sample buffer: 100 midguts from unfed males; 100 midguts from unfed females; 100 midguts from fed males; and 100 midguts from fed females. Samples containing 10 or 20 midguts each were evaluated using protease substrate gel analysis and numerous negative staining bands were observed. The general pattern was the same for female and male midguts, although there appeared to be more activity in gel lanes containing female midguts. There were distinct differences noted between gel lanes containing fed and unfed midguts. There was a definite increase in overall activity in the fed midgut lanes, and, in addition, there were differences in the band patterns.

Fed and unfed female midguts were further evaluated using protease substrate gel analysis and the results are shown in FIG. 1. The protease substrate gel shown in FIG. 1 demonstrates the relative proteolytic activity in 1, 2, 5 or 10 midguts from either fed or unfed female fleas. Specifically, lane 1 contains a set of molecular weight markers. Lanes 2 through 5 contain, respectively, 10, 5, 2 and 1 unfed midguts. Lanes 6 through 9 contain, respectively, 1, 2, 5 and 10 fed midguts. Lane 10 contains 100 μg of dried bovine blood.

Proteolytic activity could easily be detected in one fed or one unfed female midgut, although there was considerably more activity in the fed midgut. Lane 10 evaluated 100 μg of dried bovine blood to assess if the increase in activity seen in the fed midgut lane was due to proteases in the blood meal. No activity was seen in the blood lane.

Example 3

This example evaluated the protease classes present in flea midguts.

Three unfed female midguts and 0.75 fed female midguts were evaluated in duplicate in several protease substrate gels. Each gel was cut in half. Half was processed as described in Example 2, while the other half contained protease inhibitors in all incubation buffers. The following inhibitors were evaluated:

(a) the serine protease inhibitor AEBSF (available from Boehringer Mannheim, Indianapolis, Ind.) was used at a final concentration of 1 mM;

(b) the serine protease inhibitor soybean trypsin inhibitor (available from Sigma) was used at a final concentration of 100 μg/ml (milliliter);

(c) the cysteine and serine protease inhibitor leupeptin (available from Sigma) was used at a final concentration of 10 μg/ml;

(d) the aminopeptidase inhibitor bestatin (available from Sigma) was used at a final concentration of 0.25 mM;

(e) the metalloprotease inhibitor EDTA (available from Sigma) was used at a final concentration of 2 mM; and (f) the cysteine protease E-64 (available from Sigma) was used at a final concentration of 10 μg/ml.

Figure 2:
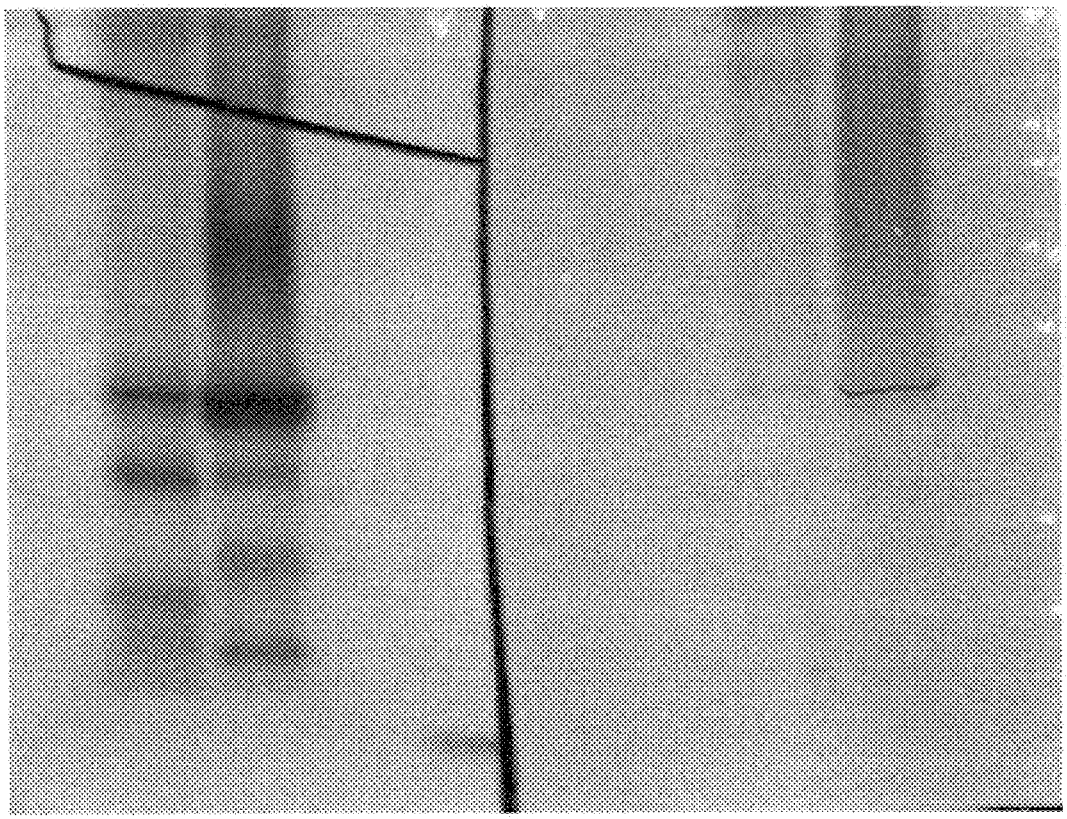
FIG. 2 depicts a protease substrate gel analysis of fed and unfed midgut preparations incubated in the presence or absence of a serine protease inhibitor.

AEBSF, soybean trypsin inhibitor and leupeptin were the only inhibitors to have any effect at the sensitivity of this assay. It was determined that serine proteases were the predominant, if not only, proteases present in the midgut preparations evaluated. FIG. 2 shows a protease substrate gel with fed (lanes 2 and 4) and unfed (lanes 1 and 3) midgut preparations with (lanes 3 and 4) and without (lanes 1 and 2) AEBSF. Residual activity in the inhibitor lanes could have been due to proteolysis that occurred during electrophoresis and prior to saturation of the gel with inhibitor in the incubation buffers.

Example 4

This Example evaluates protease activity contained in a soluble fed midgut preparation of the present invention.

Figure 3:
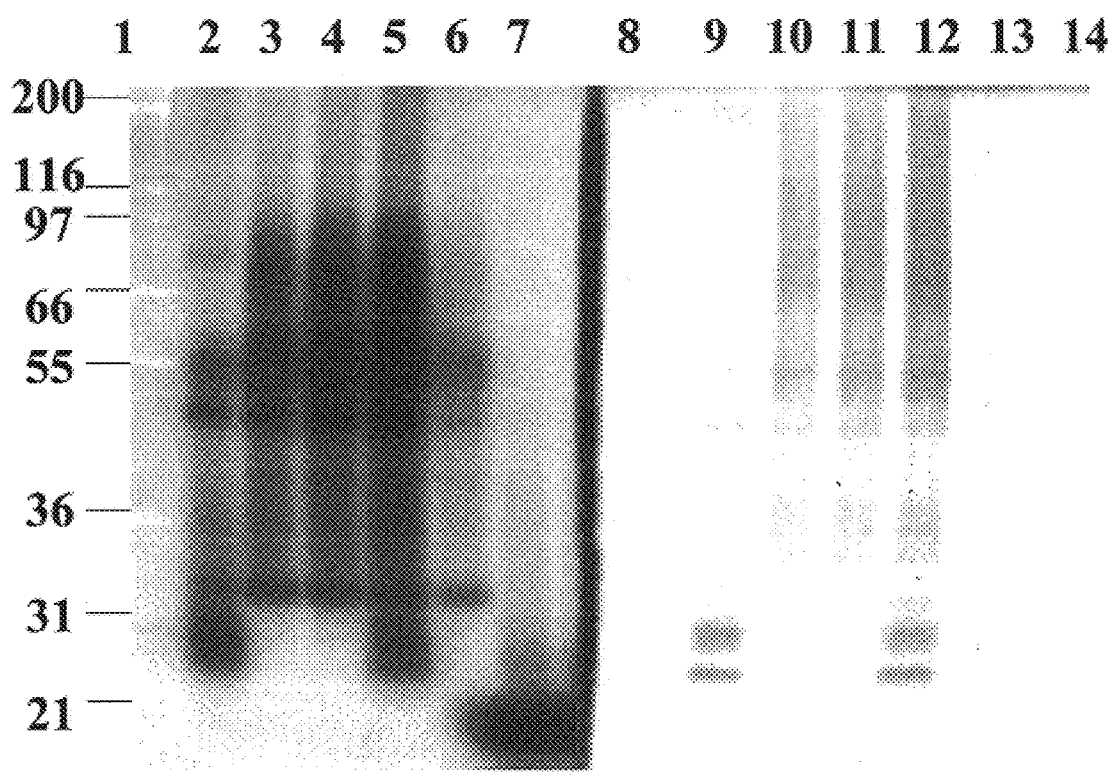
FIG. 3 depicts a protease substrate gel analysis of various fractions obtained in the preparation of a soluble flea midgut preparation incubated in the presence or absence of a serine protease inhibitor.

Mixed-sex fed flea midguts were processed as described in Ser. No. 07/806,482 now U.S. Pat. No. 5,356,622, ibid. Aliquots of several steps of the procedure were evaluated by loading an equivalent of 0.4 midguts per lane of a protease substrate gel as described in Example 2. The results are shown in FIG. 3. Samples were from the low speed supernatant (lanes 2 and 9), sonicated midguts (lanes 3 and 10), high speed supernatant (lanes 4 and 11), combined low and high speed supernatants (FGS) (lanes 5 and 12) and the high speed pellet (lanes 6 and 13). Lanes 7 and 8 contained 50 nanograms (ng) of trypsin as a control. Duplicate lanes were evaluated. The gel was cut in half, and lanes 1–7 were processed as described in Example 2, and lanes 8–14 were processed with 100 μg/ml soybean trypsin inhibitor in all the incubation buffers.

Protease activity was seen in all preparations, the most being observed in the FGS lane (lane 5). It was also evident that the majority of the activity was inhibited by soybean trypsin inhibitor, a serine protease inhibitor.

Example 5

This Example demonstrates the increase in flea midgut protease activity after blood feeding by fleas.

Figure 4:
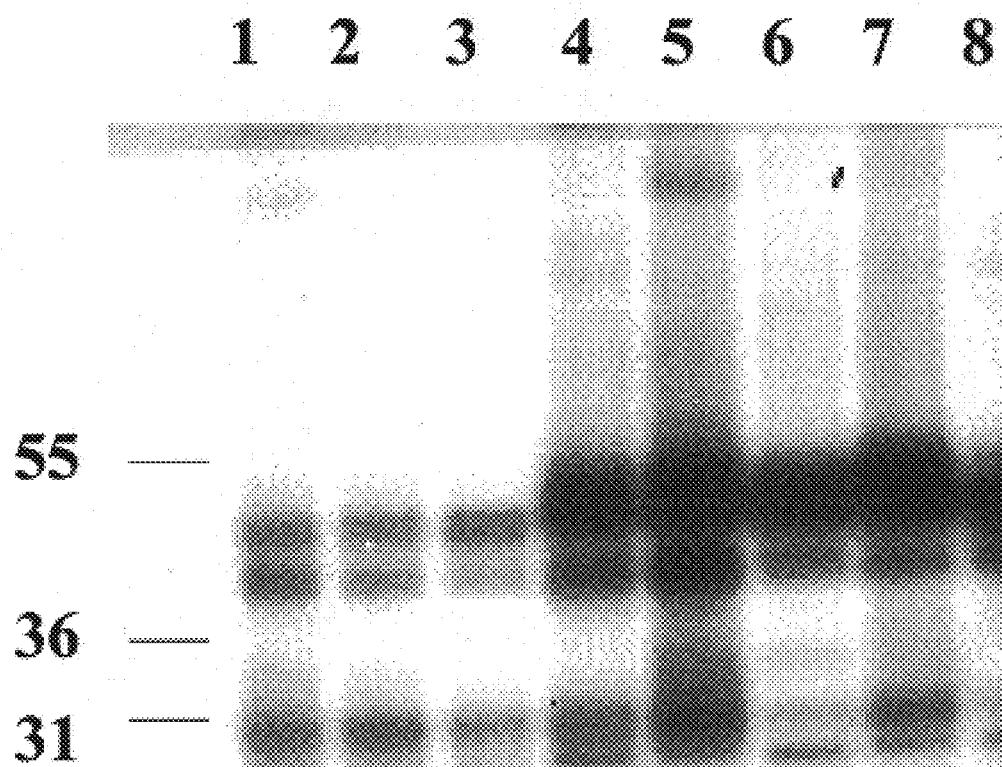
FIG. 4 depicts a protease substrate gel showing midgut protease activity as a function of time after flea blood feeding.
Figure 6:
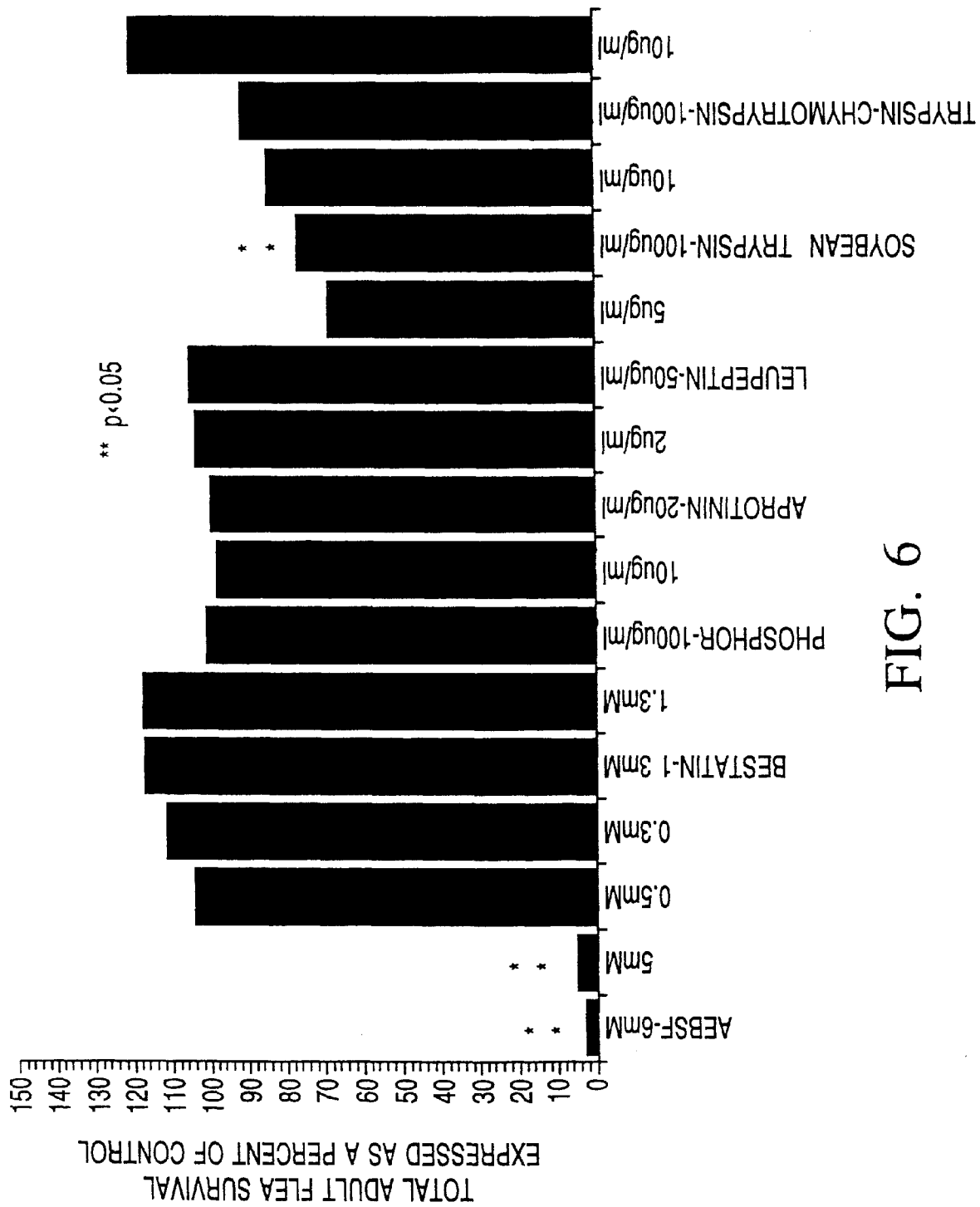
FIG. 6 depicts the mean viability of adult (both male and female) fleas fed blood containing certain protease inhibitors.
Figure 7:
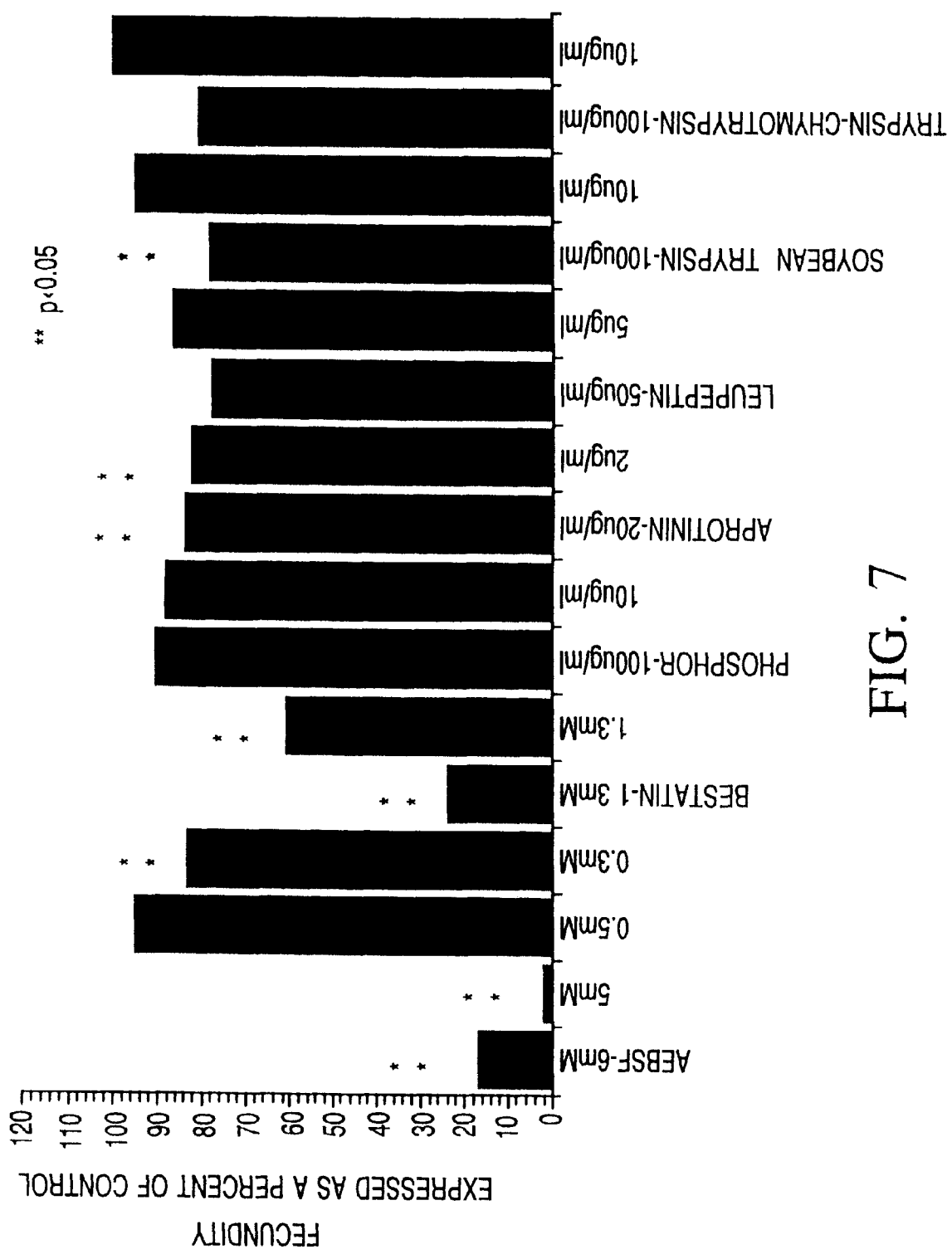
FIG. 7 depicts the mean fecundity of adult female fleas fed blood containing certain protease inhibitors.
Figure 8:
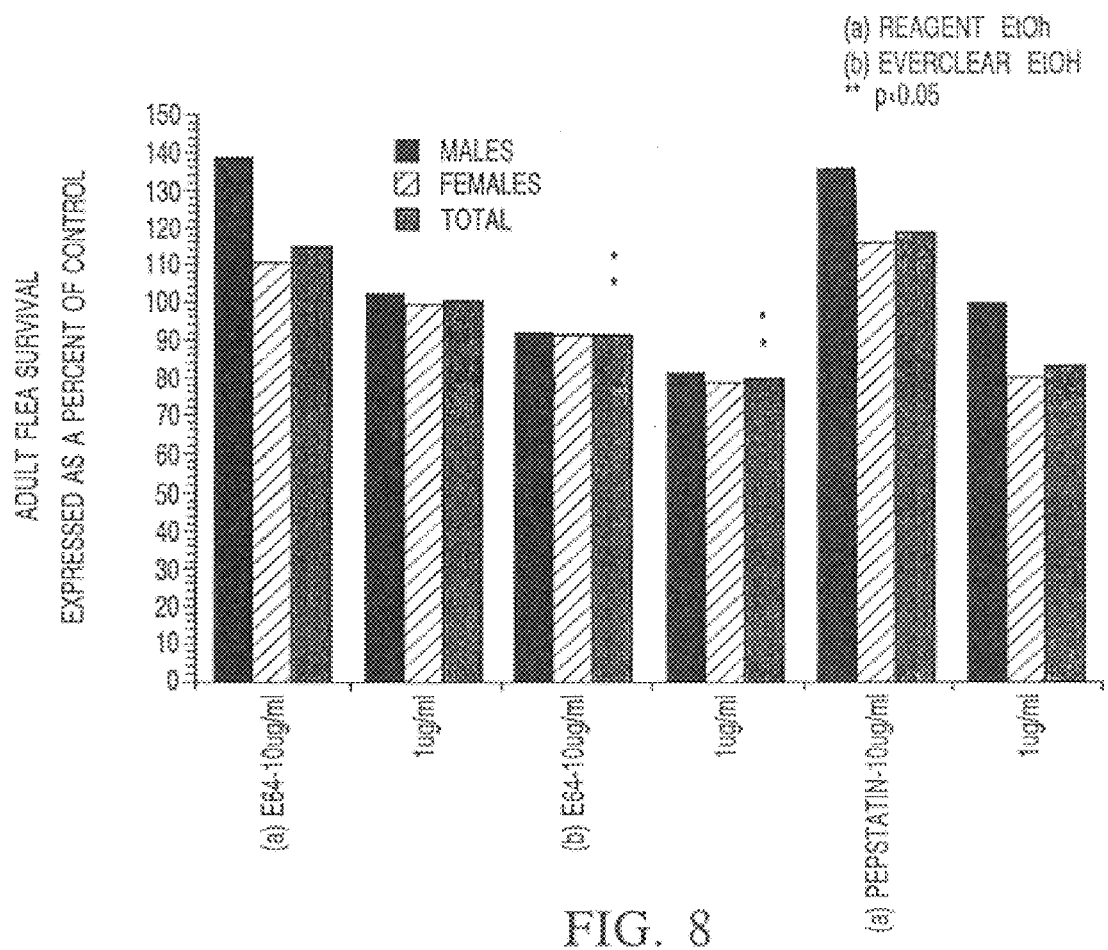
FIG. 8 depicts the mean viability of adult (both male and female) fleas fed blood containing certain protease inhibitors.
Figure 9:
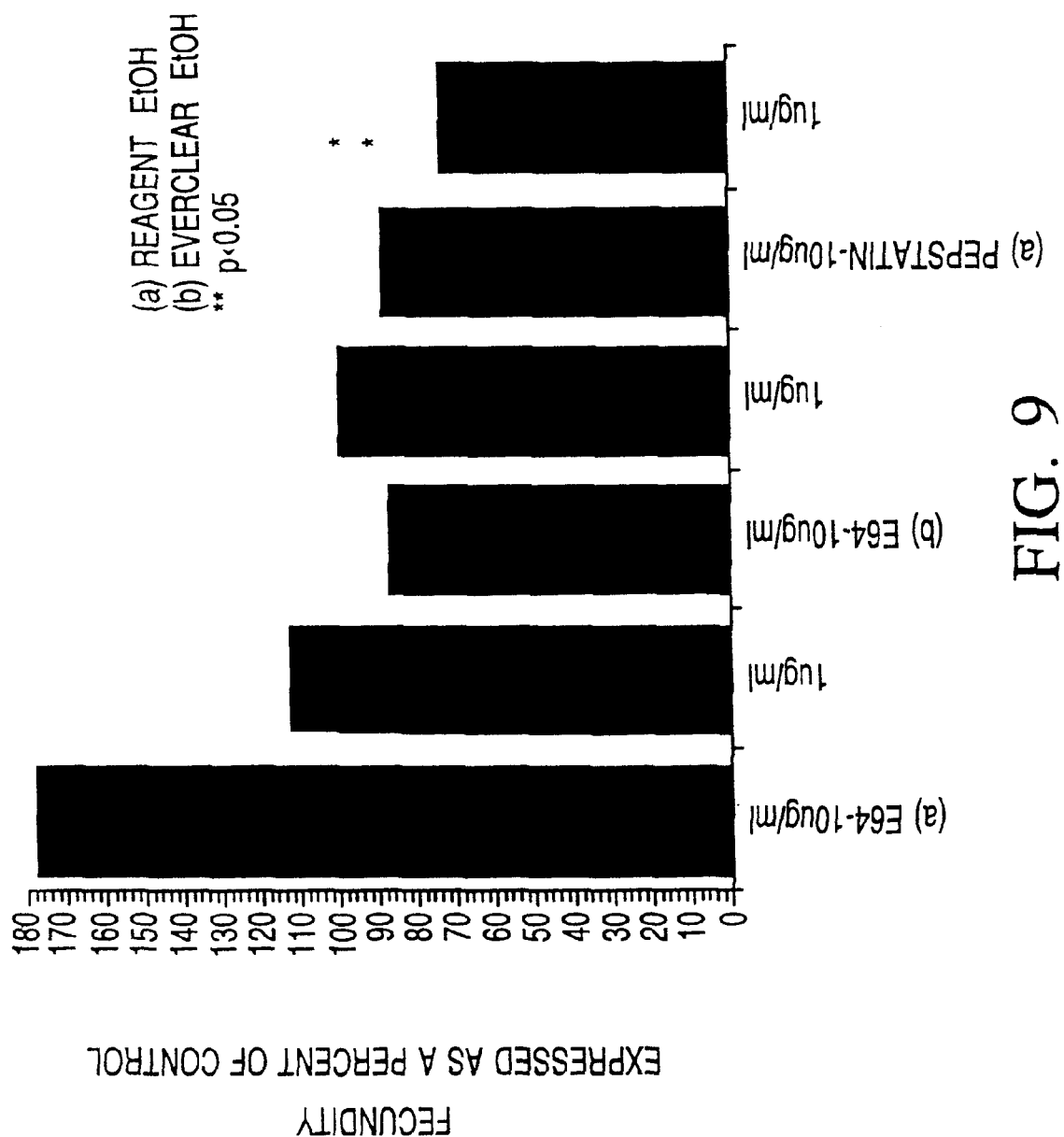
FIG. 9 depicts the mean fecundity of adult female fleas fed blood containing certain protease inhibitors.

Fleas were fed on a dog for 15 minutes. At timed intervals after feeding, two midguts were dissected directly into sample buffer and proteases evaluated by protease substrate gel analysis as described in Example 2. FIG. 4 depicts a gel showing midgut protease activity at 30 min (lane 1), 1 hr (lane 2), 2 hr (lane 3), 4 hr (lane 4), 6 hr (lane 5), 8 hr (lane 6), 24 hr (lane 7) and 56 hr (lane 8) after blood feeding ended.

Increases in proteolytic activity were first observed 2 hr (lane 3) after feeding, although at 4 hr (lane 4) there was a much greater increase in activity noted. This increase in activity was still noticed 56 hr after feeding (lane 8).

Example 6

This Example evaluates the effect of a number of protease inhibitors on flea viability and fecundity in a flea feeding system as described by Wade et al. ibid.

The following protease inhibitors were tested at the indicated final concentrations in blood meals:

(a) Aminopeptidase inhibitor bestatin at 1.3 mM and 13 mM;

(b) Aspartic acid protease inhibitor pepstatin A at 1 μg/ml and 10 μg/ml;

(c) Cysteine protease inhibitor E-64 at 1 μg/ml and 10 μg/ml.

(d) Metalloprotease inhibitor phosphoramidon at 10 μg/ml and 100 μg/ml; and (e) the following serine protease inhibitors:
AEBSF at 0.3 mM, 0.5 mM, 5.0 mM and 6.0 mM;
Aprotinin at 2 μg/ml and 20 μg/ml;
Leupeptin at 5 μg/ml and 50 μg/ml;
Soybean trypsin inhibitor at 10 μg/ml and 100 μg/ml;
Soybean trypsin/chymotrypsin inhibitor at 10 μg/ml and 100 μg/ml;

AEBSF is available from Boehringer Mannheim; all other listed inhibitors are available from Sigma.

Protease inhibitor compounds were tested in groups of 3 to 6 including appropriate control groups. Inhibitors were not tested in groups of common inhibition types. Rather, they were tested in groups based on the diluent needed to dissolve them. (AEBSF, aprotinin, bestatin, leupeptin, phosphoramidon, soybean trypsin inhibitor and soybean trypsin/chymotrypsin inhibitor were dissolved in water; E-64 and pepstatin were dissolved in ethanol). This reduced the number of control (diluent only) groups needed within a particular assay. Inhibitor concentrations were chosen such that the lower concentration used was within the range recommended by the supplier for that inhibitor. The higher concentration was typically 10 times above the lower concentration and was used to look for dose response.

The general protocol for all of the assays was as follows: Approximately 2000 newly emerged adult fleas were placed in feeding chambers to feed on normal blood for about 24 to 48 hr. The fleas were prefed for two reasons: The first was to be certain that only fleas that would feed in the feeding system were used in the comparative study. The second was to prime female fleas for egg laying, since female fleas typically do not begin laying maximal numbers of eggs per day until the third day of feeding.

The prefed fleas were placed in "minifeeder" feeding chambers at a ratio of about 80 female fleas to about 20 male fleas for a total of about 100 fleas per chamber. Actual total number of fleas per chamber varied from about 90 to 125 fleas. Previous experiments have not demonstrated any differences in adult survival or fecundity based on such variance in numbers of fleas in a chamber. Three chambers were prepared for each experimental and control group. A fresh blood meal containing the appropriate inhibitor in 3 ml total volume was placed on each chamber daily through the 7 day extent of an assay.

On days 3, 5, and 7 of the assay, surviving adult fleas were transferred to clean chambers. The contents of the original chambers were dissolved in about 40 ml of PBS (phosphate-buffered saline) in a 50 ml Falcon tube. The contents of a given tube were then filtered through a pre-weighed #1 Whatman filter disk inserted into a vacuum filter. The 50 ml tube and the filter funnel were rinsed with distilled water which was then passed through the filter. Once the chamber contents had been filtered, dead adult fleas were removed from the filter paper and placed in a labelled tube so that they could be counted and sexed. The filter paper was then placed into a preweighed 12×75 polypropylene tube and dried in the SpeedVac for 2.5 hr with the heater on. After drying the filter paper was weighed. The weight of the filter paper and tube was subtracted to obtain the dry weight of the eggs and this value was converted to an estimated number of eggs using the formula $y=41384.361x+162.37$, where x=dry weight of eggs.

On day 7, adult fleas that had survived the study were frozen, counted and sexed. The numbers were added to the number of male and female fleas that had died during the assay to verify the number of male and female fleas in each chamber at the start of the study.

Female, male and total adult flea survival were calculated for all experimental and control groups on days 3, 5, and 7 of each assay. Additionally, the number of eggs per surviving female was calculated on days 3, 5 and 7. Female fleas found dead on a given collection date were included in the total number of egg-laying females for the days between that date and the previous collection date, providing a conservative estimate of fecundity. Fecundity values were averaged for the three collection dates to obtain an average for each group over 7 days.

Results of these studies are presented below in Table 1 and FIG. 6 through FIG. 9. All survival and fecundity values are presented below as a percent of control value.

TABLE 1

Effect of Protease Inhibitors on Flea Viability and Fecundity

| Compound | Conc. | Fecundity[1] Days 1–7 | Adult Survival[1] Female | Male | Total |
|---|---|---|---|---|---|
| AEBSF | 6.0 mM | 17.2% | 4.1% | 0.0 | 3.4% |
|  | 5.0 mM | 1.4% | 6.8% | 0.0% | 5.6% |
|  | 0.5 mM | 95.0% | 103.9% | 104.2% | 103.6% |
|  | 0.3 mM | 82.4% | 116.2% | 103.0% | 111.9% |
| Aprotinin | 20 ug/ml | 84.2% | 100.0% | 101.7% | 99.9% |
|  | 2 ug/ml | 83.2% | 103.2% | 104.9% | 103.3% |
| Leupeptin | 50 ug/ml | 77.6% | 101.5% | 111.7% | 104.6% |
|  | 5 ug/ml | 85.0% | 71.0% | 61.4% | 68.4% |
| Soybean Trypsin Inhibitor | 100 ug/ml | 79.1% | 76.5% | 76.0% | 76.3% |
|  | 10 ug/ml | 96.1% | 80.1% | 101.7% | 83.9% |
| Trypsin/ Chymotrypsin Inhibitor | 100 ug/ml | 81.1% | 88.0% | 95.4% | 89.9% |
|  | 10 ug/ml | 100.7% | 115.1% | 143.5% | 120.7% |
| E-64 | 10 ug/ml | 177.4% | 110.2% | 139.0% | 114.2% |
|  | 1 ug/ml | 109.4% | 99.9% | 102.9% | 100.1% |
|  | 10 ug/ml | 84.1% | 90.2% | 91.1% | 90.6% |
|  | 1 ug/ml | 95.2% | 77.3% | 80.0% | 77.5% |
| Phosphoramidon | 100 ug/ml | 84.9% | 70.2% | 64.6% | 69.7% |
|  | 10 ug/ml | 89.0% | 98.8% | 95.2% | 97.8% |
| Pepstatin A | 10 ug/ml | 83.9% | 113.6% | 133.4% | 116.2% |
|  | 1 ug/ml | 67.7% | 77.6% | 96.6% | 80.5% |
| Bestatin | 13.0 mM | 23.3% | 121.0% | 103.4% | 117.0% |
|  | 1.3 mM | 60.4% | 119.5% | 116.3% | 116.8% |

[1]All experimental values are expressed as a percent of the corresponding control group.

The aminopeptidase inhibitor bestatin caused a significant ($p<0.05$) reduction in fecundity at 13 mM (77% reduction) and at 1.3 mM (40% reduction) indicating the presence of an aminopeptidase or other exopeptidase in flea midguts. Bestatin at the concentrations tested, however, had no significant effect on adult viability at either concentration. These results suggest that aminopeptidases may play a role in ovarian function, or a related process, such as vitellogenesis.

The aspartic acid protease inhibitor pepstatin A caused a significant reduction ($p<0.05$) in fecundity at 1 µg/ml (32% reduction), but not at 10 µg/ml. Pepstatin A had no significant effect on adult viability at either concentration.

The cysteine protease inhibitor E-64 showed no statistically significant reduction in fecundity in this assay. There was a small, but significant ($p<0.05$), reduction in total adult flea survival when E-64 was dissolved in grain alcohol and added to blood at 1 g/ml. However, this reduction was not evident in the group that was fed blood containing 10 µg/ml E-64 in grain alcohol.

The metalloprotease inhibitor phosphoramidon caused a reduction in adult viability of about 30%, which, however was not statistically significant. There was no significant reduction in fecundity.

Results using serine protease inhibitors were particularly interesting and suggest the significance of serine proteases in flea midguts. AEBSF administered at concentrations ranging from about 5 mM to about 6 mM reduced flea fecundity by more than 80%. In addition, adult survival was reduced to near zero ($p<0.05$).

Aprotinin, however, had no significant effect on either fecundity or viability, likely due to the ability of serum proteins, such as albumin, to interfere with aprotinin's inhibitory activity.

Leupeptin had no effect on fecundity at both concentrations, but reduced adult viability by 30% at 5 µg/ml. However, adult viability was not affected by 50 µg/ml leupeptin and none of the observed reductions were statistically significant.

Soybean trypsin inhibitor caused a small (20%) statistically insignificant reduction in fecundity at 100 µg/ml. The lower concentration had no effect. Soybean trypsin inhibitor, on the other hand, is very effective in in vitro studies as disclosed in several of the examples and was used to purify serine proteases as disclosed in Example 7. Soybean trypsin/ chymotrypsin inhibitor had no effect on adult viability or fecundity.

Example 7

This Example describes the production of a preferred soluble flea midgut preparation of the present invention and purification of flea serine proteases therefrom. Also included is amino acid sequence analysis of a flea serine protease of the present invention.

The soluble flea midgut preparation was prepared as follows. Flea midguts (3,735) from a mix of female and male fed fleas were homogenized in a homogenization buffer comprising 1.5 ml 50 mM Tris-HCl, 0.5 M NaCl, pH 8.5. The homogenate was centrifuged at 14,000×g for 10 min. The resultant pellet was processed again in another 1.5 ml of the homogenization. The two supernatant solutions were combined to form the soluble flea midgut preparation.

The preparation was added to 3 ml of p-aminobenzamidinesepharose 6 B (affinity matrix for trypsin-like proteases, available from Sigma) and incubated at 5° C. overnight on a rocker. The sepharose beads were drained and washed with 7.5 ml of the homogenization buffer. The adsorbed proteins were eluted with 5 ml 0.1 M p-aminobenzamidine in the same buffer. This eluate was concentrated and the buffer exchanged to 50 mM Tris-HCl pH 8.5, 0.1 mM $CaCl_2$ by ultrafiltration through a membrane with a 3 kD cutoff, the final volume being 140 µl (microliters).

Labeling of proteins was performed by adding 10 µl of (1,3-$^3$H)-diisopropylfluorophosphate (available from New England Nuclear, Beverly, Mass., at 6.0 Ci (Curies)/mmole, 1.0 mCi/ml) to 90 µl of the affinity purified proteins and incubating at 5° C. for 18 hours. The reaction was divided in half, each half then being separated by C4 reverse phase chromatography according to the following protocol:

Buffer A: 0.1% TFA in water

Buffer B: 0.085% TFA, 90% Acetonitrile 0.8 ml/min, 220 nm, 1 min fractions 5.6% B 15 min 5.6% to 100% B over 60 min Ten microliters of each fraction was added to scintillation fluid and counted. Most protein-associated counts were found in fractions 44–47. FIG. 5A shows electrophoresis of fractions 40 (lane 2), 44 (lane 3), 46 (lane 4) and 47 (lane 5) from one chromatography run through a 14% Tris-glycine polyacrylamide-SDS gel, followed by coomassie staining. This gel was then processed with Entensigy (NEN) and exposed to film for 18 hours, as shown in FIG. 5B. Each fraction contained several proteins as shown in FIG. 5A, but only 4 bands were labeled, the most prominent being 26 kd (seen in lanes 3, 4 and 5), and denoted herein as PfSP26. A faint band of 24 kd, denoted herein as PfSP24, was also noticed in lane 5. A band of 19 kD, denoted herein as PfSP19, was labeled in lane 4 that was associated with a very faintly staining protein band. Some labeled proteins were seen at the dye front of lanes 4 and 5, indicating a molecular weight less than 6 kd, denoted herein as PfSP6, and could be degradation products.

Fraction 44 (analogous to lane 3) from a second C4 chromatography separation experiment was electrophoresed, blotted onto PVDF, stained with Coomassie R-250 and destained via standard procedures. The 26 kd band, corresponding to PfSP26 (also referred to herein as PfSP44-E, indicating the fraction in which the protein eluted and the gel/filter band from which the protein was excised), was excised and subjected to N-terminal amino acid sequencing using techniques known to those skilled in the art. A partial N-terminal amino acid sequence of about 32 amino acids was deduced and is represented herein as SEQ ID NO:1:

I I G G E V A G E G S A P Y Q V S L R T K E G N H F S G G S I L,

It should be noted that since amino acid sequencing technology is not entirely error-free, SEQ ID No:1 represents, at best, an apparent partial N-terminal amino acid sequence of PfSP26. This caution is particularly relevant in light of the sequencing of this protein having been done at a low picomolar concentration.

A homology search of the non-redundant protein sequence database was performed through the National Center for Biotechnology Information using the BLAST network. This database includes +SwissProt+PIR+ SPUpdate+GenPept+GPUpdate.ole level. Results of the search indicate that the N-terminus of PfSP26 shares significant amino sequence homology with a number of serine proteases, including a variety of trypsins, chymotrypsins and plasmins. The 32-amino acid N-terminal amino acid sequence of PfSP26 shared the highest degree of homology with a hornet chymotrypsin II.

Example 8

This example describes the cloning of certain flea protease nucleic acid molecules of the present invention. This example also describes the production of certain recombinant molecules, recombinant cells and flea protease proteins of the present invention.

Several flea serine protease nucleic acid molecules, ranging in size from about 250 to about 500 nucleotides, and representing one or more partial flea serine protease genes, were PCR amplified from a fed flea midgut cDNA library that was prepared from RNA isolated from fed flea midguts using standard protocols as described in Sambrook et al., ibid. Several pairs of primers were used in PCR amplification reactions that represented degenerate oligonucleotides designed from published sequences of serine protease genes isolated from biting insects (e.g., mosquitos and black flies). Each primer pair was designed so that a properly amplified fragment of a flea serine protease gene would include a domain corresponding to the most conserved domain of trypsin protease genes (thought to be the active site) given that such a domain is contained in flea serine protease gene(s).

The amplified PCR fragments were of predicted size, ranging from about 250 nucleotides to about 500 nucleotides, depending on which primer pairs were used. PCR fragments that hybridized to a probe designed from the domain most conserved among all known trypsin genes were gel purified and cloned, for example, into the pCRII cloning vector (available from InVitrogen, Corp., San Diego, Calif.), following manufacturer's instructions. Nucleic acid sequences of the fragments are being determined using standard techniques.

The amplified PCR fragments are also being used as probes to identify full-length flea protease genes in unfed and fed flea midgut cDNA libraries and in flea salivary gland cDNA libraries, as well as in flea genomic DNA libraries, using standard procedures.

Recombinant molecules and recombinant cells including the amplified PCR fragments as well as full-length flea protease genes are being produced using standard procedures. Culturing of such recombinant cells leads to the production of flea protease proteins of the present invention.

Example 9

This Example describes the testing of a flea protease protein as a flea protease vaccine of the present invention, that is for the ability of such a protein, upon administration to an animal, to elicit the production of antibodies that reduce flea protease activity and, as such, reduce flea viability and/or fecundity. This Example also demonstrates the use of such a flea protease protein as a vaccine on a dog subsequently infested with fleas.

A flea protease protein produced as described in Example 7 is administered to rabbits according to a standard immunization protocol known to those skilled in the art, including appropriate booster shots. Such a protein is also administered to guinea pigs and to dogs following a similar protocol.

Sera is collected from the treated rabbits and is verified to contain anti-flea protease antibodies. Such sera is then fed to fleas in a feeding system as reported by Wade et al. ibid. Fleas feeding on such a sera show reduced viability compared to fleas feeding on sera collected from rabbits not administered the flea protease protein. Sera from treated guinea pigs and dogs are verified in a similar manner.

Dogs treated with a flea protease protein are then infested with fleas as are dogs not treated with a flea protease protein. Dogs treated with a flea protease protein show a significant reduction in flea burden compared to untreated dogs.

Example 10

This Example describes the determination of the partial N-terminal amino acid sequence of additional flea serine protease proteins of the present invention.

An additional eight flea serine proteases were purified and consensus partial N-terminal amino acid sequences were determined as described in Example 7. The results are as follows, the proteins being named by the fraction in which they were eluted and the SDS-PAGE gel band from which they were excised. Each of the proteases bore at least some sequence homology to known proteases, the highest percent identity estimated to be no more than about 30–40%.

Flea protease PfSP45-C had a partial N-terminal amino acid sequence of X V G G H D T S I D X H P H Q V T, also represented herein as SEQ ID NO:2. PfSP45-C was most similar in amino acid sequence to a fruit fly trypsin epsilon.

Flea protease PfSP46-C had a partial N-terminal amino acid sequence of I V G G A D A A P G N A P F Q V S L R D K G, also represented herein as SEQ ID NO:3. PfSP46-C was most similar in amino acid sequence to a collagenolytic 36 kD protease from a Kamchatda crab.

Flea protease PfSP46-A had a partial N-terminal amino acid sequence of I V G G Q D A D I A K Y G Y Q A S L Q V F N E H F X G A X I L N N Y, also represented herein as SEQ ID NO:4. PfSP46-A was most similar in amino acid sequence to a hornet chymotrypsin II.

Flea protease PfSP46-B had a partial N-terminal amino acid sequence of I V G G T D V N I E N F G W Q V S L F D R N G H F, also represented herein as SEQ ID NO:5. PfSP46-B was most similar in amino acid sequence to a fruit fly trypsin beta.

Flea protease PfSP48-A had a partial N-terminal amino acid sequence of I V G G H D T S I D K H P F Q V S L I D K N, also represented herein as SEQ ID NO:6. PfSP48-A was most similar in amino acid sequence to a fruit fly trypsin epsilon.

Flea protease PfSP48-B had a partial N-terminal amino acid sequence of V V G G L E A A E G S A P Y Q V X L Q W G N F, also represented herein as SEQ ID NO:7. PfSP48-B was most similar in amino acid sequence to a human Factor 12.

Flea protease PfSP48-D had a partial N-terminal amino acid sequence of I V G G E D A E L G E X P T Q, also represented herein as SEQ ID NO:8. PfSP48-D was most similar in amino acid sequence to a bovine Factor 9.

Flea protease PfSP40-B had a partial N-terminal amino acid sequence of D E D G K D D S A P G E I, also represented herein as SEQ ID NO:9. PfSP40-B was most similar in amino acid sequence to a fruit fly furin-like protease I.

Example 11

This Example describes the isolation of nucleic acid molecules encoding flea serine protease proteins of the present invention.

Several midgut proteinase cDNA genes have been isolated in a manner similar to that described in Example 8, using two degenerate primers, the design of which was based on a highly conserved serine proteinase amino acid sequence (C Q/N G D S G G P L, denoted SEQ ID NO:10) located about 195 amino acid residues (based on an average protease size of about 240 residues) from the mature amino terminus in a number of known serine proteases. Complementing primers for use in the PCR amplification reaction were primers corresponding to the vectors in which nucleic acid molecules of the present invention had been ligated. The actual primers used in PCR amplification of serine protease nucleic acid molecules from whole fed flea cDNA expression libraries (produced as described in Example 8) included the following serine protease specific primers: cat-try #1 having nucleic acid sequence 5' TAA WGG WCC WCC YGA ATC TCC CTG GCA 3' (Y indicating C or T; W indicating A or T), represented herein as SEQ ID NO:11; and cat-try #2 having nucleic acid sequence 5' TAA WGG WCC AGA RTC TCC TTG ACA 3' (R indicating A or G), represented herein as SEQ ID NO:12. Vector specific primers included: M13 Reverse having nucleic acid sequence 5' GGAAACAGCTATGACCATG 3', represented herein as SEQ ID NO:13; and T3 Primer having nucleic acid sequence 5' ATTAACCCTCACTAAAG 3', represented herein as SEQ ID NO:14. The resultant PCR products, obtained using standard PCR conditions (e.g., Sambrook et al., ibid.), were about 600 to about 700 nucleotides in length.

The PCR products were hybridized under standard hybridization conditions (e.g., Sambrook et al., ibid.) with (i.e., to) an internal synthetic oligonucleotide probe named H57, the sequence of which corresponds to a region including a conserved histidine residue in known serine proteases. The nucleic acid sequence of H57 is 5' TGG GTW GTW ACW GCW GCW CAT TG 3', represented herein as SEQ ID NO:15. PCR products which hybridized strongly to the probe were gel purified and cloned into the TA Vector™ (available from InVitrogen, Corp.). Approximately 80 recombinant TA vector clones were isolated.

To prevent repetitive sequencing of the same serine proteinase clones, a number of the clones were characterized to identify those having unique restriction endonuclease patterns using the enzymes HaeII and HaeIII. About 11 plasmids apparently containing unique flea serine proteinase nucleic acid molecules of about 600 to about 700 nucleotides in length were isolated using this procedure. These nucleic acid molecules were subjected to nucleic acid sequencing using the Sanger dideoxy chain termination method, as described in Sambrook et al., ibid.

The complete nucleic acid sequence of one of the flea serine protease nucleic molecules, namely nfSP4$_{672}$ is represented herein as SEQ ID NO:16. Translation of SEQ ID NO:16 yields a protein of about 223 amino acids, denoted PfSP4$_{223}$, having amino acid sequence SEQ ID NO:17. Although the entire amino acid sequence of PfSP4$_{223}$ is not highly conserved to that of known serine proteases, there are several conserved regions of note (as numbered for SEQ ID NO:17), including: (a) the sequence IVGG spanning from about amino acid 5 through about amino acid 9; (b) the active-site histidine at about amino acid 46 and surrounding sequences spanning from about amino acid 41 through about amino acid 47; (c) the conserved aspartic acid residue at about amino acid 90; (d) the GWG sequence spanning from about amino acid 124 through about amino acid 126; the conserved cysteines at about amino acid 152 and about amino acid 165; and the conserved sequence around the active site serine, spanning from about amino acid 174 through about amino acid 182.

Nucleic acid and amino acid sequences of all 11 flea serine protease nucleic acid molecules were determined for the regions corresponding to the region in known serine proteases to span from the conserved GWG sequence to the conserved CXGDSGGP sequence (denoted SEQ ID NO:10). Flea nucleic acid molecule nfSP1$_{156}$ has the nucleic acid sequence represented herein as SEQ ID NO:18, which encodes a protein PfSP1$_{52}$ having an amino acid sequence represented herein as SEQ ID NO:19. Flea nucleic acid molecule nfSP2$_{168}$ has the nucleic acid sequence represented herein as SEQ ID NO:20, which encodes a protein PfSP2$_{56}$ having an amino acid sequence represented herein as SEQ ID NO:21. Flea nucleic acid molecule nfSP3$_{177}$ has the nucleic acid sequence represented herein as SEQ ID NO:22, which encodes a protein PfSP3$_{59}$ having an amino acid sequence represented herein as SEQ ID NO:23. Flea nucleic acid molecule nfSP4$_{156}$ has the nucleic acid sequence represented herein as SEQ ID NO:24, which encodes a protein PfSP4$_{52}$ having an amino acid sequence represented herein as SEQ ID NO:25. Flea nucleic acid molecule nfSP5$_{159}$ has the nucleic acid sequence represented herein as SEQ ID NO:26, which encodes PfSP5$_{53}$ having an amino acid sequence represented herein as SEQ ID NO:27. Flea nucleic acid molecule nfSP6$_{168}$ has the nucleic acid sequence represented herein as SEQ ID NO:28, which encodes a protein PfSP6$_{56}$ having an amino acid sequence represented herein as SEQ ID NO:29. Flea nucleic acid molecule nfSP7$_{159}$ has the nucleic acid sequence represented herein as SEQ ID NO:30, which encodes a protein PfSP7$_{53}$ having an amino acid sequence represented herein as SEQ ID NO:31. Flea nucleic acid molecule nfSP8$_{186}$ has the nucleic acid sequence represented herein as SEQ ID NO:32, which encodes a protein PfSP8$_{62}$ having an amino acid sequence represented herein as SEQ ID NO:33. Flea nucleic acid molecule nfSP9$_{168}$ has the nucleic acid sequence represented herein as SEQ ID NO:34, which encodes a protein PfSP9$_{56}$ having an amino acid sequence represented herein as SEQ ID NO:35. Flea nucleic acid molecule nfSP10$_{120}$ has the nucleic acid sequence represented herein as SEQ ID NO:36, which encodes a protein PfSP10$_{40}$ having an amino acid sequence represented herein as SEQ ID NO:37. Flea nucleic acid molecule nfSP11$_{162}$ has the nucleic acid sequence represented herein as SEQ ID NO:38, which encodes a protein PfSP11$_{54}$ having an amino acid sequence represented herein as SEQ ID NO:39.

Comparison of the nucleic acid sequences of the flea serine proteases with that of a mosquito (*A. aegypti*) trypsin indicates that SEQ ID NO:18 is about 33% identical, SEQ ID NO:20 is about 33% identical, SEQ ID NO:22 is about 24% identical, SEQ ID NO:24 is about 25% identical, SEQ ID NO:26 is about 32% identical, SEQ ID NO:28 is about 38% identical, SEQ ID NO:30 is about 33% identical, SEQ ID NO:32 is about 33% identical, SEQ ID NO:34 is about 40% identical, SEQ ID NO:36 is about 33% identical, and SEQ ID NO:38 is about 29% identical, to the corresponding region of the mosquito trypsin. Comparison of the nucleic acid sequences of the flea serine proteases with that of a black fly (*S. vittatum*) trypsin indicates that SEQ ID NO:18 is about 34% identical, SEQ ID NO:20 is about 34% identical, SEQ ID NO:22 is about 25% identical, SEQ ID NO:24 is about 28% identical, SEQ ID NO:26 is about 36% identical, SEQ ID NO:28 is about 45% identical, SEQ ID NO:30 is about 29% identical, SEQ ID NO:32 is about 36% identical, SEQ ID NO:34 is about 42% identical, SEQ ID NO:36 is about 34% identical, and SEQ ID NO:38 is about 30% identical, to the corresponding region of the black fly trypsin. It is to be noted that the mosquito and black fly trypsins are about 50% identical in the same regions.

Comparison of the amino acid sequences of the flea serine proteases with that of a mosquito (*A. aegypti*) trypsin indicates that SEQ ID NO:19 is about 11% identical, SEQ ID NO:21 is about 30% identical, SEQ ID NO:23 is about 19% identical, SEQ ID NO:25 is about 19% identical, SEQ ID NO:27 is about 28% identical, SEQ ID NO:29 is about 21% identical, SEQ ID NO:31 is about 14% identical, SEQ ID NO:33 is about 22% identical, SEQ ID NO:35 is about 30% identical, SEQ ID NO:37 is about 22% identical, and SEQ ID NO:39 is about 29% identical, to the corresponding region of the mosquito trypsin. Comparison of the amino acid sequences of the flea serine proteases with that of a black fly (*S. vittatum*) trypsin indicates that SEQ ID NO:19 is about 14% identical, SEQ ID NO:21 is about 28% identical, SEQ ID NO:23 is about 16% identical, SEQ ID NO:25 is about 17% identical, SEQ ID NO:27 is about 35% identical, SEQ ID NO:29 is about 33% identical, SEQ ID NO:31 is about 11% identical, SEQ ID NO:33 is about 22% identical, SEQ ID NO:35 is about 33% identical, SEQ ID NO:37 is about 21% identical, and SEQ ID NO:39 is about 25% identical, to the corresponding region of the black fly trypsin. It is to be noted that the mosquito and black fly trypsins are about 50% identical in the same regions.

Partial N-terminal amino acid sequences were deduced for each of the cloned flea serine protease nucleic acid molecules, four of which were identical to the following amino acid sequences derived from N-terminal sequencing of serine proteases as described in Example 10: SEQ ID NO:1, SEQ ID NO:4, SEQ ID NO:6 and SEQ ID NO:7. The remaining nucleic acid molecules had the following deduced N-terminal amino acid sequences: SEQ ID NO:40, namely I V G G E N A K E K S D V P Y Q V S L R N A E N K H F C G G A I I D D Y W V L T, which was most similar in amino acid sequence to mite fecal allergen Der pIII; SEQ ID NO:41, namely I V G G L E A K N G S A P F M V S L Q A E D Y F H, which was most similar in amino acid sequence to a chymotrypsin-like protein; SEQ ID NO:42, namely I I G G E V A G E G S A P Y Q V S L R T K E G N H F, which was most similar in amino acid sequence to a chymotrypsin-like protein; SEQ ID NO:43, namely I V G G T A V D I R G F P G R Y Q F K P K P S F L W W F Y, which did not substantially match any protein in the data base; SEQ ID NO:44, namely I V N G L E A G V G Q F P I Q V F L D L T N I R D E K S R C G G A L F, which was most similar in amino acid sequence to a trypsin precursor; SEQ ID NO:45, namely I V G G L E A K N G I T P F I G F F A S G R L F, which was most similar in amino acid sequence to a chymotrypsin-like protease; SEQ ID NO:46, namely I V G G N D V S X K I F W Q V S I Q S N X Q H F C G, which was most similar in amino acid sequence to a trypsin; and SEQ ID NO:47, namely I I G G E D A P E G S A P Y Q V S L R N Q N L E H F C G G S I, which was most similar in amino acid sequence to a chymotrypsin-like protein.

Additional amino terminal and carboxyl terminal sequences of flea serine protease nucleic acid molecules comprising sequences listed above as well as additional nucleic acid molecules identified using the techniques described herein are presented in Table 2.

TABLE 2

Additional Flea Serine Protease Sequences

A. The apparent N-terminal nucleic acid and deduced amino acid sequence of nfSP1 (SEQ ID NOS:52 and 53) is:

```
TCA GCA CTC GTT GCC TTG TCT GCA GCT ATT CCT CAC TCC AAC AGA GTC
 S   A   L   V   A   L   S   A   A   I   P   H   S   N   R   V

GTT GGA GGA CTG GAA GCT GCA GAG GGT TCT GCA CCT TAT CAA GTA TCC
 V   G   G   L   E   A   A   E   G   S   A   P   Y   Q   V   S
```

TABLE 2-continued

Additional Flea Serine Protease Sequences

```
TTG CAA GTT GGC AAC TTC CAC TTC TGT GGT GGT TCA ATT CTG AAC GAA
 L   Q   V   G   N   F   H   F   C   G   G   S   I   L   N   E

TAT TGG GTT TTG ACT GCT GCT CAC TGT TTG GGT TAT GAC TTC GAC GTG
 Y   W   V   L   T   A   A   H   C   L   G   Y   D   F   D   V

GTA GTT GGA ACA AAC AAA CTT GAT CAA CCA GGT GAA AGA TAC CTC GTA
 V   V   G   T   N   K   L   D   Q   P   G   E   R   Y   L   V

GAA CAA ACT TTT GTT CAC
 E   Q   T   F   V   H
```

B. The apparent N-terminal nucleic acid and deduced amino acid sequence of nfSP2 (SEQ ID NOS:54 and 55) is

```
TTA GAT GGG CGC ATT GTT GGA GGA CAA GAT GCT GAT ATT GCC AAA TAT
 L   D   G   R   I   V   G   G   Q   D   A   D   I   A   K   Y

GGC TAT CAA GCT TCA CTC CAA GTA TTT AAC GAA CAT TTC TGT GGA GCT
 G   Y   Q   A   S   L   Q   V   F   N   E   H   F   C   G   A

TCA ATA TTG AAT AAT TAT TGG ATT GTC ACA GCA GCT CAT TGC ATA TAT
 S   I   L   N   N   Y   W   I   V   T   A   A   H   C   I   Y

GAT GAA TTC ACG TAT TCA GTT CGA GTC GGC ACC AGT TTC CAA GGA AGA
 D   E   F   T   Y   S   V   R   V   G   T   S   F   Q   G   R

CGT GGT TCC GTT CAT CCT GTG GCA CAA ATT ATC AAG CAT CCT GCA TAC
 R   G   S   V   H   P   V   A   Q   I   I   K   H   P   A   Y
```

C. The apparent N-terminal nucleic acid and deduced amino acid sequence of nfSP4 (SEQ ID NOS:56 and 57) is:

```
AGG GAA CAA AAG CTG GAG CTC CAC CGC GGT GCG CCG GCT CTA GAA CTA
 R   E   Q   K   L   E   L   H   R   G   A   P   A   L   E   L

GTG GAT CCC CCG GGT CTG CAG GAA TTG GCA CGA GGA TGT TCT TGG CTG
 V   D   P   P   G   L   Q   E   L   A   R   G   C   S   W   L

TGT TTA GTA GCT ATT CTT TGT GCA GTG GCT GCT GGG CCT ACT AAT CGC
 C   L   V   A   I   L   C   A   V   A   A   G   P   T   N   R

ATT GTT GGA GGA TTG GAG GCG AAA AAT GGA ATC ACC CCA TTC ATC GGT
 I   V   G   G   L   E   A   K   N   G   I   T   P   F   I   G

TTC TTT GCA AGC GGA AGA CTA TTT CA
 F   F   A   S   G   R   L   F
```

D. The apparent N-terminal nucleic acid and deduced amino acid sequence of nfSP5 (SEQ ID NOS: 58 and 59) is:

```
ACG AGG TTT CGC TTA GCA ATT GTA TGT GCT CTC GCT GTC TGC ACA TTC
 T   R   F   R   L   A   I   V   C   A   L   A   V   C   T   F

GGT GCC AGT GTT CCA GAA CCA TGG AAA AGA TTA GAT GGT AGA ATC GTA
 G   A   S   V   P   E   P   W   K   R   L   D   G   R   I   V

GGA GGA CAC GAT ACC AGC ATC GAT AAA CAC CCT CAT CAA GTA TCT TTA
 G   G   H   D   T   S   I   D   K   H   P   H   Q   V   S   L

TTG TAC TCC AGC CAC AAT TGT GGT GGT TCC TTG ATT GCC AAA AAC TGG
 L   Y   S   S   H   N   C   G   G   S   L   I   A   K   N   W

GTT TTG ACT GCA GCT CAT TGC ATT GGA GTT AAC AAA TAC AAT GTC CGT
 V   L   T   A   A   H   C   I   G   V   N   K   Y   N   V   R
```

E. The apparent N-terminal nucleic acid and deduced amino acid sequence of nfSP6 (SEQ ID NOS:60 and 61) is:

```
CCC TCA CTA AAG GGA ACA AAA GCT GGA GCT CCA CCG CGG TGC GCC GCT
 P   S   L   K   G   T   K   A   G   A   P   P   R   C   A   A

CTA GAA CTA GTG GAT CCC CCG GGC TGC AGG AAT TCG GCA CGA GCG TTT
 L   E   L   V   D   P   P   G   C   R   N   S   A   R   A   F

GGT TGG ATT GAG CGC GTC TCA TCT TAC AAG ATA AAG GAT AGA TTA GAT
 G   W   I   E   R   V   S   S   Y   K   I   K   D   R   L   D
```

TABLE 2-continued

Additional Flea Serine Protease Sequences

```
GGG CGC ATT GTT GGA GGA CAA GAT GCT GAT ATT GCC AAA TAT GGC TAT
 G   R   I   V   G   G   Q   D   A   D   I   A   K   Y   G   Y

CAA GCT TCA CTC CAA GTA CTT AAC GAA CAT TTC TGT GGA GCT
 Q   A   S   L   Q   V   L   N   E   H   F   C   G   A
```

F. The apparent N-terminal nucleic acid and deduced amino acid sequence of nfSP7 (SEQ ID NOS:62 and 63) is:

```
GCG GTG ATT GTG TCA TTT GTT CTG GCT TGT GCA TTT TCT GTA CAG GCT
 A   V   I   V   S   F   V   L   A   C   A   F   S   V   Q   A

CTT CCA TCA AGC AGA ATT GTC AAT GGA CTT GAA GCA GGA GTT GGA CAA
 L   P   S   S   R   I   V   N   G   L   E   A   G   V   G   Q

TTT CCA ATT CAG GTT TTC TTA GAC TTG ACA AAT ATC AGA GAC GAA AAA
 F   P   I   Q   V   F   L   D   L   T   N   I   R   D   E   K

TCC AGA TGT GGT GGT GCT TTG TTA TCA GAT TCA TGG GTT TTG ACT GCT
 S   R   C   G   G   A   L   L   S   D   S   W   V   L   T   A

GCT CAT TGT TTT GAT GAT TTG AAG TCT ATG GTA GTG TCC GTT GGT GCT
 A   H   C   F   D   D   L   K   S   M   V   V   S   V   G   A

CAT GAT GTC AGC AAA TCT GAA GAA CCT CAC AGG CAA ACC AGG AAA CCT
 H   D   V   S   K   S   E   E   P   H   R   Q   T   R   K   P

GAA
 E
```

G. The apparent N-terminal nucleic acid and deduced amino acid sequence of nfSP12 (SEQ ID NOS:64 and 65) is:

```
GTA CTG ATC GTT TTA GCA GTC ATT GAA TTC GCA TCA GCG TCT TCA ATC
 V   L   I   V   L   A   V   I   E   F   A   S   A   S   S   I

GGC TGG AGA ATC GTG GGT GGT GAA AAT GCT AAA GAA AAA TCG GTG CCC
 G   W   R   I   V   G   G   E   N   A   K   E   K   S   V   P

TAT CAA GTT TCM CTT CGA AAT GCT GAA AAC AAA CAT TTY TGT GGR GGR
 Y   Q   V   S   L   R   N   A   E   N   K   H   F   C   G   G
```

H. The apparent N-terminal nucleic acid and deduced amino acid sequence of nfSP13 (SEQ ID NOS:66 and 67) is:

```
TTC GGC TTC AAG CTA AGT CAT TTG GTA AGT AAG TAC TGT GCT TGT GCA
 F   G   F   K   L   S   H   L   V   S   K   Y   C   A   C   A

TTA GCA TCG GCA CTG AAG TAC TCC ATC GAT CAT GGT CCT CGT ATC ATC
 L   A   S   A   L   K   Y   S   I   D   H   G   P   R   I   I

GGA GGT GAA GTT GCA GGT GAA GGA TCA GCA CCT TAC CAG GTG TCC TTA
 G   G   E   V   A   G   E   G   S   A   P   Y   Q   V   S   L

AGA ACC AAG GAA GGA AAT CAT TTT TGC GGT GGA TCA ATA CTA AAT AAG
 R   T   K   E   G   N   H   F   C   G   G   S   I   L   N   K

CGA TGG GTT GTA ACT GCA GCA CAT TGT CTT GAA CCG GAA ATA TTA GAT
 R   W   V   V   T   A   A   H   C   L   E   P   E   I   L   D

TCG GTA TAC GTC GGA TCC AAT CAC TTA GAC CGA AAA GGC AGA TAT TAC
 S   V   Y   V   G   S   N   H   L   D   R   K   G   R   Y   Y

GAC GTA GAA CGG TAT ATA ATT CAT GAA AAA TAT ATA GGA GAA CTA AAT
 D   V   E   R   Y   I   I   H   E   K   Y   I   G   E   L   N

AAT TTT TAT GCT GAC ATC GGT CTA ATA AAA CTT GAT GGA AGA CTT AGA
 N   F   Y   A   D   I   G   L   I   K   L   D   G   R   L   R

ATT CAA
 I   Q
```

TABLE 2-continued

Additional Flea Serine Protease Sequences

I. The apparent N-terminal nucleic acid and deduced amino acid sequence of nfSP14 (SEQ ID NOS:68 and 69)is:

```
CGG GCT GCA GGA ATT CGG CAC GAG AAG AAA CTG CCA ATA TTA ATC GCC
 R   A   A   G   I   R   H   E   K   K   L   P   I   L   I   A

TTG ATC GGA TGC GTT CTT TCT GAA GAA ATA GAG GAT CGC ATT GTC GGC
 L   I   G   C   V   L   S   E   E   I   E   D   R   I   V   G

GGA ACG GCA GTT GAT ATA AGA GGT TTT CCC TGG CAG GTA TCA ATT CAA
 G   T   A   V   D   I   R   G   F   P   W   Q   V   S   I   Q

ACC GAA AAC CGT CAT TTT TGT GGT GGT TCT ATT ATC GAT AAA AGC TGG
 T   E   N   R   H   F   C   G   G   S   I   I   D   K   S   W

ATA TTA ACT GCC GCA CAT TGT GTA CMC GAT ATG AAG ATG TCG AAC TGG
 I   L   T   A   A   H   C   V   X   D   M   K   M   S   N   W
```

J. The apparent N-terminal nucleic acid and deduced amino acid sequence of nfSP15 (SEQ ID NOS:70 and 71) is:

```
CAC GAG ATT TTA TTA AGC GCA TTA TTT GCA AGT GTA ATT TGC TCC TTT
 H   E   I   L   L   S   A   L   F   A   S   V   I   C   S   F

AAC GCG GAA GTA CAA AAT CGA ATC GTT GGT GGC AAT GAT GTA AGT ATT
 N   A   E   V   Q   N   R   I   V   G   G   N   D   V   S   I

TCA AAA ATT GGG TGG CAA GTA TCT ATT CAA AGT AAT AAA CAA CAT TTC
 S   K   I   G   W   Q   V   S   I   Q   S   N   K   Q   H   F

TGT GGT GGT TCA ATC ATT GCT AAA GAT GGG TCC
 C   G   G   S   I   I   A   K   D   G   S
```

K. The apparent N-terminal nucleic acid and deduced amino acid sequence of nfSP16 (SEQ ID NOS:72 and 73)is:

```
ATC ATG GCA AAT TTT AGG CTA TTC ACC TTA CTA GCC TTG GTT TCA GTA
 I   M   A   N   F   R   L   F   T   L   L   A   L   V   S   V

GCA ACT TCC AAA TAT ATT GAT CCA AGA ATA ATT GGA GGC GAA GAT GCT
 A   T   S   K   Y   I   D   P   R   I   I   G   G   E   D   A

CCT GAA GGC TCG GCT CCG TAC CAA GTT TCA TTG AGA AAT CAG AAT CTG
 P   E   G   S   A   P   Y   Q   V   S   L   R   N   Q   N   L

GAG CAT TTC TGT GGT GGT TCC ATT
 E   H   F   C   G   G   S   I
```

L. The apparent N-terminal nucleic acid and deduced amino acid sequence of nfSP17 (SEQ ID NOS:74 and 75) is:

```
GCA CGA GAT CGC ATT GTT GGA GGA TTG GAG GCG AAA AAT GGA TCA GCC
 A   R   D   R   I   V   G   G   L   E   A   K   N   G   S   A

CCA TTC ATG GTT TCT TTG CAA GCG GAA GAC TAT TTT CAT TTT TGT GGA
 P   F   M   V   S   L   Q   A   E   D   Y   F   H   F   C   G

TCC TCT ATT CTG AAT GAG AGA TGG GTT CTT ACT GCT GCT CAC TGT ATC
 S   S   I   L   N   E   R   W   V   L   T   A   A   H   C   I

CAA CCA AAT GTA CAC AAG TAC GTT TAC GTC GGT TCG AAC AAC GTA GAA
 Q   P   N   V   H   K   Y   V   Y   V   G   S   N   N   V   E
```

M. The apparent C-terminal nucleic acid and deduced amino acid sequence of nfSP12 (SEQ ID NOS:76 and 77) is:

```
CCA ATC CAC GAT AGC CAA TAT GCA CTT TTG CAG ATA TGG GTC AAG GGT
 P   I   H   D   S   Q   Y   A   L   L   Q   I   W   V   K   G

GCA TGT AAG GGT GAT TCC GGT GGC CCC TTA GTC ATC AAT GGA CAA CTT
 A   C   K   G   D   S   G   G   P   L   V   I   N   G   Q   L

CAT GGA ATT GTT TCC TGG GGC ATT CCT TGC GCT GTC GCA AGC CTG ATG
 H   G   I   V   S   W   G   I   P   C   A   V   A   S   L   M

TAT TCA CAA GAG TTT CTC ATT ATG TCG ATT GGA TTA AAT CCA AAA TTG
 Y   S   Q   E   F   L   I   M   S   I   G   L   N   P   K   L
```

TABLE 2-continued

Additional Flea Serine Protease Sequences

```
AAT AAA ATT GTT TAG
 N   K   I   V   *
```

N. The apparent C-terminal nucleic acid and deduced amino acid
sequence of nfsP13 (SEQ ID NOS:78 and 79) is (the initial GGPL
is next to the conserved active-site serine):

```
GGA GGT CCT TTG GCA ATC AAT GGT GAA CTT GTT GGT GTT ACT TCA TTC
 G   G   P   L   A   I   N   G   E   L   V   G   V   T   S   F

ATT ATG GGG ACA TGT GGA GGA GGA CAT CCT GAT GTC TTC GGT CGA GTC
 I   M   G   T   C   G   G   G   H   P   D   V   F   G   R   V

CTT GAC TTC AAA CCA TGG ATT GAT TCT CAT ATG GCA AAT GAC GGC GCT
 L   D   F   K   P   W   I   D   S   H   M   A   N   D   G   A

AAT TCT TTT ATT TAA
 N   S   F   I   *
```

Example 12

This Example describes the purification of a flea aminopeptidase of the present invention.

The starting material for the isolation of a flea aminopeptidase was a flea midgut lysate preparation that had been depleted of serine proteases by passage over a benzamidine-Sepharose affinity column. To assay for aminopeptidase activity, the synthetic substrate L-Leucine-AMC (Leu-AMC), which releases a fluorescent AMC leaving group upon proteolytic cleavage, was incubated with the serine protease-depleted flea midgut preparation. Aminopeptidase activity was easily detectable with as little as 1.2 µg of lysate, both confirming the presence of an aminopeptidase (as indicated in other Examples herein) and allowing for the detection of aminopeptidase activity in fractions collected throughout subsequent fractionation and purification procedures.

Serine protease-depleted flea midgut lysates (samples of about 1.2 µg and about 12 µg) were incubated with Leu-AMC in the presence of the following inhibitors: 1 mM pefabloc, 1 mg/ml trypsin/chymotrypsin inhibitor, 1 mg/ml trypsin inhibitor, 1 mM TPCK, 1 µg/ml pepstatin, 10 µg/ml E-64, 10 µg/ml of leupeptin, 10 mM EDTA, and 86 µg/ml of bestatin. Only bestatin inhibited the flea protease that cleaved Leu-AMC, whereas both EDTA and bestatin inhibited the control protease, a leucine aminopeptidase. These results indicated that the flea protease being characterized was an aminopeptidase, but apparently was not a metalloaminopeptidase like the "classic" leucine aminopeptidases.

A flea aminopeptidase was purified using the following protocol. Flea midgut lysates cleared of serine protease activity were fractionated by anion-exchange chromatography. Those fractions containing aminopeptidase activity were pooled and subjected to cation-exchange chromatography, and the resulting fractions were again assayed for activity with L-Leu-AMC in 96-well plates.

Fractions containing aminopeptidase activity were subjected to SDS-PAGE and silver-stained to identify the protein(s) exhibiting that activity. Aminopeptidase activity was found to be associated with proteins that migrated at a molecular weight of about 95 kD and about 56 kD when subjected to SDS-PAGE. The 95 kD and 56 kD proteins may each be aminopeptidases or they may be subunits of a larger enzyme. A number of known aminopeptidases are multi-subunit enzymes comprised of subunits ranging from about 45 kD to about 55 kD and from about 90 kD to about 95 kD.

Additional purification studies have indicated that the majority of aminopeptidase activity was found to be associated with the membrane pellet preparation and could be solubilized with detergent. Aminopeptidase activity in such preparations was also monitored during purification using L-Leu-AMC, and appeared to be associated with the 95 kD and 56 kD proteins when active fractions were analyzed by SDS-PAGE and silver staining. The 95 kD and 56 kD protein were co-purified to greater than 90% purity by cation exchange chromatography, affinity chromatography using w-aminohexyl agarose, and C-4 reverse phase chromatography. N-terminal amino acid sequence analysis indicated that both isolated aminopeptidases appeared to be blocked at the amino terminus.

Example 13

This Example describes the isolation of a flea aminopeptidase nucleic acid molecule of the present invention A nucleic acid molecule encoding a flea aminopeptidase was isolated in the following manner. A DNA fragment was PCR amplified from a whole fed flea cDNA expression library (prepared as described in Example 8 using degenerate primers, the design of which was based on conserved regions of bovine lens leucine aminopeptidase (LAP). The specific LAP-based primers used included: degenerate LAP sense primer A, corresponding to bovine lens LAP amino acid sequence from about amino acid 247 through 257 and having nucleic acid sequence 5' GTW GGW AAA GGW WTW ACW TTY GAT TCW GGW GG 3', represented herein as SEQ ID NO:48; and degenerate LAP antisense primer C, corresponding to bovine lens LAP amino acid sequence from about amino acid 335 through 329 and having nucleic acid sequence 5' CG WCC TTC WGC ATC WGT ATT 3' represented herein as SEQ ID NO:49. Also used were vector primers having SEQ ID NO:13 and SEQ ID NO:14, described in Example 11.

In a first experiment, the LAP primer C having SEQ ID NO:49 and the M13 reverse vector primer having SEQ ID NO:13 were used to PCR amplify DNA fragments from the expression library. The resultant PCR products were screened by hybridization under standard hybridization conditions with LAP primer A having SEQ ID NO:48. A PCR product that hybridized with SEQ ID NO:48 was subjected to nested (actually semi-nested) PCR amplification using LAP primer C and the T3 vector primer having SEQ ID NO:14. The resulting PCR product, which was about 900 nucleotides in length (denoted nfAP$_{900}$) and hybridized under standard (i.e., stringent) hybridization conditions with LAP primer A, was cloned into the TA™ vector and analyzed by DNA sequence analysis as described in Example 11.

The nucleic acid sequence of a portion of nfAP$_{900}$, namely of nfAP$_{453}$, is represented herein as SEQ ID NO:50. Translation of SEQ ID NO:50 yields a protein of about 151 amino acids, denoted herein as PfAP$_{151}$, the amino acid sequence of which is represented herein as SEQ ID NO:51. Analysis of SEQ ID NO:51 suggests that the sequence includes a leader segment of about 15 amino acids followed by a mature protein that has about 32% identity with the bovine lens LAP. The corresponding bovine and flea nucleotide sequences are about 29% identical.

Example 14

This Example describes the production of an anti-flea midgut protease antiserum and its use to inhibit flea protease activity thereby supporting the utility of protease-based vaccines as anti-flea agents.

Anti-flea protease antiserum was produced in the following manner. A rabbit was immunized 3 times with approximately 40–50 µg of a flea midgut protease preparation that had been affinity-purified using benzamidine sepharose as described in Example 7 and then combined with Freund's complete adjuvant for the first immunization and with incomplete adjuvant for the second and third immunizations according to standard procedures. After the second immunization, endpoint titers of around 1:3200 were obtained, while the third immunization boosted the anti-protease titers to about 1:6400. Western blot analysis of the immunoreactivity of the resultant anti-flea protease antiserum against the affinity-purified midgut protease preparation demonstrated the presence of at least 7–8 reactive protease bands. This was an important observation since there are numerous reports in the literature of difficulties associated with generating high-titered antisera against certain classes of proteases.

To assess the inhibitory activity of the rabbit anti-flea protease antiserum against flea midgut proteases, an in vitro assay which measures trypsin activity as a function of absorbance at OD$_{450}$ using a defined protein substrate (i.e., succinylated casein) was established using a commercially available kit (available from Pierce, Rockford, Ill.). In preliminary assays, the proteolytic activity of the affinity-purified flea midgut protease preparation was about 25–30% of the activity observed with the trypsin control. This lower activity is not unexpected since the flea proteases may require different reaction conditions than the trypsin control for optimal activity. Also, the primary amino acid sequences determined for the flea proteases as described in Examples 7, 10 and 11 are suggestive of highly specialized functions that may require specific substrates for determining optimal activity. Incubation of the affinity purified midgut protease preparation with the succinylated casein substrate in the presence of about 500 ng of the rabbit anti-flea protease antibody-containing serum collected after the second immunization reduced the proteolytic activity of the protease preparation by about 20%. This result, using a suboptimal assay, supports the feasibility of using immunological methods to inhibit flea midgut protease activity.

Using a similar immunization protocol, anti-flea protease antiserum has also been generated in cats that has exhibited immunoreactivity, as identified by Western blot analysis, against several proteases in the affinity-purified midgut protease preparation. The cat anti-flea protease antiserum also reduced proteolytic activity of an affinity purified midgut protease preparation by about 20%, using the same assay as described for analyzing the rabbit antiserum.

Example 15

This Example demonstrates that flea larvae have predominantly serine-type proteases.

Newly hatched flea larvae were raised in colony rearing dishes and fed on larval rearing media containing dried bovine blood using standard techniques. About 300 to 500 larvae were collected at different developmental stages, homogenized by sonication in flea gut dissection buffer (50 mM Tris, 100 mM CaCl$_2$, pH 8.0) and centrifuged to pellet cell debris. About 25 larval equivalents were incubated with about 2.5 µCi [1,3-$^3$H]-diisopropylfluorophosphate (DFP) overnight at 4° C. After incubation, about 10 larval equivalents were spotted onto filter paper, precipitated with 10% trichloroacetic acid, and counted in a liquid scintillation counter. Reducing SDS-PAGE was performed on samples comprising about 2.5 larval equivalents, and autoradiography was performed using standard techniques. In addition, adult flea midgut proteases were extracted and $^3$H-labeled in the same manner and examined by SDS-PAGE and autoradiography. Analysis of the gel indicated that, based on their ability to be labeled with DFP, larval proteases appear to be predominantly serine-type proteases, the production of which appears to be induced by blood feeding as occurs in adults. Blood-fed 3rd instars appeared to have the highest amount of proteolytic activity.

Example 16

The Example demonstrates that flea feces has proteolytic activity, that is predominantly due to serine proteases.

Flea feces were collected from fleas fed in flea cages placed on a live cat or in a flea feeding system as described in Example 6 in which the fleas were fed bovine blood. Fresh feces were collected every 9–17 hours, resuspended in water at 150 mg feces/ml, and centrifuged to pellet insoluble material. The soluble fractions were then assayed using two techniques. Western blot analysis was performed on samples subjected to reducing SDS-PAGE, each lane having about 40 µg of protein. Blotted proteins were incubated overnight at 4° C. with 1:500 rabbit anti-flea protease antiserum produced as described in Example 14. Goat anti-rabbit secondary antibody was used at 1:2000 to develop the Western blot. Analysis of the Western blot indicated the presence of serine-type proteases in flea feces. Appearance of such proteases migrating at about 25 to about 30 kD in such a system suggests the presence of full-length serine proteases.

Zymogram analysis was performed by loading approximately 50 µg protein into each lane of the electrophoresis gel in non-reducing sample buffer. After electrophoresis, the zymogram gel was soaked in 2.5% Triton-X-100 to renature the samples and developed at 37° C. in 50 mM Tris, pH 7.6, 200 mM NaCl, 5 mM CaCl$_2$, 0.02% Brij 35. Coomassie staining the gel revealed clear plaques where active proteases digested the gelatin in the gel matrix. Both of these techniques indicated the presence of serine-type proteases in flea feces.

Example 17

This Example demonstrates that fleas that have fed on antibody-containing blood have antibodies in their feces, suggesting an immunological method to eradicate flea larvae, which feed from flea feces.

The ability of antibodies in a blood meal to be taken up by fleas, pass through the midgut and be excreted in the feces was demonstrated in the following manner. A commercially available rabbit antibody against ovalbumin was added at near physiological concentration (i.e., at about 2 mg/ml) to the blood meal of adult fleas in a flea feeding system as described in Example 6. Feces were collected at 24 hr and 48 hr after feeding and rehydrated in phosphate saline buffer. The rehydrated fecal samples were subjected to Western blot analysis and shown to contain rabbit anti-ovalbumin antibodies that were apparently full-length, using a rabbit-specific secondary antibody screen against the Fc region of rabbit antibodies. Supernatants of flea midguts collected at the same time periods showed residual amounts of rabbit anti-ovalbumin antibodies.

In a second experiment, fleas were fed in a similar manner a blood meal containing cat-specific antiserum generated against keyhole limpet hemocyanin (KLH) and feces were collected at 24, 48 and 72 hours post-feeding. The sample collected at 24 hours was divided into halves, with one half rehydrated immediately in PBS while the second half was rehydrated 7 days later. Fecal samples collected at 48 and 72 hours were held for 6 and 5 days, respectively, after collection in desiccated form prior to rehydration. Aliquots of the bloodmeal containing the KLH antiserum fed to the fleas were also sampled at 1 and 2 days. All of the recovered antibodies were reactive against KLH by Western blot analysis, with a pattern or reactivity indistinguishable from the cat anti-KIH serum alone.

These studies demonstrate that antibodies are able to pass through the flea midgut in intact form and are able to maintain their antigen-binding characteristics, thereby supporting the feasibility of an immunological method to target larval development, since flea larvae in their normal habitat feed from flea feces.

What is claimed is:

1. An isolated protein selected from the group consisting of:

(a) a protein comprising an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77 and SEQ ID NO:79; and (b) a flea protein comprising a homologue of a protein of (a), wherein said homologue comprises at least a 6 contiguous amino acid portion of an amino acid sequence selected from the group consisting of SEQ ID NO:2, SEQ ID NO:3, SEQ ID NO:4, SEQ ID NO:5, SEQ ID NO:6, SEQ ID NO:8, SEQ ID NO:9, SEQ ID NO: 17, SEQ ID NO: 19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:44, SEQ ID NO:45, SEQ ID NO:46, SEQ ID NO:55, SEQ ID NO:57, SEQ ID NO:59, SEQ ID NO:61, SEQ ID NO:63, SEQ ID NO:69, SEQ ID NO:71, SEQ ID NO:75, SEQ ID NO:77 and SEQ ID NO:79.

2. The protein of claim 1, wherein said protein has serine protease activity.

3. The protein of claim 1, wherein said protein is encoded by a nucleic acid molecule that comprises a nucleic acid molecule selected from the group consisting of nfSP4$_{672}$ (characterized by a coding strand having the nucleic acid sequence of SEQ ID NO:16), nfSP1$_{156}$ (characterized by a coding strand having the nucleic acid sequence of SEQ ID NO:18), nfSP2$_{168}$ (characterized by a coding strand having the nucleic acid sequence of SEQ ID NO:20), nfSP3$_{177}$ (characterized by a coding strand having the nucleic acid sequence of SEQ ID NO:22), nfSP4$_{156}$ (characterized by a coding strand having the nucleic acid sequence of SEQ ID NO:24), nfSP5$_{159}$ (characterized by a coding strand having the nucleic acid sequence of SEQ ID NO:26), nfSP6$_{168}$ (characterized by a coding strand having the nucleic acid sequence of SEQ ID NO:28), nfSP7$_{159}$ (characterized by a coding strand having the nucleic acid sequence of SEQ ID NO:30), nfSP8$_{186}$ (characterized by a coding strand having the nucleic acid sequence of SEQ ID NO:32), nfSP9$_{168}$ (characterized by a coding strand having the nucleic acid sequence of SEQ ID NO:34), nfSP10$_{120}$ (characterized by a coding strand having the nucleic acid sequence of SEQ ID NO:36), and nfSP11$_{162}$ (characterized by a coding strand having the nucleic acid sequence of SEQ ID NO:38).

4. The protein of claim 1, wherein said protein comprises an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:40, SEQ ID NO:41, SEQ ID NO:42, SEQ ID NO;43, SEQ ID NO:44, SEQ ID NO:45, SEQ ID NO:46,and SEQ ID NO:47.

5. The protein of claim 1, wherein said protein comprises an amino acid sequence selected from the group consisting of SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77 and SEQ ID NO:79.

6. The protein of claim 1, wherein said protein is produced by a process comprising culturing an isolated recombinant cell transformed with a nucleic acid molecule encoding said protein to produce said protein.

7. An isolated protein encoded by a nucleic acid molecule selected from the group consisting of:

(a) a nucleic acid molecule comprising a nucleic acid sequence selected from the group consisting of SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76 and SEQ ID NO:78; and (b) a flea nucleic acid molecule comprising a homologue of any of said nucleic acid sequences of (a), wherein said homologue comprises a nucleic acid sequence comprising at least an 18 contiguous nucleotide portion of a nucleic acid sequence selected from the group consisting of SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:54, SEQ ID NO:56, SEQ ID NO:58, SEQ ID NO:60, SEQ ID NO:62, SEQ ID NO:68, SEQ ID NO:70, SEQ ID NO:74, SEQ ID NO:76 and SEQ ID NO:78.

8. The isolated protein of claim 7, wherein said protein is encoded by a nucleic acid molecule comprising a nucleic acid sequence selected from the group consisting of SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO: 70, SEQ ID NO:72, SEQ ID NO:74, SEQ ID NO:76 and SEQ ID NO:78.

* * * * *